United States Patent [19]

Jefferis, III et al.

[11] Patent Number: 4,908,188
[45] Date of Patent: Mar. 13, 1990

[54] GAS STERILANT SYSTEM

[75] Inventors: Raymond P. Jefferis, III, Wayne, Pa.; Phillip V. Engler, Tarrytown; Aaron A. Rosenblatt, New York, both of N.Y.

[73] Assignee: The Scopas Technology Company, Inc., New York, N.Y.

[21] Appl. No.: 183,514

[22] Filed: Apr. 14, 1988

Related U.S. Application Data

[63] Continuation of Ser. No. 698,434, Feb. 5, 1985, abandoned.

[51] Int. Cl.⁴ .............................................. A61L 2/24
[52] U.S. Cl. .................................... 422/111; 364/499; 364/500; 364/921.9; 364/922.4; 422/27; 422/28; 422/29; 422/37; 422/110; 422/116; 422/295; 422/305
[58] Field of Search ................... 422/3, 27, 28, 29, 34, 422/37, 110, 111, 114, 116, 295, 305; 364/413.01, 499, 500, 921.9, 922.4

[56] References Cited

U.S. PATENT DOCUMENTS

| | | | |
|---|---|---|---|
| 3,591,515 | 7/1971 | Lovely | 422/37 |
| 3,910,761 | 10/1975 | Hopkins | 422/108 |
| 3,982,893 | 9/1976 | Joslyn | 422/3 X |
| 4,067,691 | 1/1978 | McGady et al. | 422/116 X |
| 4,164,538 | 8/1979 | Young et al. | 422/116 X |
| 4,239,731 | 12/1980 | Gillis et al. | 422/34 X |
| 4,261,950 | 4/1981 | Bainbridge et al. | 422/116 X |
| 4,294,804 | 10/1981 | Baran | 422/34 X |
| 4,372,916 | 2/1983 | Chamberlain et al. | 422/3 X |
| 4,404,651 | 9/1983 | Grudowski | 364/900 |
| 4,414,193 | 11/1983 | Fredette et al. | 364/500 X |
| 4,431,159 | 2/1984 | Stubbs | 251/335.3 X |
| 4,447,399 | 5/1984 | Runnells et al. | 422/116 X |
| 4,457,892 | 7/1984 | Young | 422/3 X |
| 4,504,442 | 3/1985 | Rosenblatt et al. | 422/37 |

FOREIGN PATENT DOCUMENTS

| | | | |
|---|---|---|---|
| 108532 | 9/1939 | Australia | 422/29 |
| 2052800 | 1/1981 | United Kingdom | 422/27 |

OTHER PUBLICATIONS

"Disinfection, Sterilization, and Preservation (2 Ed.)", S. Block (Ed.), p. 184, 1970.
"Practical System for Steam-Formaldehyde Sterilizing", J. Pickerill, Lab Pract., vol. 24, No. 6, pp. 401-404, Jun., 1975.
"Sporicidal Properties of Chlorine Dioxide", Ridenour et al., Water & Sewage Works, vol. 96, No. 8, pp. 279-283, Aug., 1949.
"Triplicated Microprocessor Controlled Automatic Shutdown System", Mewies, Microprocessors & Microsystems, vol. 3, No. 8, pp. 347-351, Oct., 1979.
SYBRON/Castle Service Manual Castle 4040 Sterilizer. MOTOROLA MC14500B Industrial Control Unit Handbook, by V. Gregory, B. Dellande, pp. 75-85.
IEEE Micro Delcon Implementing State Diagrams in a High Level Language, Mar. 20, 1979, by Dr. R. D. Mical and S. C. Schwarm.

Primary Examiner—Barry S. Richman
Assistant Examiner—Jill Johnston
Attorney, Agent, or Firm—Kenyon & Kenyon

[57] ABSTRACT

A system for treating articles, preferably with a sterilizing, gas is disclosed. The system includes a chamber into which the articles are received and valves for supplying the sterilizing gas to the chamber and for removing the gas from the chamber after a predetermined time period. The sterilizing gas is generated on site from at least two components, thus minimizing problems in the transportation of the gas to the location. The sterilizing gas generated on site is preferably chlorine dioxide and the two components may be chlorine gas and sodium chlorite. The system includes a programmed microprocessor controller for controlling the valves executing a predetermined sequence of instructions. The predetermined sequence of instructions define a state diagram for the system having a plurality of successive states. In order to provide for system safety, the controller preferably employs a plurality of abort states to which the system returns in the event of a failure. Depending on the nature of the failure, the system automatically moves to the proper abort state.

50 Claims, 22 Drawing Sheets

| ADDRESS | DESCRIPTION | ADDRESS BUS BITS ||||||
|---|---|---|---|---|---|---|---|
| | | $A_{15}\ A_{14}\ A_{13}\ A_{12}$ | $A_{11}\ A_{10}\ A_9\ A_8$ | $A_7\ A_6\ A_5\ A_4$ | $A_3\ A_2\ A_1\ A_0$ |
| 00 - FF | INTERNAL RAM | 0 0 0 0 | — | $A_7\ A_6\ A_5\ A_4$ | $A_3\ A_2\ A_1\ A_0$ |
| 0000-0FFF | INTERNAL ROM | 0 0 0 0 | $A_{11}\ A_{10}\ A_9\ A_8$ | $A_7\ A_6\ A_5\ A_4$ | $A_3\ A_2\ A_1\ A_0$ |
| 1000 - 1FFF | EXTERNAL ROM | 0 0 0 1 | $A_{11}\ A_{10}\ A_9\ A_8$ | $A_7\ A_6\ A_5\ A_4$ | $A_3\ A_2\ A_1\ A_0$ |
| 2000 - 203F | EXTERNAL SRAM | 0 0 1 0 | 0 0 0 0 | 0 0 $A_5\ A_4$ | $A_3\ A_2\ A_1\ A_0$ |
| 4000 - 400F | CLOCK | 0 1 0 0 | 0 0 0 0 | 0 0 0 0 | $A_3\ A_2\ A_1\ A_0$ |
| 6000 - 6007 | A/D READ | 0 1 1 0 | 0 0 0 0 | 0 0 0 0 | 0 $A_2\ A_1\ A_0$ |
| C000 | X00 - X07 ⎫ | 1 1 0 0 | 0 0 0 0 | 0 0 0 0 | 0 0 0 0 |
| C001 | X10 - X17 ⎬ DIN | 1 1 0 0 | 0 0 0 0 | 0 0 0 0 | 0 0 0 1 |
| C002 | X20 - X27 ⎥ | 1 1 0 0 | 0 0 0 0 | 0 0 0 0 | 0 0 1 0 |
| C003 | X30 - X37 ⎭ | 1 1 0 0 | 0 0 0 0 | 0 0 0 0 | 0 0 1 1 |
| E000 | Y00-Y07 ⎫ | 1 1 1 0 | 0 0 0 0 | 0 0 0 0 | 0 0 0 0 |
| E001 | Y10-Y17 ⎬ DOU | 1 1 1 0 | 0 0 0 0 | 0 0 0 0 | 0 0 0 1 |
| E002 | Y20-Y27 ⎥ | 1 1 1 0 | 0 0 0 0 | 0 0 0 0 | 0 0 1 0 |
| E003 | Y30-Y37 ⎭ | 1 1 1 0 | 0 0 0 0 | 0 0 0 0 | 0 0 1 1 |
| E004 | WATCHDOG - RESET | 1 1 1 0 | 0 | 0 | 0 1 0 0 |

FIG. 3A

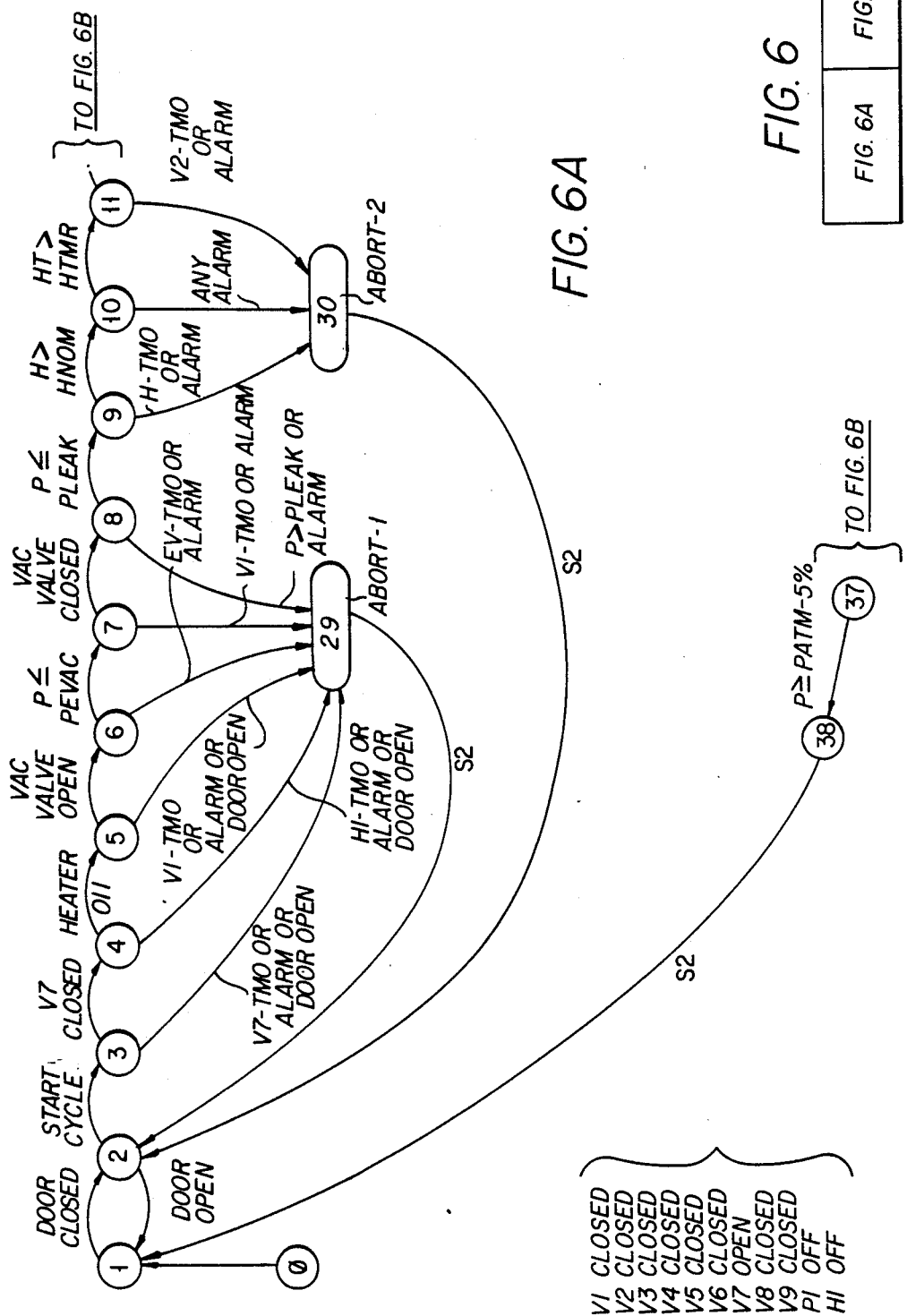

FIG. 7

| | | 0 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|---|---|
| DOOR OPEN | LT01 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| EVAC FAIL | LT02 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 |
| FILL FAIL | LT03 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 |
| STERIL FAIL | LT04 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 |
| PURGE FAIL | LT05 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 |
| LOAD UNSTER | LT06 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 |
| | LT07 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | LT08 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| READY | LT11 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| CYCLE | LT12 | 0 | 1 | 0 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 0 | 0 | 0 | 0 | 0 | 0 | 0 | 0 | 0 | 0 |
| EVAC | LT13 | 0 | 0 | 0 | 0 | 1 | 1 | 1 | 1 | 1 | 0 | 1 | 0 | 1 | 0 | 0 | 1 | 0 | 1 | 0 | 1 | 0 | 1 | 1 | 1 | 1 | 1 | 1 | 1 | 1 | 0 | 1 | 1 | 1 | 1 | 1 | 1 | 1 | 0 | 0 |
| FILL | LT14 | 0 | 0 | 0 | 0 | 0 | 0 | 0 | 1 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| STERIL | LT15 | 0 | 0 | 0 | 0 | 0 | 0 | 0 | 0 | 0 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| PURGE | LT16 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| GEM LOAD | LT17 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| | LT18 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| MAIN VAC | VV01 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| GAS ENABLE | VV02 | 0 | 0 | 0 | 0 | 0 | 0 | 0 | 0 | 0 | 0 | 0 | 1 | 1 | 1 | 1 | 1 | 1 | 1 | 1 | 1 | 1 | 1 | 1 | 1 | 1 | 1 | 1 | 1 | 0 | 0 | 0 | 0 | 0 | 0 | 0 | 0 | 0 | 0 | 0 |
| VAC CTRL | VV03 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 1 | 0 | 0 | 0 | 0 | 0 | 0 | 0 | 1 | 1 | 0 | 0 | 0 | 0 | 0 | 0 |
| GAS CTRL | VV04 | 0 | 0 | 0 | 0 | 0 | 0 | 0 | 0 | 0 | 0 | 0 | 0 | C | C | C | C | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| N2 CTRL | VV05 | 0 | 0 | 0 | 0 | 0 | C | 0 | 0 | 0 | C | C | C | C | C | C | C | C | C | C | C | C | C | C | C | C | C | C | C | 0 | 0 | 0 | 0 | 0 | 0 | 0 | 0 | C | 0 | 0 |
| H2O CTRL | VV06 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| STM VENT | VV07 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 1 | 0 | 0 | 0 | 0 | 0 | 0 | 0 | 0 | 1 | 0 | 0 |
| VAC VLV | VV08 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| VAC PUMP | PP01 | 0 | 0 | 0 | 0 | 0 | 0 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 0 | 0 | 1 | 1 | 1 | 1 | 1 | 1 | 1 | 0 | 0 |
| HEATER | HT01 | 0 | 0 | 0 | 0 | 0 | C | C | C | C | C | C | C | C | C | C | C | C | C | C | C | C | C | C | C | C | C | C | C | 0 | 0 | C | C | C | C | C | C | C | 0 | 0 |
| GAIN CHG. | GC1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

PROCESS STATES

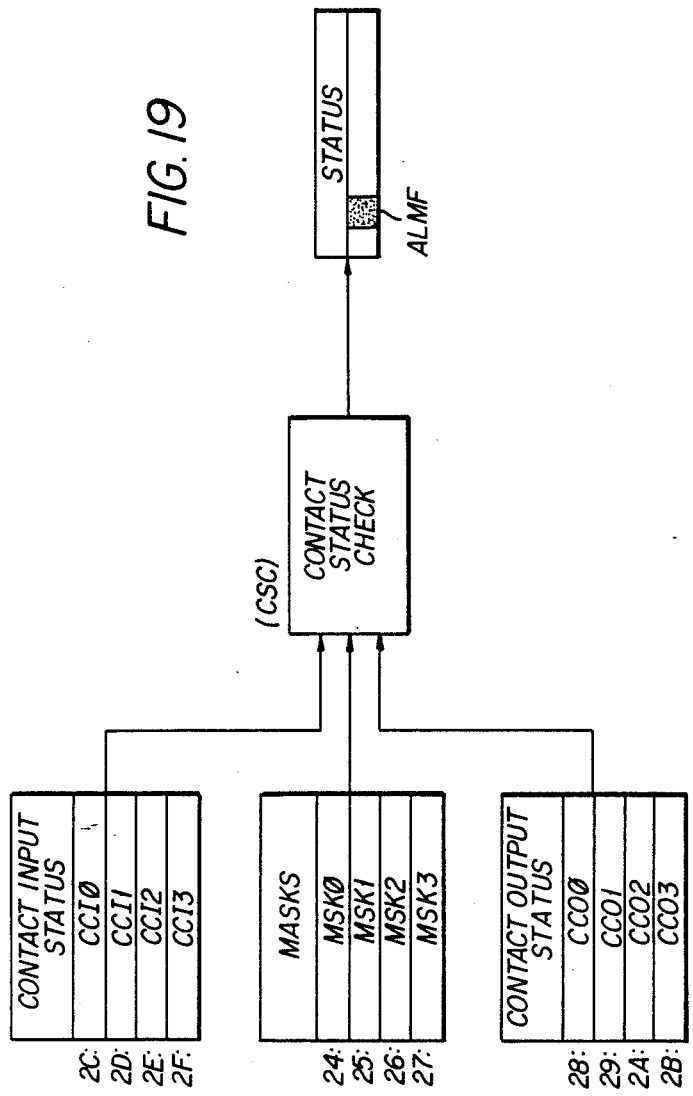
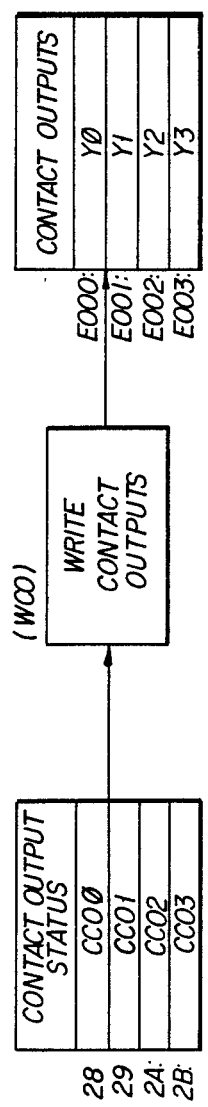

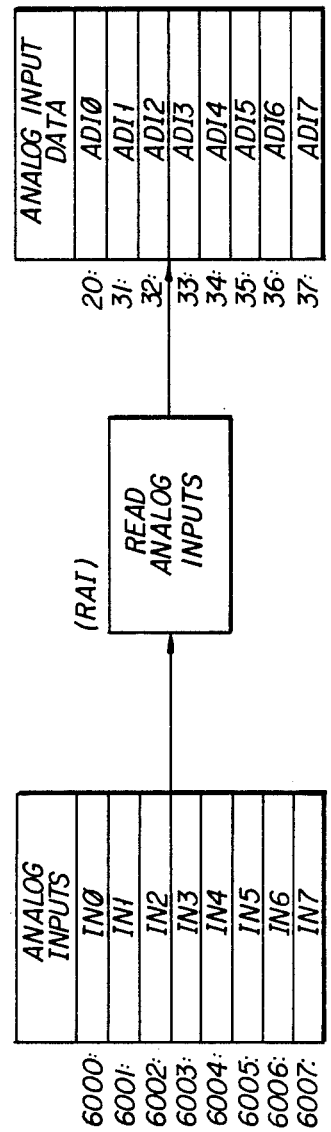
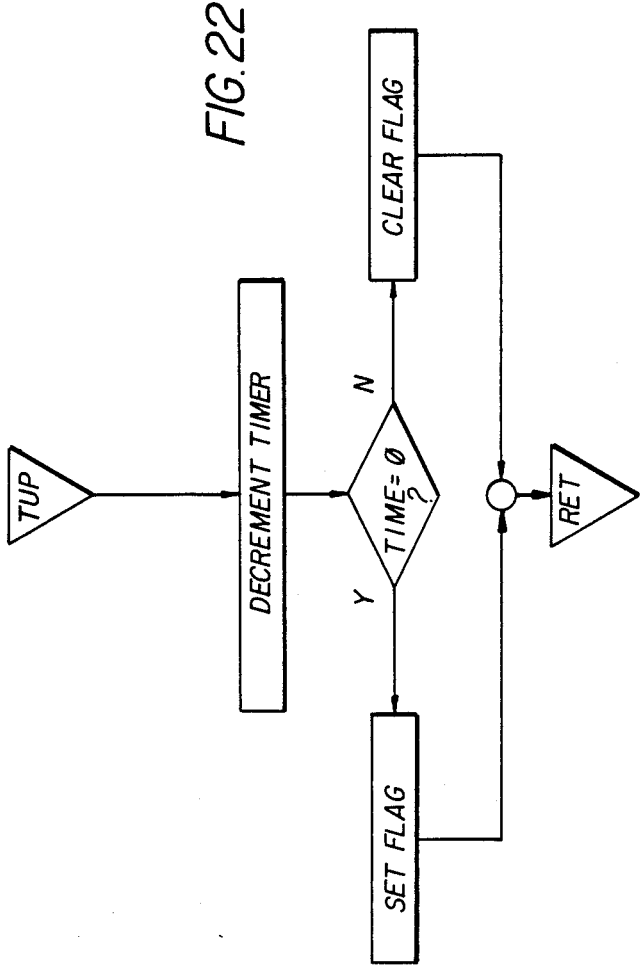

GAS STERILANT SYSTEM

This application is a continuation of application Ser. No. 698,434, filed Feb. 6, 1985 now abandoned.

BACKGROUND OF THE INVENTION

This application is related to copending applications Ser. Nos. 435,331 filed Oct. 19, 1982 now U.S. Pat. No. 4,504,442 and 601,443, filed Apr. 18, 1984, now U.S. Pat. No.4,681,739 the disclosures of which are hereby incorporated herein by reference.

The present invention relates to systems for delivering a gas to a confined chamber and to systems for sterilizing substances and articles and particularly to systems using a sterilizing gas to sterilize articles, for example medical apparatus such as utensils and instruments which may have been contaminated by foreign substances. The system of the present invention can also be used to sterilize non-medical articles and substances, as required. The system of the present invention relates particularly to a gas sterilizing system wherein two components which react to provide sterilizing amounts of a gas are combined in the field by the apparatus of the present invention. This allows the components which react to form the sterilizing gas to be shipped separately, which minimizes the possibility of accidents.

In particular, the present invention relates to a system using chlorine dioxide as the sterilizing gas. Chlorine dioxide gas is both unstable and toxic to humans. For example, chlorine dioxide gas, will, over time, decompose into its constituent parts and accordingly, it cannot be transported easily. It is therefore undesirable to transport chlorine dioxide gas. Moreover, chlorine dioxide gas is somewhat explosive and also has a propensity to undergo catalytic decomposition. The components which react to form chlorine dioxide gas (e.g., sodium chlorite and chlorine gas), however, may be transported relatively easily and reacted on site to provide the sterilizing gas chlorine dioxide.

Prior systems have typically used ethylene oxide gas as a sterilant. For example, the castle 4040 ethylene oxide sterilizer manufactured by Sybron Corporation, Medical Products Division, is an example of such a prior system. Although ethylene oxide has been used as a sterilizing gas in the prior systems, chlorine dioxide is a preferred sterilant.

Furthermore, the systems used in the past have typically been of rather simple design and have not included advanced means for maintaining the reliability of the devices and safeguarding against accidents. Additionally, these systems have not provided a great deal of redundancy so that if a component of the system failed, manual intervention or service personnel was required to correct the failure before the sterilizing process could continue.

SUMMARY OF THE INVENTION

It is an object of the present invention to provide a sterilizing system which uses a gas having bacteriocidal, sporicidal, fungicidal and/or viricidal properties to sterilize articles.

It is a further object of the invention to provide a sterilizing system in which at least two components which react to provide a sterilizing gas are reacted on site within the apparatus of the present invention to provide effective amounts of the sterilizing gas.

It is yet a further object of the present invention to provide a sterilizing system wherein the sterilant is chlorine dioxide gas.

It is still a further object of the present invention to provide a gas sterilizing system having built-in redundancy and means for maintaining the reliability and safety of the system.

It is still yet another object of the present invention to provide a gas sterilizing system which is versatile and which is controlled by a programmed microprocessor.

According to one embodiment of the invention, these and other objects of the present invention are achieved by a system for treating articles with a gas comprising first means for receiving a first component, second means for receiving a second component, the first and second components, when reacted together, forming the gas, means for reacting the two components together for forming the gas, valve means for supplying the gas to the chamber means to treat the article in the chamber means, means for removing the gas from the chamber means, electronic controller means for controlling the means for reacting, means for supplying and means for removing, comprising computer means executing a predetermined sequence of steps so as to cycle the apparatus through a series of successive states defining a cycle in which the article is treated by the gas and wherein the gas is thereafter removed from the chamber means so as to render the atmosphere in the chamber means within acceptable standards of safety.

According to another embodiment of the invention, a system for treating articles with a gas is provided comprising chamber means for receiving articles to be treated, means for supplying the gas to the chamber means comprising valve means coupled to the chamber means for supplying the gas to the chamber means, means for removing the gas from the chamber means after a predetermined time interval, electronic control means receiving a plurality of electrical signals associated with ones of measured parameters from the chamber means for controlling the valve means and the means for removing, the electronic control means comprising computer means for cycling the apparatus through a plurality of states in accordance with a predetermined sequence of instructions, the computer means including means for aborting the operation of the apparatus to one of a plurality of defined failure states in response to a failure of the apparatus, the selected failure state dependent on the state in the cycle in which the failure occurred.

According to still another embodiment of the invention, a system for treating articles with a gas is provided comprising chamber means for receiving articles to be treated, means for supplying the gas to the chamber means comprising valve means coupled to the chamber means for supplying the gas to the chamber means, means for removing the gas from the chamber means after a predetermined time interval, electronic control means receiving a plurality of elecrical signals associated with ones of measured parameters from the chamber means for controlling the valve means and the means for removing, the electronic control means comprising computer means for cycling the apparatus through a plurality of states in accordance with a predetermined sequence of instructions, the computer means including memory means, and further comprising means for receiving input signals from the valve means indicative of the closed or open condition of the valve means and means for transmitting output signals to the valve means to selectively open or close the valve means, image signals of the input and output signals being stored in the memory means, mask means being stored in the memory means, the computer means comparing the image signals of the input and output signals and generating an alarm signal if the input and output image signals do not agree in response to the setting of a bit in the mask means.

Other objects, features and advantages of the present invention will be apparent from the description which follows.

BRIEF DESCRIPTION OF THE DRAWINGS

The present invention will be described in greater detail with reference to the accompanying drawings in which:

FIG. 3A is a table of addresses used in the electronic controller of FIG. 3 and the corresponding components or signals controlled by the addresses;

FIGS. 6, 6A and 6B are a state diagram for the gas sterilant system according to the present invention;

FIG. 7 is a state output matrix corresponding to the state diagram of FIGS. 6A and 6B for the gas sterilant system according to the present invention;

FIG. 19 is a flowchart for a program implemented in the control unit for providing an additional alarm in the event of a component failure;

FIG. 20 is a flowchart for a program implemented in the control unit for writing out data to the controlled components of the system;

FIG. 21 is a flowchart for a program implemented in the control unit for reading in analog input data from the controlled system;

FIG. 22 is a general flowchart for a program implemented in the control unit for providing the various timed functions of the system;

DETAILED DESCRIPTION

Overall System

Figure 1:
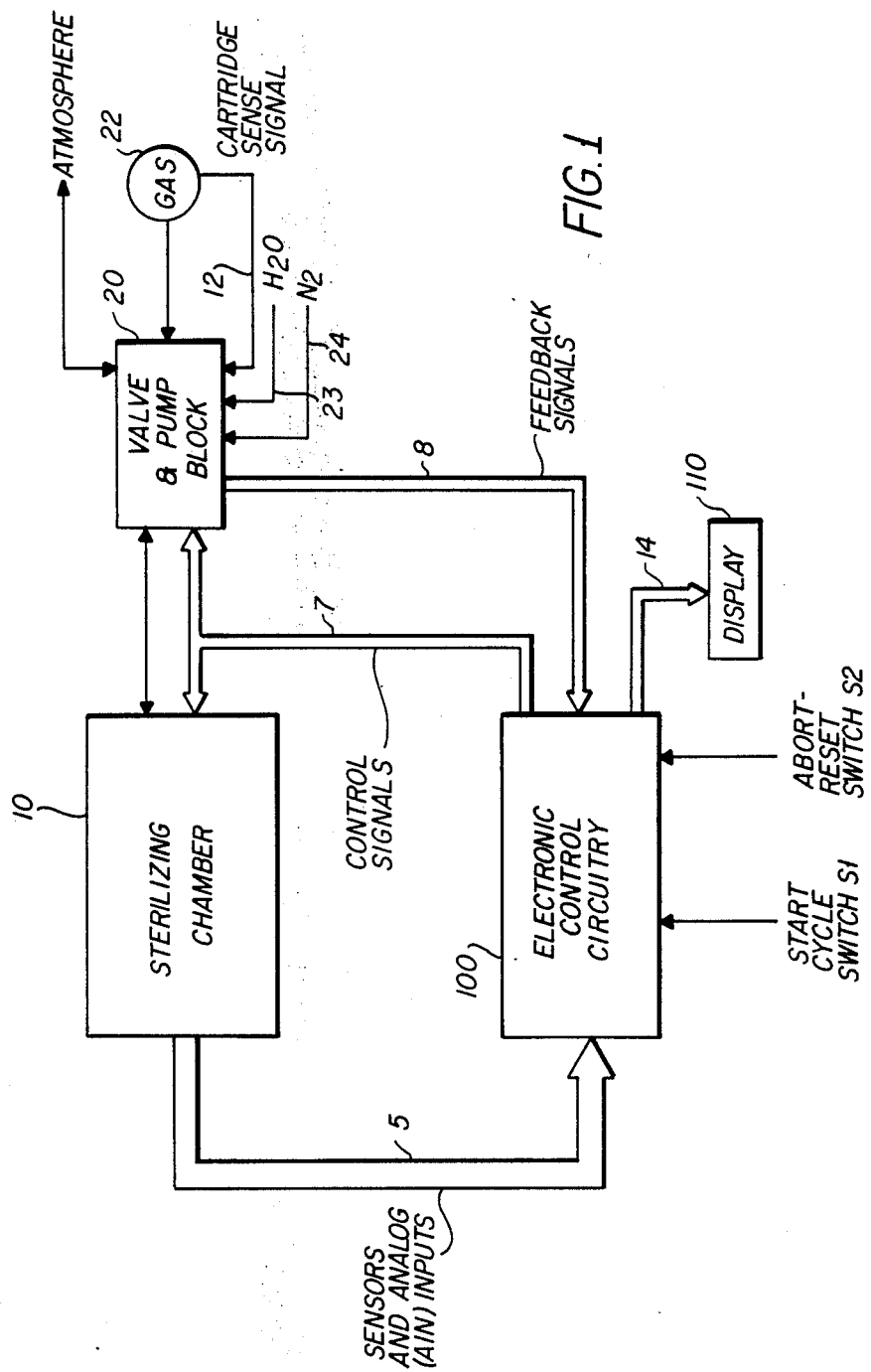
FIG. 1 is a block diagram of the overall gas sterilant system according to the invention.

With reference now to the drawing figures, FIG. 1 shows the overall gas sterilant system. The system comprises a sterilizing chamber 10, electronic control circuitry 100 which is preferably microprocessor controlled, valve and pump block 20 and displays 110. Sensor inputs 5 including signals generated by appropriate sensors in chamber 10 and related to temperature, pressure, humidity and sterilizing gas concentration in the chamber 10 are fed from the sterilizing chamber 10 to control circuitry 100. The sensor inputs include both analog signals relating to the above measured chamber parameters and certain digital signals, e.g., a signal indicative of when the temperature in the chamber has reached a desired value, to be explained in more detail below. A START CYCLE switch S1 initiates operation of the system and an ABORT-RESET switch S2, as described in more detail later, is used to recycle the system states to a defined condition if an abort mode is attained, i.e., if a failure or alarm condition occurs. The operation of valve and pump block 20 will be described in more detail below, and includes a source of chlorine dioxide gas 22 which is produced on location from separated components, water vapor 23 and nitrogen 24. The valve and pump block is also vented to the atmosphere, as shown. Valve and pump block 20 includes a number of sequenced and controlled valves and a vacuum pump for providing the necessary conditions in the sterilizing chamber at the appropriate times. Because of the instability and potential toxicity of chlorine dioxide, the preferred sterilizing gas, it is preferable to transport components, which when reacted, form the chlorine dioxide gas. For example, the components may be sodium chlorite, $Na_2ClO_2$ and chlorine gas, $Cl_2$.

Appropriate control signals 7 are fed by the electronic control circuitry 100 to the valve and pump block 20 and chamber 10 for controlling components of the system. Furthermore, feedback signals 8 from the controlled components are fed back to the control circuitry 100 so that the controller can monitor the state of the system and signals 14 are coupled to display panel 110 for informing the operator of the status of the system.

Additionally, a cartridge sense signal 12 is fed from the attached gas cartridge ($Cl_2$ component cartridge) to indicate that a gas component cartridge has been coupled into the system.

General Functions

Figure 2:
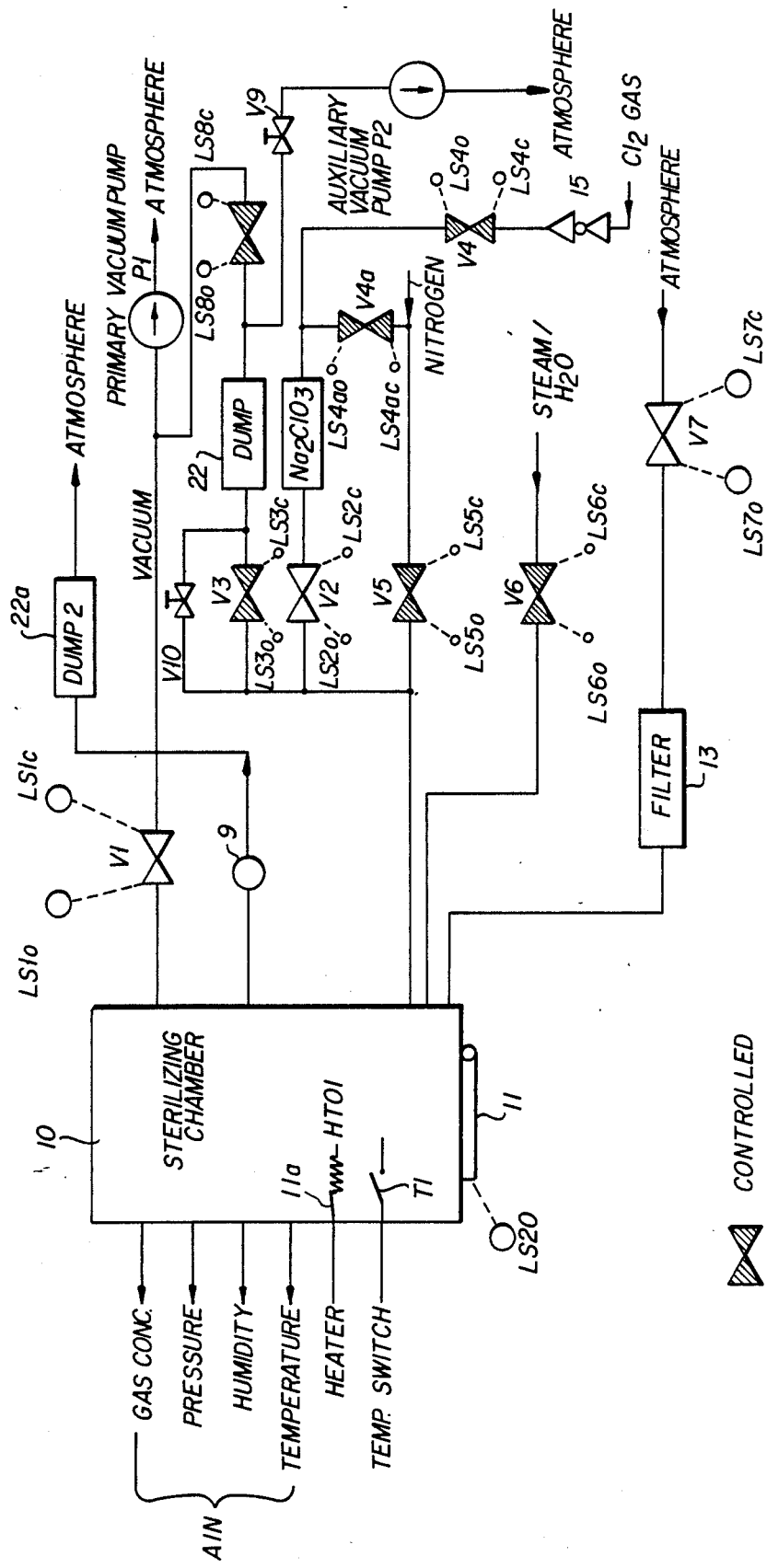
FIG. 2 is a block diagram of the sterilizing chamber and the valve and pump block of the gas sterilant system according to the present invention.
Figure 5:
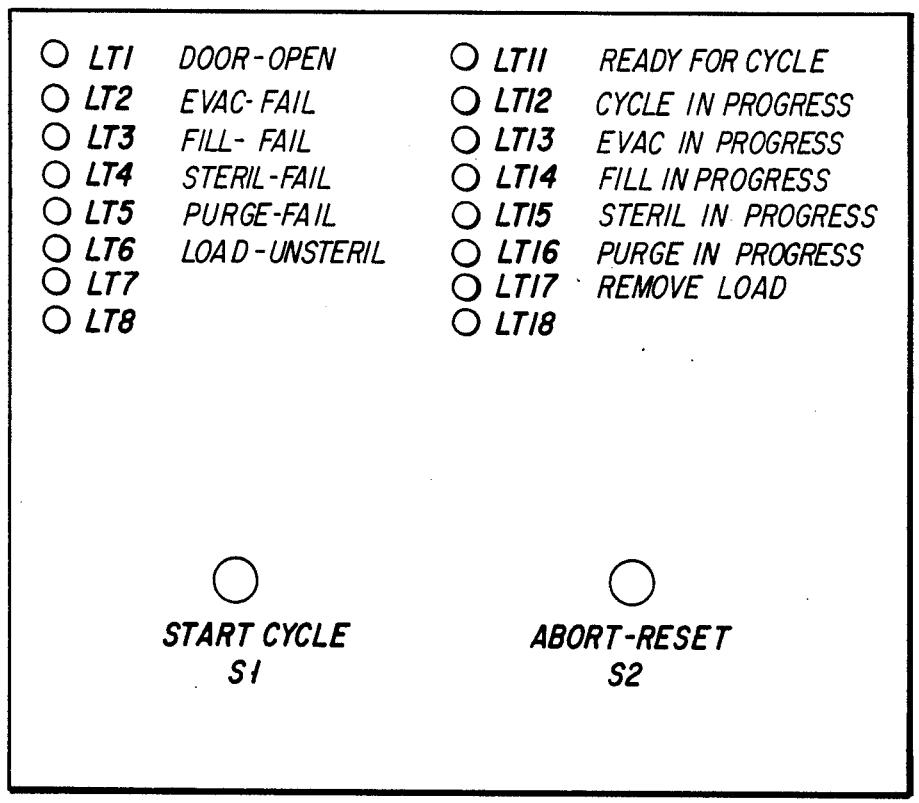
FIG. 5 is a front view of one embodiment of a control panel for the gas sterilant system showing the controller display lights and control switches.

FIG. 2 shows the arrangement of valve and pump block 20 in more detail. Valve and pump block 20 includes a series of valves V1, V2, V3, V4, V4a, V5, V6, V7, V8, V9 and V10, pumps P1 and P2, air filter 13, a detoxifier 22 for detoxifying the evacuated chlorine dioxide gas, which may be implemented as explained in the above copending patent applications, and appropriate sources of water vapor, nitrogen, $Cl_2$ gas, air, and sodium chlorite. As shown in FIG. 2, some of the valves are merely sequenced, while others are controlled in response to selected ones of the values of the measured process variables, e.g., gas concentration, humidity level and pressure. For safety reasons, each valve (V) is fitted with two limit switches (LS) to indicate the open (e.g. LS2o) or closed condition (e.g. LS2c) of the valve. In the attached software liting, the open limit switches are referred to by the designation LSOx and the closed limit switches by the designation LSCx. Both switches must be in their proper positions at the proper times during the entire cycle in order that the cycle not be aborted. In addition, a number of lights are provided on a display panel, as shown in FIG. 5, which indicate the progress of the sterilization cycle or the occurrence of possible fault conditions. A cycle can be started by the operator, after the chamber door 11 is closed, by momentarily depressing the START-CYCLE (S1) switch. See FIG. 1. Thereafter the cycle proceeds automatically according to a program stored in the microprocessor memory of the electronic controller 100. This process will be described in more detail below.

Furthermore, in order to provide redundancy, a number of manually controlled valves, e.g. valves $V_9$ and $V_{10}$, are provided in case valves $V_3$ and $V_8$ do not open. These valves can be manually operated by service personnel so that potentially toxic gases can be removed via detoxifier 22 in the event valves $V_3$ and $V_8$ fail to open when sterilizing gas is in the chamber. An auxiliary vacuum pump is also provided so that the gas can be drawn out via the manually operated valves.

Sterilization Cycle

Figure 6B:
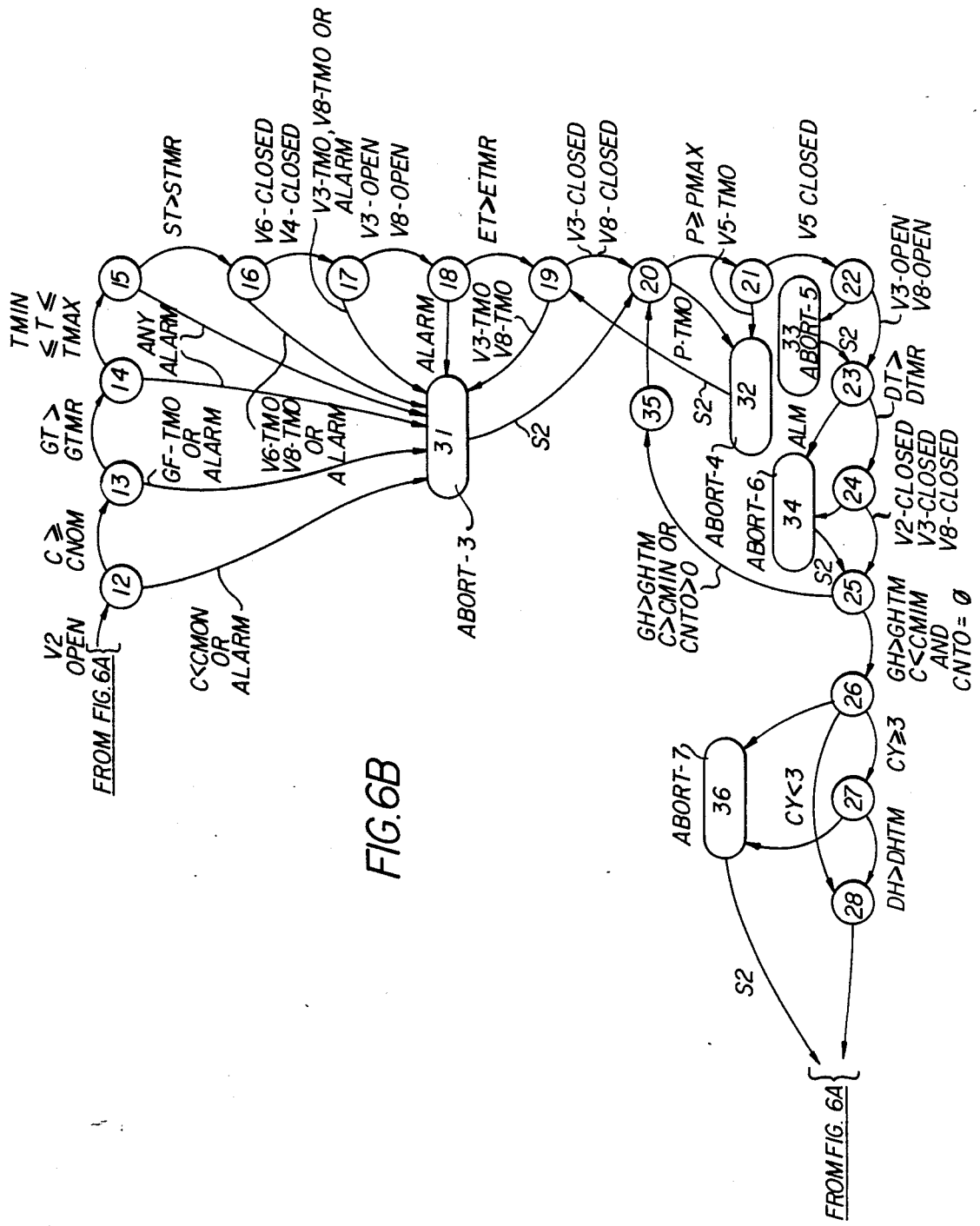
Figure 7A:
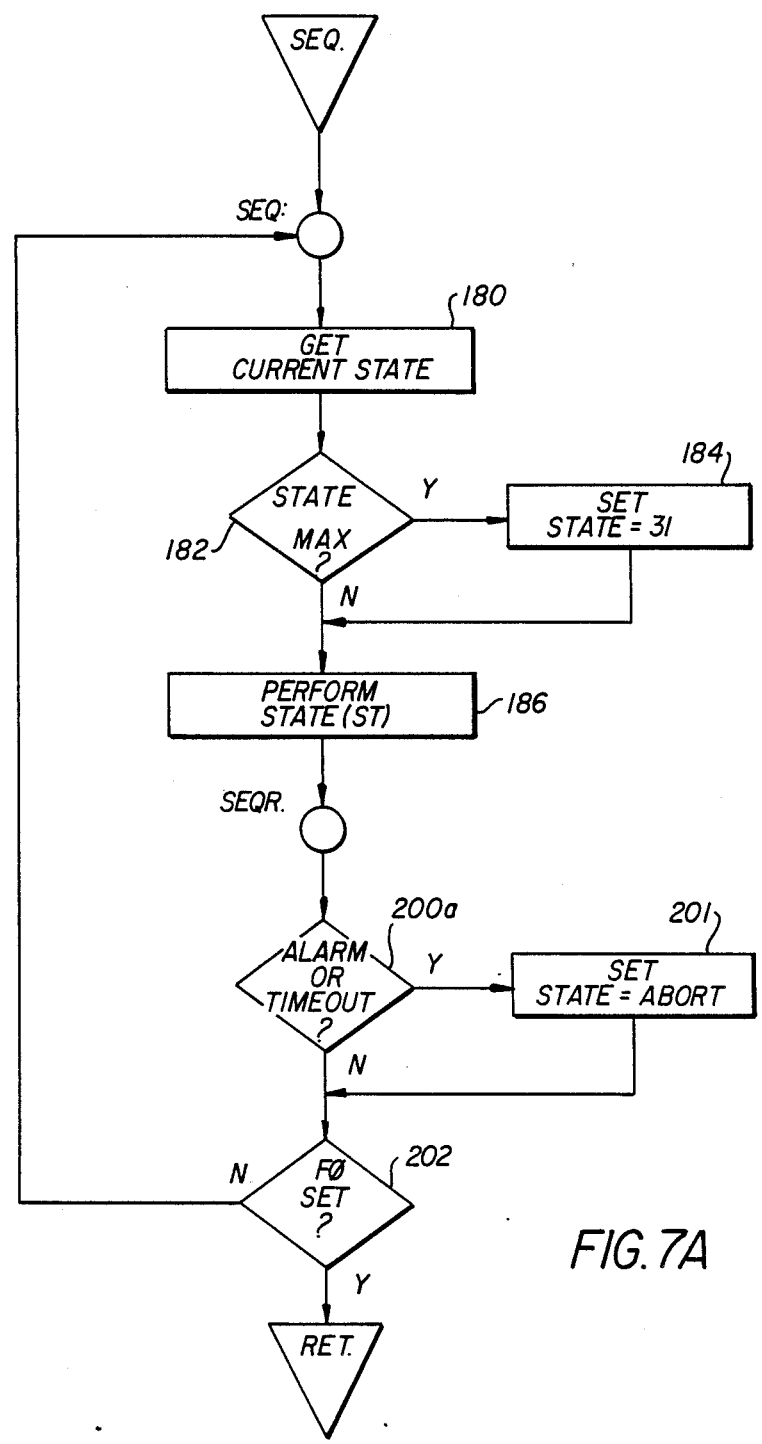
FIGS. 7A and 7B are flowcharts for the sequencing program for implementing the state diagram of FIGS. 6A and 6B.
Figure 7B:
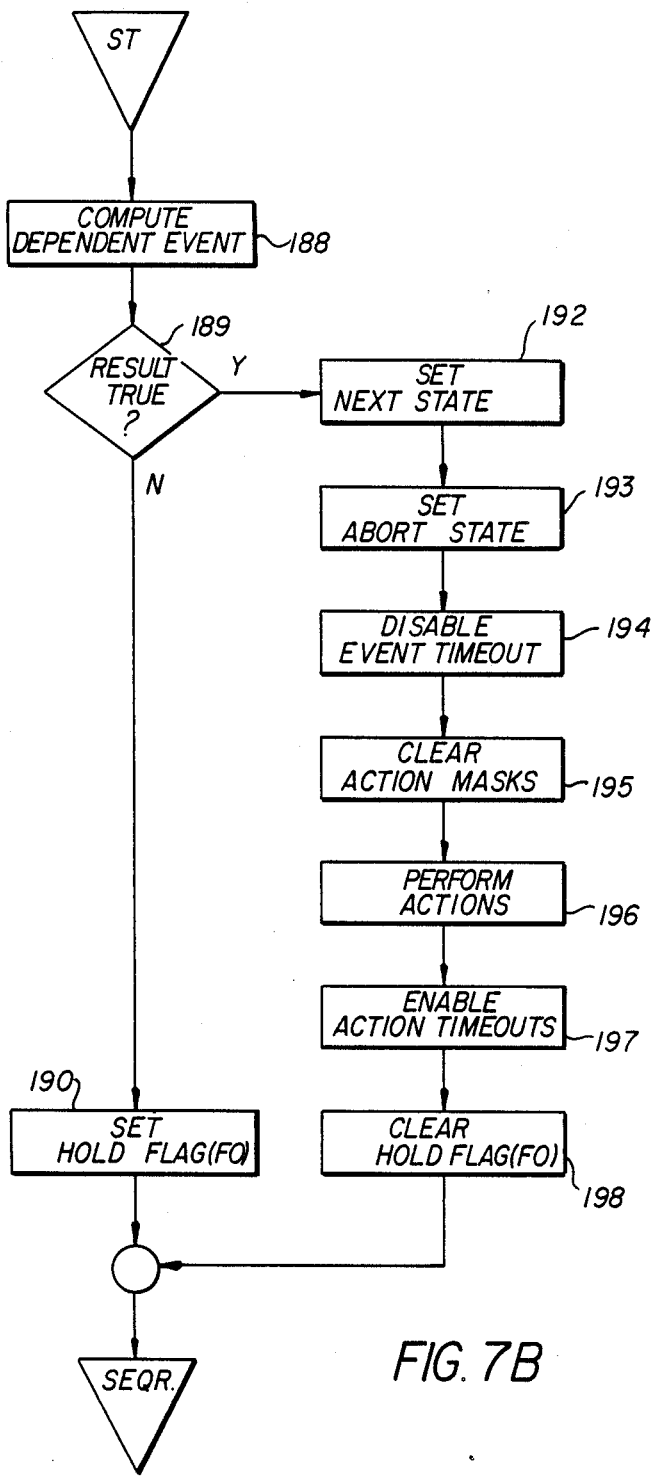

The sterilization cycle is an interlocked sequence of events and consequent actions under microprocessor control. The steps of this sequence are detailed in the state diagram of FIG. 6 and state output matrix of FIG. 7. These steps are performed by a sequencing program, the flowchart for which is shown in FIGS. 7A and 7B and the details of which are disclosed in the program listing contained in the appendix. Two types of events occur during the sequence, independent and dependent events. Some independent events are external events and include contact input signals to the controller from the controlled valves (e.g., the limit switches), and are referred to by the symbols X0x to X3x in FIG. 3. Each contact input signal is one bit of an eight bit word and the collection of such control input signals shall be referred to herein generally as digital inputs (DIN). Independent events also include the reception of signals corresponding to measured or analog process values (AIN), such as pressure, temperature, humidity and sterilizing gas concentration. The measured value signals are associated with logical comparison operations performed by the controller. Other independent events are internally declared, and these typically result in the illumination of an indicator light on the display panel, shown in FIG. 5. The controller evaluates the dependent events, which are logical combinations of independent events, to single TRUE or FALSE results. When the dependent event becomes true, a corresponding action is performed, i.e. the control system moves to a new process state, defined by the state output matrix of FIG. 7. If the dependent event is not true, the controller holds the process state in its memory and waits for a period of 50 milliseconds before reevaluating the dependent event. In the case of a system failure, the system automatically transfers to an appropriate ABORT state immediately, as will be described in greater detail below. This process continues until the cycle has been completed or aborted.

The sterilization cycle can be thought of as a succession of STATES, or points at which the process awaits the completion of some function. The STATE DIAGRAM, shown in FIG. 6, defines the succession of process states and the events which transfer the process between these states. The state diagram includes a number of ABORT states, which are entered in the event of a system failure. An ABORT state is a state having a set of defined conditions and is entered in the event of a system failure, e.g., a computer failure, a failure of a valve or other system component. As shown, the ABORT state appropriate to a fault condition changes as the sterilization cycle progresses. These various ABORT states are provided in order to insure safe operation of the equipment, i.e., the system proceeds to different ABORT states dependent upon the state at which the ABORT condition occurred. In this way, the system takes into account that different steps may be necessary depending on whether, e.g., sterilizing gas has entered the chamber 10 or only nonsterilizing substances are in the chamber. At each stage in the process, not only will failure of the awaited event cause transfer to an ABORT state, but the failure of any valve to maintain its commanded position will also abort the cycle. This is a safety interlock which is described in greater detail below. After each successful transfer of the process to a new state, a specified action must be taken. These state-dependent actions are summarized in FIG. 7, which is the state output matrix corresponding to the state diagram of FIG. 6 and which identifies the conditions of various components of the system in the various states. The sterilization controller is programmed to follow this event-action format according to the state-diagram definition. This insures that all state transfers are defined and that no other transfers can take place.

Safety Considerations

Figure 8:
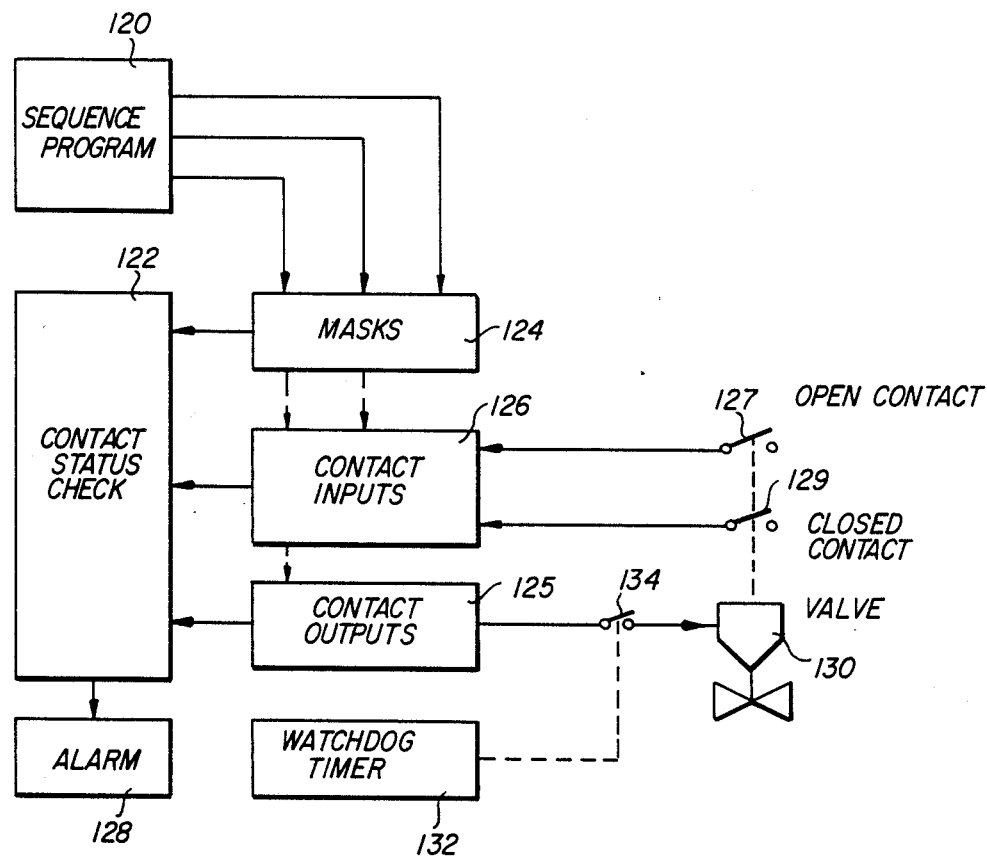
FIG. 8 is a block diagram of the safety interlock arrangement for the gas sterilant system according to the present invention.

The sterilization system is provided with a number of checks to insure correct operation of the various valves and other components. As will be described in more detail below, interlock software implemented by the controller main timing program confirms the correct position of all valves every 6250 microseconds. An alarm condition is declared any time a valve is not in its commanded state. The operation of these interlocks differs from typical relay logic, or programmable logic controllers, in that interlock checking continues after valve actuation has taken place and can lead to different failure programming (ABORT states) at each process stage. The correct status of a valve is latched into memory after actuation is confirmed, and this latched condition is checked every 6250 microseconds. FIG. 8 is a block diagram of the safety-interlock components necessary to perform this checking routine. Failure to pass either an initial event-timeout condition following actuation or any subsequent status check will result in abnormal termination of the sterilization cycle. A sequence of control actions for safe termination of the cycle is defined for every point in the sterilization cycle, and is initiated immediately in the event of any abnormal (ALARM) process condition. This intensive status checking according to the invention prevents deliberate bypassing of the interlock switches in the field, since if a limit switch is bypassed, at some point in the system cycle the switch will be determined to be in an improper position, thus causing the system to enter an ABORT state.

Figure 18:
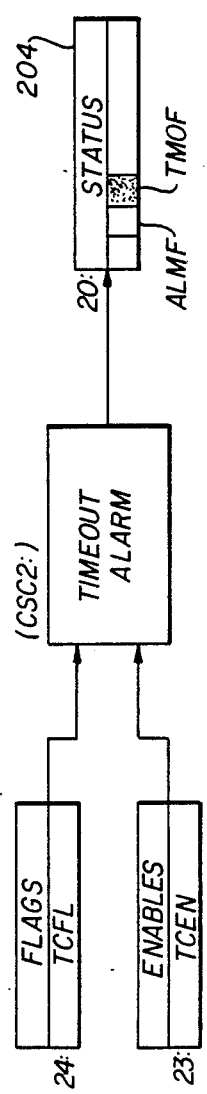
FIG. 18 is a flowchart for a program implemented in the control unit for providing a timeout alarm in the event of a component failure.

As shown in FIG. 8, the safety interlock system includes a Sequencing Program 120 stored in internal memory (ROM) of the electronic controller. Sequencing program 120 is identified in a listing of the program resident in memory attached hereto, as SEQ and the flowchart for this program is shown in FIGS. 7A and 7B. Also stored in memory is a Contact Status Check program 122 and a series of masks 124 which are determined by the particular point in the sequence program. The Contact Status Check program is identified in the appendix as CSC and a flowchart therefor is shown in FIGS. 18 and 19. Inputs 126, which are images stored in memory of actual input signals from both "open" limit switch contacts 127 (closed when a valve is open and open when a valve is closed) and "closed" contacts 129 (closed when a valve is closed and open when a valve is open) are provided, as well as inputs from other components, such as the sterilizing chamber 10 door 11. A series of contact outputs 125 are also provided by the particular state of the sequencing program. The Contact Status Check program 122 compares the contact inputs with the contact outputs 125. Whenever an input differs from the desired value, as established by the output, an alarm condition is declared if, and only if, a corresponding bit is turned on in the Mask 124. This safety feature detects any incorrect valve position immediately. A hardware implemented watchdog timer 132 is utilized to provide an extra level of safety by disabling all outputs to the valves 130 by opening electronic switches 134 when the timer times out if the microprocessor controller should fail, thereby preventing energization of any of the valves in the valve and pump block 20 in the event of a computer failure.

Figure 12:
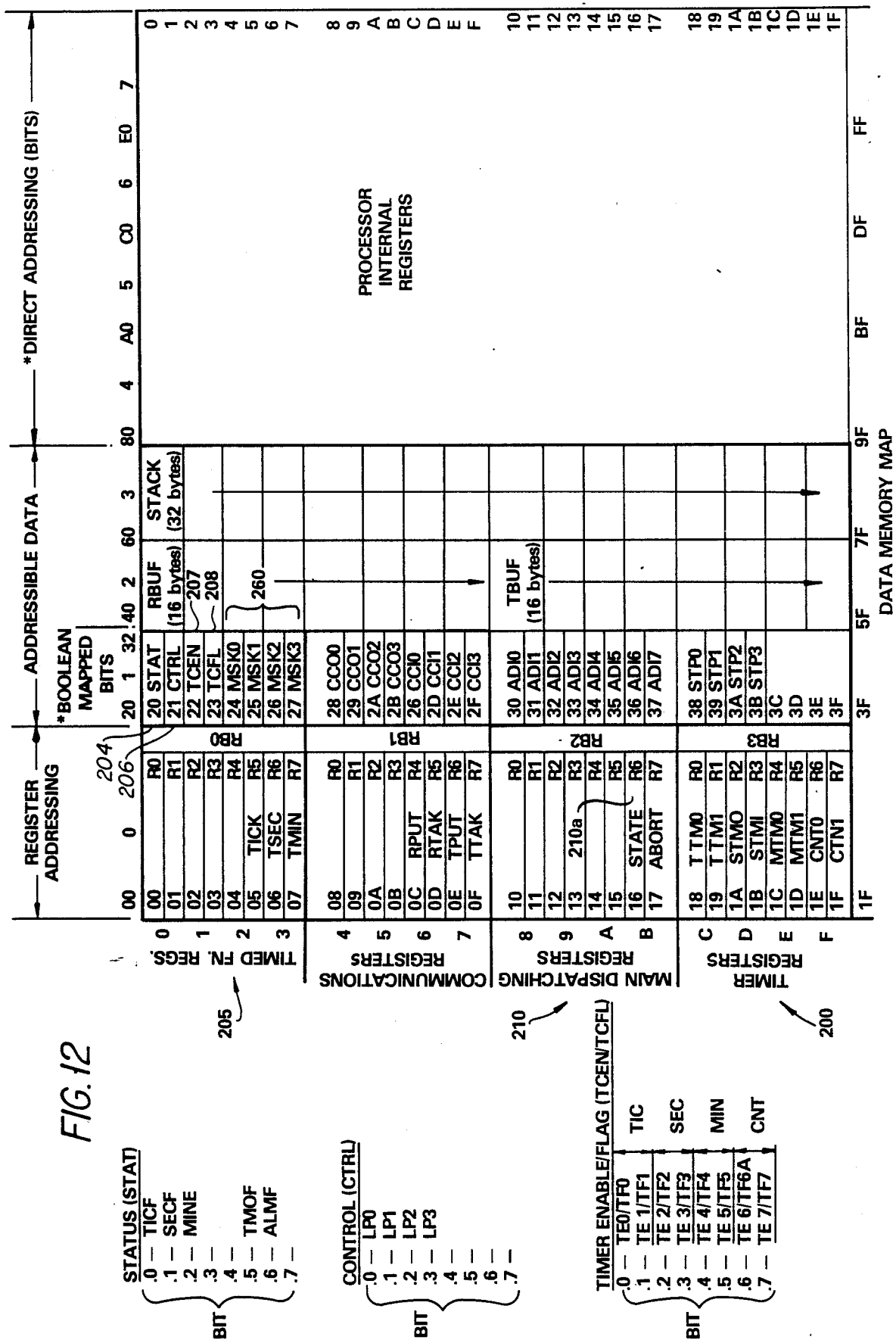
FIG. 12 is a memory map of the data memory of the electronic control circuitry for the gas sterilant system according to the present invention.

FIGS. 7A and 7B are a flowchart for the sequencing program SEQ. The sequencing program is entered from another program, called the Main Dispatching Program, which essentially checks for flags generated at appropriate time intervals and which determines when specific functions should be performed. As shown in FIG. 7A, when the sequencing program is entered, the current state of the system is retrieved from memory, as shown at 180. The current state is stored in a register 210a in internal CPU RAM, as shown in FIG. 12. The organization of internal CPU RAM will be discussed in more detail in connection with FIG. 12 later. At 182, a check is made to determine if the state exceeds the maximum state number. If it does, an ABORT state, state 31, to be discussed in more detail in connection with FIG. 6, is entered at 184. Otherwise, the conditions for the next state are performed at 186 by entering the program ST, the flowchart for which is shown in FIG. 7B.

As shown in FIG. 7B, program ST first evaluates each dependent event to a single true or false result, as shown at 188 and 189. Each dependent event is a logical combination of a number of independent events, each of which must be specified if the dependent event is true. If the dependent event is not true, a hold flag (F0) in a memory location in the microprocessor internal RAM (see FIG. 12) is set at 190. Otherwise, the next state is set at 192 and a new ABORT state, if a new ABORT state is required, is set, but not entered, at 193.

At 194, the timeout for the previous event must be disabled so that the timeout will not cause an alarm condition to be generated, which could cause an ABORT state to be reached. Timeouts are provided by program implemented timers, which monitor for the occurrence of a specified action, e.g. the movement of a valve, within a preset time defined by the timer. If the specified action has occurred, the timeout must be disabled because the timer continues to run. In order to disable the timeout, as shown in FIG. 18, a flag in the Timer Counter Enable Register (TCEN) 207 in internal RAM (FIG. 12) is cleared. In this way, when the flag for the timer is set into the Timer Counter Flag Register (TCFL) 206 (FIG. 12) when the timer runs out, no alarm will be generated. If a timeout alarm is generated, a bit TMOF is set in the STATUS register, as shown in FIG. 18.

At 195, the masks are cleared, i.e., bits corresponding to the particular events which are to take place are set to a "don't care" condition, so that the change of the corresponding bits in the contact outputs do not set off an alarm condition by the contact status check program. At this point, the action may be performed, as shown at 196. Subsequently, the timeout count for the action is loaded into the appropriate one of the timer registers 200 (FIG. 12) as will be explained in more detail later. The action timeout flag is then enabled to monitor for the timely occurrence of the current monitored action as shown at 197. The hold flag F0 is then cleared at 198 and a return is made to the flowchart of FIG. 7A, to the point denoted SEQR.

At 200a, a test is performed to determine if an alarm or timeout condition has occured. If an alarm or timeout has occurred, the current state is set to the current ABORT state at 201 immediately. Then, the hold flag F0 is checked at 202 to determine if it has been set. If it has, a return is then made to the background or main dispatching program from which all subroutines are entered. If flag F0 has not been set, the system remains in the sequencing program to continue to the next state and only exits once flag F0 is set.

FIG. 19 shows the contact status check program in more detail. As shown, the contact input status corresponding to the contact inputs are stored in appropriate locations in the internal RAM of the system microprocessor. The memory locations are as indicated. See FIG. 12. The same is done for the contact output status bits, which specify the events to occur for a particular state. The Masks MSK0–MSK3, also stored in internal RAM, are evaluated by the contact status check program. If the contact inputs vary from the contact outputs, an alarm condition is generated by setting a bit in the status register 204, which is a location in RAM (see FIG. 12), but this is only done if the corresponding bit in the Mask is turned on. If the bit is off, indicating that a change of the corresponding output is to be allowed to occur, no alarm will be generated, and the contact outputs will be written into an output buffer, to be described in more detail below, to actuate the appropriate controlled or sequenced component, e.g., a valve or pump, without operating an alarm.

Additional safety features are also provided for in the system. As discussed above, manually actuable valves V9 and V10, operated by service personnel, and auxiliary pump P2 are provided in the event valves V8 and V3 and main pump P1 do not operate properly, thus providing a degree of redundancy. Furthermore, as shown in FIG. 2, safety features are provided to prevent the possibility of excessive temperatures and pressures in the sterilizing chamber 10. A thermally activated switch 11a is provided in series with heater HT01 in the chamber to detect excessive temperature. For example, should the heater HT01 fail to turn off, the thermostatic switch 11a will sense an excessive temperature and interrupt the circuit.

Additionally, should excessive pressures develop in the chamber, a pressure relief valve 9 is provided for venting gases in chamber 10 through a second detoxifier 22a to the atmosphere.

Also provided is a check valve 15 in series with valve V4 which supplies sterilizing chlorine gas to the system. Check valve 15 prevents the possibility of nitrogen gas from the nitrogen cannister pressurizing the chlorine gas cannister should valves V4 and V4a fail to close. Check valve 15 only allows chlorine gas to flow out of the chlorine gas cannister and prevents nitrogen gas from flowing into the chlorine gas cannister if valves V4 and V4a fail to close.

Operator Interactions

The apparatus and sterilization cycle of the system according to the invention provide for minimal operator intervention and maximum safety. FIG. 5 shows an embodiment of a display panel for the invention showing the various display lights. Certain lights are provided but not used, for expansion purposes. The sterilization cycle cannot be initiated until the chamber 10 door 11 has been properly closed. The DOOR-OPEN light (LTI) will then be extinguished, as shown by LT01 changing state from a "1" state in state 1 to a "0" state in state 2 of FIG. 7, and the READY-FOR-CYCLE light (LT11) will be illuminated. See also FIG. 5. To start the cycle, the operator merely presses the START-CYCLE (Sl) switch (see FIG. 1) when ready. Thereafter, no operator intervention is required until the cycle ends, with illumination of the REMOVE-LOAD light (LT17), or until an alarm condition has halted the cycle. In the latter eventuality, one of the alarm lights indicating the failure will be on. The operator notes which lights are on, takes the necessary action and then presses the ABORT-RESET (S2) switch when ready to cycle the system back to a defined condition and to avoid the failure condition, if possible. For example, if the PURGE-FAIL light (LT5) is on, due to the possibility of an empty nitrogen tank, the tank should be replaced before pressing the S2 switch. Similarly for other failure modes, an attempt should be made to diagnose and remedy the failure condition before pressing switch S2. The subsequent actions to abort the cycle are then predetermined and automatic. No further operator intervention is necessary. Furthermore, redundancy has been provided in the system so that if a component fails, another component, e.g., a pump or valve, can take the place of the failed component so that the system can be brought out of its failure state.

Control Circuitry Design

Figure 3:
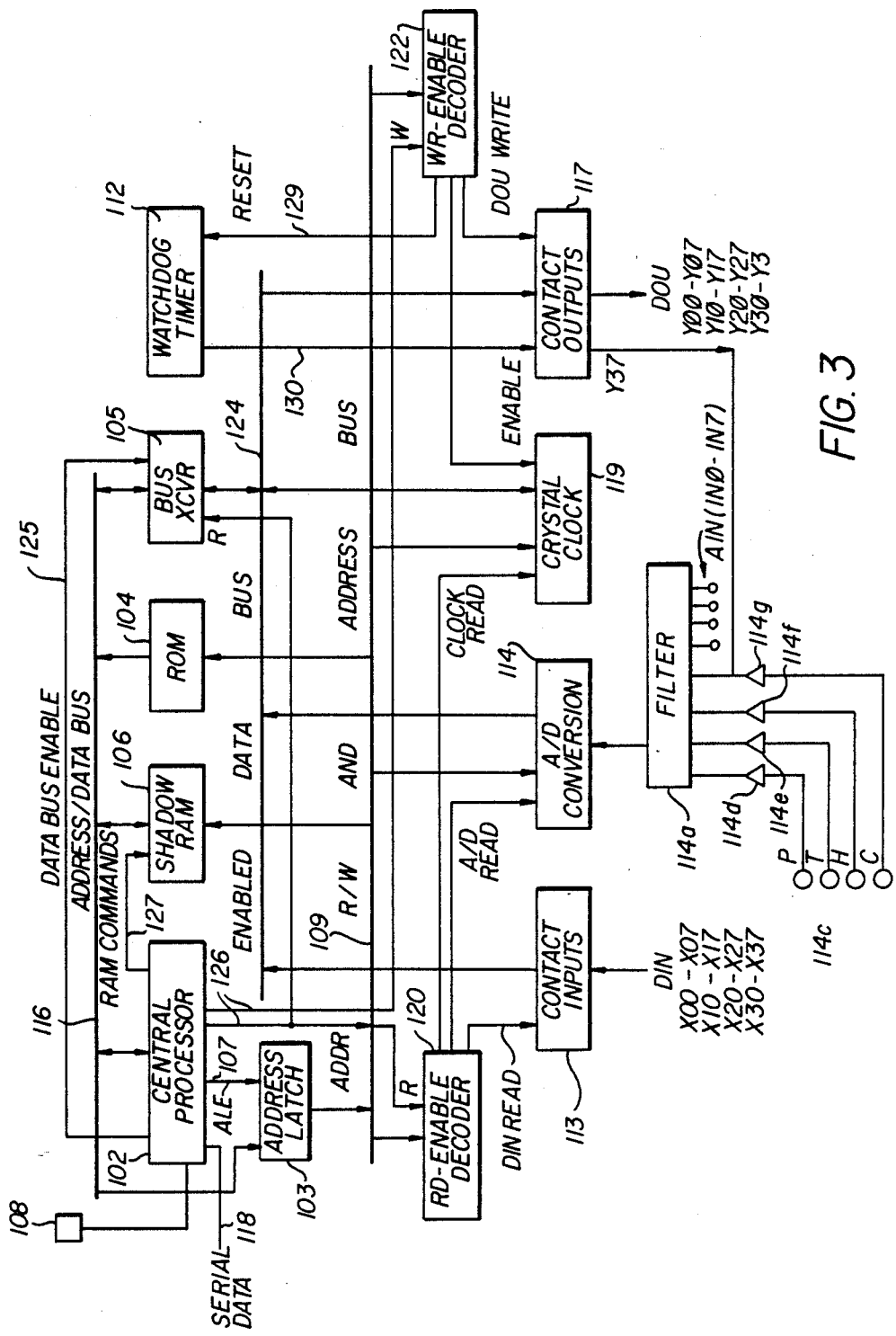
FIG. 3 is a block diagram of the electronic control circuitry of the gas sterilant system.

The overall design of the electronic control circuitry 100 is shown in FIG. 3. The controller is microprocessor controlled, and preferably utilizes a type 8031, 8051 or 8751 microprocessor CPU 102 manufactured by Intel Corp., because of the ability of these processors to perform Boolean arithmetic on bit addressable data. The CPU 102 includes self contained Random Access Memory (RAM) and Read Only Memory (ROM). Furthermore, the controller may include external ROM 104 and a non-volatile Shadow RAM (SRAM) 106 which may be a type X2210 manufactured by XICOR Inc. and which, as discussed heretofore, stores critical data after power-down. The controller also includes a clock crystal 108, input latch 113 receiving Digital INputs (DIN), and A/D Converter 114 and filter 114a for Analog INputs (AIN), an output latch 117 for Digital OUtputs (DOU), and a WatchDog Timer 112 (WDT). The latter timer is arranged to disable all outputs to the valves to their denergized state upon failure of the microprocessor, as described above with reference to FIG. 8. Analog to digital converter 114 and analog filter 114a, convert the analog inputs from the measured gas concentration, temperature, humidity and pressure parameters to digital data.

Central processor 102 is coupled to an address/data bus 116, which also couples RAM 106, ROM 104 and a bus tranceiver 105. An address latch 103 is enabled by a line 107 from the CPU/102, and latches addresses to a further bus 109, the Read/Write and Address Bus. Bus 109 allows the DIN Latch 113, A/D converter 114, a time stamp clock 119 and DOU latch 117 to be addressed at the appropriate times during execution of the sterilization sequence program, i.e., when CPU 102 calls for input data from the various valve limit switches, DIN latch 113 is addressed. At other times the A/D converter 114 or DOU latch 117 will be addressed.

Two decoders, a read enable decoder 120 and a write enable decoder 122 are coupled to bus 109 and allow latches 113 and 117 and A/D converter 114 to be either read from or written to. Appropriate read/write commands are coupled on lines 126 for controlling the decoders.

Furthermore, a data bus 124 is also provided for reading data from or to the input 113 and output 117 latches and A/D converter 114.

Several additional control lines are also employed, including a data bus enable 125 and RAM command lines 127. Line 125 enables bus transceiver 105 only for very short intervals and only during input/output (I/O) subroutines (e.g., subroutines WCO (Write Contact Outputs), RCI (Read Contact Inputs) and RAI (Read Analog Inputs), see appendix), when input and output operations are being performed, e.g., writing output information to DOU latch 117 for controlling the valves. In this way, data on the data bus 124 for actuating the various valves of the valve and pump block cannot be transmitted to the valves except under limited circumstances. This provides an additional degree of system safety. Furthermore, bus transceiver XCVR 105 is bidirectional and the direction of data transfer is controlled by one of the read and write lines, as shown.

RAM command lines 127 issue signals to shadow RAM 106 so that failures can be logged permanently and other critical data can be stored in the event of a power failure.

A reset line 129 is also provided between the Write enable decoder 122 and watchdog timer 112 and an enable line 130 is provided between timer 112 and DOU latch 117. As previously indicated, timer 112 monitors CPU 102 for proper system operation. Normally, CPU 102 constantly resets the watchdog timer via line 129. In the event of a CPU malfunction, the reset signal will fail to appear in time and the timer 112 times out and removes the output enable signal on line 130. The removal of this signal disables all DOU latch 117 outputs, thus preventing valve energization in the event of a CPU failure. Accordingly, a still further degree of safety has been provided in the system described.

Since the elements of the controller are coupled to data buses 116 and 124, as shown in FIG. 3, they have been assigned memory addresses through which they can be accessed by the microprocessor. FIG. 3A shows one arrangement of these addresses, for reference. As indicated above, certain of the devices, such as the SRAM 106 and DOU latch 117, are provided so that the data they contain can only be changed when bits of the microprocessor port lines are sequenced properly. This is a safety feature which prevents some microprocessor failure modes from causing undesired changes in memory contents or valve positions.

Figure 4:
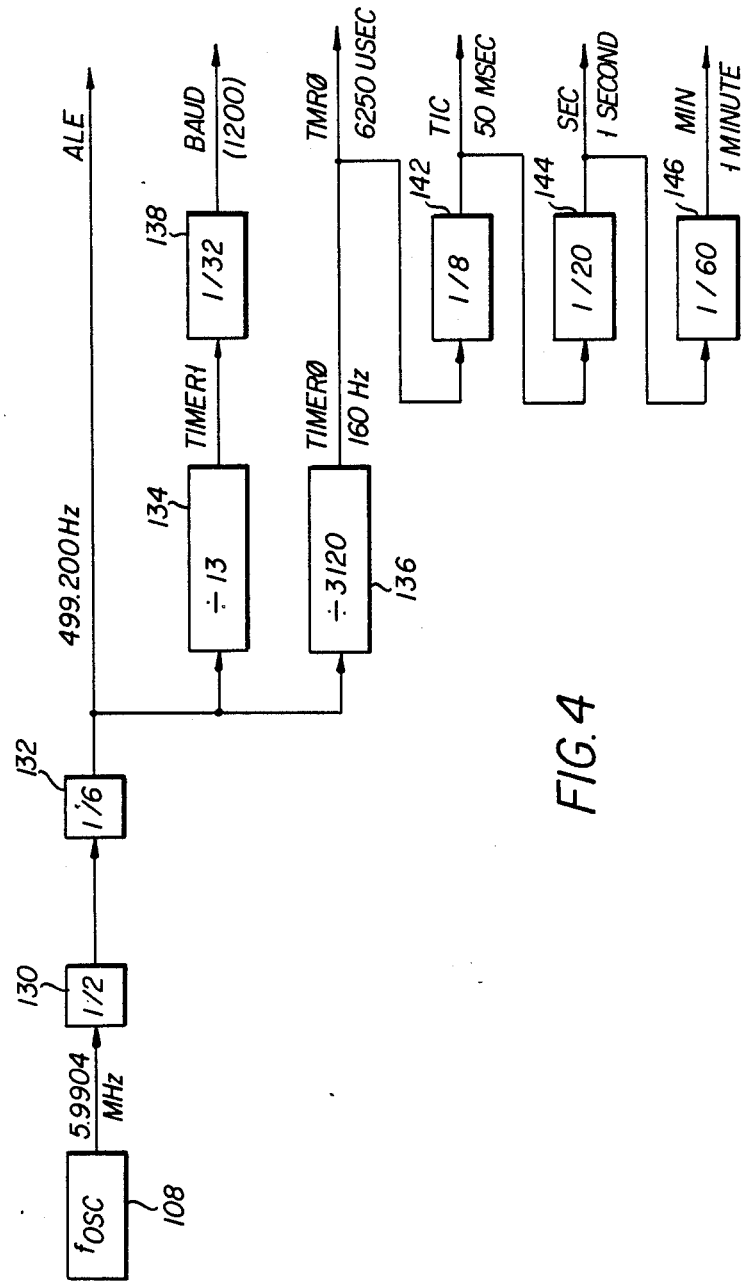
FIG. 4 is a block diagram showing how various system clock frequencies and the system interrupt are derived.

All processor and program timing is derived from the basic clock oscillator 108, which preferably has a frequency of 5.9904 MHz. FIG. 4 illustrates the relationship between the various frequencies used. As indicated in FIG. 3, provision may also be made to add a precision clock 119 to the system, which can be read by way of the data/address bus or via a serial data communications line 118 to provide a clock-calendar for time-stamping the process data.

As shown in FIG. 4, basic processor timing is provided by the CPU internal crystal controlled clock 108. The clock 108 frequency is divided by twelve by CPU internal counter stages 130 and 132 to provide the CPU Address Latch Enable (ALE) signal of 499,200 Hz. The ALE signal is used to strobe address latch 103 so that addresses can be placed on bus 109 and further controls the operation of A/D converter 114.

Signal ALE is also coupled to further internal divider stages 134 and 136. Divider stage 134 provides a signal designated TIMER 1, which is further divided by an internal counter stage 138 into a 1200 bit/sec signal for serial data transfer, which optionally may be provided to transmit system data to remote locations via serial line 118.

Counter stage 136 provides an interrupt, TIMER0. TIMER0 provides a transition every 6250 usecs and allows the main timed function program, TMR0, to read all contact inputs and analog inputs and write all contact outputs every 6250 usecs. The operation of this program and other programs of the operating system will be described in more detail later.

The TIMER0 interrupt is then further divided by program TMR0 software counter stages 142, 144 and 146, to provide the respective program execution signals designated as TIC, SEC and MIN, which occur at period of 50 msecs, 1 sec and 1 min, respectively. These will be discussed in further detail below.

FIG. 3A details the assignment of addresses on address bus 109. As shown, the bus 109 is a 16 bit bus. Internal CPU RAM is assigned address space 00-FF and bits A0 to A7 on the bus 109 identify the RAM locations. Internal ROM is identified by bits $A_0$ to $A_{15}$, with bits $A_{12}$–$A_{15}$ always being 0's, as shown. Addresses from 0000 to 0FFF are used. The other components, external ROM 104, external RAM 106, clock 119, A/D converter 114, DIN latch 113, DOU latch 117 and watchdog timer 112 are assigned the addresses indicated in FIG. 3A. As shown, the DIN and DOU latches each are capable of latching 4 eight bit words, the DIN latches from the various limit switches and other contact inputs and the DOU latches to the various valves, pumps, etc. Digital inputs DIN and digital outputs DOU are each subdivided into four words of 8 bits each, and all eight bits of each group are accessed at one time by the respective addresses indicated in FIG. 3A.

As shown in FIG. 3, the analog pressure, temperature, humidity and chlorine dioxide gas concentration parameters are fed from respective sensors 114c to respective amplifiers 114d, e, f and g. In order to provide an additional degree of system safety when sterilizing chlorine dioxide gas is being evacuated from the sterilizing chamber, it is important that the chlorine dioxide gas concentration levels be accurately measured. Accordingly, amplifier 114g for the gas concentration signal is switched into a high gain mode by a control signal Y37 during the time when the sterilizing chamber is being evacuated. In this way, A/D converter 114 will compare the input concentration analog signal with a greater number of quantizing levels, thus providing a more accurate indication of the actual concentration. At all other times, amplifier 114g will remain in a low gain mode. For example, when chlorine dioxide levels are being measured in the chamber for purposes of determining an adequate sterilizing concentration, much higher concentration levels are being measured, and accordingly, A/D converter 114 provides an accurate digital signal corresponding to the analog concentration level. Therefore, amplifier 114g can remain in a low gain mode. Amplifier 114g may be switched to a high gain mode by signal Y37 changing from a "0" to a "1".

The system data-base may be thought of as being divided into external and internal sections. The external data-base contains the Contact inputs (CCI), which are comprised of the digital inputs DIN; the Contact Outputs (CCO), which comprise the digital outputs DOU; and the Analog INputs (AIN). Images of the external data-base are maintained in an internal data base comprising locations in internal RAM by subroutines of the TIMER0 program (TMR0), which is invoked every 6250 microseconds. That is, every 6250 microseconds, all contact inputs and analog measurements are read and stored in the controller internal data-base and images of the contact outputs loaded in the DOU latch. With reference to FIG. 12, which is a memory map for the internal data RAM of CPU 102, images of the contact inputs are stored as the variables CCI0 through CCI3, and the filtered analog inputs are stored as the variables ADI0 through ADI7. The contact outputs are stored as variables CCO0–CCO3. Programs using the input data retrieve it only from these locations, and not from the input devices directly. Hence, the programs only operate on images of the inputs and outputs. In addition, the internal database includes a number of register banks, RB0–RB3. In RB0, a number of timers 205 are provided including a 50 msec timer TICK (50 msec), a second timer TSEC (1 sec) and a minute timer TMIN (1 min). These timers provide timed function intervals for scheduling functions implemented at those intervals by the system main dispatching program. The TICK timer times out after 50 msecs and sets a flag TICF in STATUS register 204 to be used by the main dispatching program to initiate all 50 msec timed functions, including a number of timers 200 in register bank RB3 which are invoked every 50 msecs, TTMx. These timers are preferably invoked for monitoring timeout conditions for the system valves, for example.

The TSEC timer similarly times out after 1 sec and sets a flag (SECF) in STATUS register 204, to be used by the main dispatching program to initiate all 1 second timed functions, including a number of timers 200 in RB3 which are invoked every second, STMx. Similarly, the TMIN timer times out after a minute and sets a flag (MINF) in STATUS register 204 to be used by the main dispatching program to initiate the 1 minute timed functions, including a number of timers 200 in RB3 which are invoked every minute, MTMx. The data memory also includes registers in RB2 for keeping track of the current state and ABORT state used by the sequence program. Also included are the sequence status register 204, TCEN and TCFL registers 207 and 208, already discussed, for the timers, and a control register CTRL for enabling a control calculation to open or close a valve. 4 bits of the control register, as shown, are used for controlling the four control loops of the system, corresponding to the measured temperature, humidity, pressure and gas concentration parameters. An array of bit masks 260 is provided in the internal data-base to permit "don't care" conditions when comparing contact input and output status. Further descriptions of the data elements are found in the controller program source listing in the appendix to this specification.

More particularly, internal RAM of CPU 102 may be organized as follows. The 256 (FF) memory locations are organized into 50 msec, one sec and one minute timers in the timed function registers (memory locations 00 to 07); optional communications program registers (memory locations 08 to 0F) for controlling a receive buffer RBUF and transmit buffer TBUF; main dispatching program registers (memory locations 10 to 17); timers 200 which are implemented at 50 msec, one second and one minute intervals by timers 205 (18 to 1D); (counters 1E and 1F); a status byte 204 (20); a control byte 206 (21); a timer enable byte TCEN (22); a timer flag byte TCFL (23); a series of masks 260 for the inputs; (24–27); the contact output images CCO0–CCO3 (28–2B); contact input images CCI0 CCI3 (2C-2F); analog inputs ADI0–ADI7 (30–37); and set points for the measured process variables, such as temperature, pressure, concentration and humidity (38–3B). The remainder of the internal RAM is assigned to the communications buffers (40 to 5F), the system stack (60 to 7F) and internal microprocessor registers and storage (80 to FF), the use of which is known to those skilled in the art. Refer to Microcontroller User's Manual, published by Intel Corp., May 1982, document No. 210359-001. Although the entire system program is contained in internal ROM of the CPU 102, an external ROM may also be provided so as to allow additional programming capabilities. Alongside FIG. 12, the contents of the STATUS, CTRL, TCEN and TCFL registers by bit are shown.

State Sequence

The progress of the sterilization cycle can be determined from the PROGRESS lights on the display panel, shown in FIG. 5. During a normal cycle the failure lights should never be on. Whether normal or aborted, both cycle and failure data will be maintained in a non-volatile random access memory or shadow RAM (SRAM). For example, after a designated number of cycles, e.g. three cycles, the gas cartridges will be discharged and must be replaced. The data concerning the number of cycles in which a cartridge has been used is stored in this memory. Also, after a predetermined number of cycles, or repeated failures, the system will be disabled until maintenance has been performed. This is a safety feature which cannot be bypassed in the field, and this data is also stored in the non-volatile memory.

As discussed, FIG. 6 is a state diagram which defines the operation of the sequencing program of the sterilant system. FIG. 7 identifies the condition of the components identified in FIG. 2 as well as the display lamps shown in FIG. 5 for the various process states. The operation of the system may now be described in further detail.

The system always begins in an initialization state, state 0. During this state, all output lines of the microprocessor in control circuitry 100 are set so as to initially deenergize all valves in the valve and pump block 20. After a short time delay, valve V7 is opened to allow air into the chamber, as shown by a "1" appearing opposite VV07 for state 0 in FIG. 7. Furthermore, during this state, the control circuitry 100 stores in memory the state of all output ports of the microprocessor.

In states 0 and 1, the door to the sterilizing chamber 10 is in its open position. Once the door is closed, state 2 is entered. As indicated in FIG. 6, this means that the system is ready to begin its cycle. As further indicated in FIG. 7, in state 2, valves V1–V6 are closed, valve V7 remains open and valve V8 is closed. Display lights LT1–LT6 are off, light LT11 (READY FOR CYCLE) is on and lights LT12–LT17 are off. The corresponding limit switches (LS) are in a position determined by the condition of the associated valve, e.g., for valve V2, which is closed, limit switch LS2o is open while limit switch LS2c is made. As indicated above, two limit switches are provided on each valve, one for the open position and one for the closed position, in order to insure the safety of the system. Both limit switches must be in their proper position, otherwise a failure will occur.

When the door to the chamber 10 is open, the system is in state 1, once the initialization state has been passed. Accordingly, only LT1 is on and the other lights are off, as shown in FIG. 7.

Assuming the chamber door has been closed and the system is in state 2, if the START CYCLE switch S1 is pressed, the system moves to state 3. At this point valve V7 closes, as indicated by the "0" appearing in the column for state 3 in FIG. 6 and light LT12, CYCLE IN PROGRESS, turns on. As indicated in FIG. 2, valve V7 vents the chamber 10 via a filter 13 to the atmosphere when open. Thus, the flow of filtered external air into the chamber is stopped when valve V7 closes.

If the door is opened in state 2, an immediate return to state 1 is made.

Once in state 3, and, if V7 is closed, as indicated by the closed state of limit switch LS7c and open state of limit switch LS7o, state 4 will be entered. If valve V7 does not close within a certain time, as determined by a timeout implemented by one of the TIC timers TTMx in RB3 of the data memory, state 29, ABORT-1 will be entered. Furthermore, if an alarm condition occurs, such as the opening of a valve which should be closed, an alarm condition will be generated and the point of failure indicated on the display panel, indicating to the operator that a malfunction has occurred.

Once in state 3, if the chamber door is opened, the cycle will be aborted, as shown in FIG. 6.

Assuming V7 has closed and state 4 has been entered, the chamber heater HT01 is turned on, as indicated by the "1" in the column for state 4 opposite HT01. If the temperature within the chamber increases to a sufficient level within a time-out period, state 5 can be entered. If not, ABORT-1, state 29, is entered and a return to state 2 is thereafter made when switch S2 is depressed. A safe operating temperature is reached when temperature switch T1 (FIG. 2) is actuated by the temperature of the atmosphere in the chamber reaching the desired temperature. After this occurs, the temperature in the chamber is controlled by turning the heater on and off as required during the cycle, as indicated by the notation "C" in the columns of FIG. 7 opposite "HT01".

Once state 5 is entered, valve V1 is opened, in preparation for starting vacuum pump P1 so that the atmospheric contents of chamber 10 can be evacuated. Again, if valve V1 does not open within a timeout period, ABORT-1, state 29 is entered.

State 6 is entered when vacuum valve V1 opens within the timeout interval. At this point, the vacuum pump P1 is started and light LT13 indicates that evacuation is in process. A timer is started which determines the length of time that the pump remains on.

Once in state 6, the chamber door 11 can no longer be opened, because, at this point in the cycle, the chamber is under a vacuum.

In state 6, the pressure in the chamber is checked to determine if it has been reduced sufficiently so that it is less than or equal to a nominal value, defined as PEVAC. If the pressure is less than PEVAC, then state 7 is entered and valve V1 is closed.

Should the pressure within the chamber be greater than PEVAC after the evacuation time has passed, indicating a less than adequate vacuum level, state 29 is entered. Similarly, if valve V1 does not close within a specified time, state 29 is entered from state 7.

After the valve V1 has been closed in state 7, a leak-hold test is commenced in state 8. If the pressure after a leak-hold time is less than a nominal value PLEAK, state 9 is entered. If not, abort state 29 is entered.

In state 9, water vapor is allowed to enter the chamber, i.e., valve V6 is placed in a controlled open state, as indicated by "C" in FIG. 7, and a determination is made whether the humidity has reached a specified level in a certain time. Should a nominal humidity HNOM not be reached within the specified time, state 30, ABORT-2, will be entered. Since evacuation has been completed, light LT13 is turned off and light LT14, which indicates a FILL IN PROGRESS, is turned on. By FILL is meant the supply of non-sterilizing gases into the chamber, e.g., steam and nitrogen gas. At this point, the system enters a new point in the state diagram wherein malfunctions allow the system to return to a different abort state, state 30. The state of the various valves and displays for ABORT-2 (state 30) is indicated in FIG. 7.

In state 9, the humidity timer times out. If the humidity level is greater than a nominal value HNOM, state 10 is entered. Otherwise, state 30 is entered and the cycle is aborted.

In state 10, a humidity hold test is performed wherein the humidity level is monitored for a predetermined time period. If the humidity level is not maintained for the predetermined time, state 30 is entered. Otherwise, state 11 is entered. Valves V2 and V8 are opened and valve V5, along with valve V6, is then controlled on.

Valve V5 allows nitrogen to enter the system. At this point, even though valve V2 is open, chlorine dioxide cannot enter the chamber because valves V4 and V4A, which are controlled together, are closed.

In state 11, valve V2 is checked to determine that it has opened. If it has not opened withing a specified time, state 30 is entered. If valve V2 has opened in time, state 12 is entered, and valves V4 and V4A are controlled on, allowing chlorine dioxide to enter the chamber. A timer is started during which time the chlorine dioxide gas concentration levels in the chamber are measured. As explained previously, chlorine dioxide may be generated by the reaction of two components, $Cl_2$ gas and sodium chlorite, $Na_2ClO_3$, on site. Chlorine gas is contained in a canister which can be coupled to the system via a connecting port, as known in the art. A container of sodium chlorite is coupled into the system between valve V2 and valve V4, as shown in FIG. 2. In state 12, LT14 is turned off and LT15, STERILIZATION IN PROGRESS, is turned on.

Once the gas concentration measured in state 12 has reached a concentration greater than or equal to a nominal concentration CNOM within a preset time period, state 13 is entered. An acceptable sterilizing gas concentration might be, e.g., 1.0 mg/L to about 300 mg/L. Otherwise a new abort state, ABORT-3, state 31, is entered. This new abort state is necessary because new conditions are now present in the sterilization chamber, since sterilizing chlorine dioxide gas is now present in the chamber. This requires a different set of procedures to be followed in the event of a failure, and accordingly, a new abort state is provided.

In state 13, a gas-hold test is commenced. If the gas concentration is greater than or equal to CNOM for a predetermined time period GTMR, state 14 is entered. Otherwise, state 31 is entered and the cycle is aborted.

In state 14, the temperature in the chamber is measured. If it is greater than a minimum temperature TMIN but not higher than a maximum temperature TMAX, state 15 is entered and a sterilization timer is started. If the temperature is not adequate, state 31 is entered and an abort occurs. A typical operating temperature is approximately 30° C.

During state 15, sterilization is in progress. Valve V6, for humidity control, is still controlled open, and valves V4 and V4A are also controlled open. Should an alarm condition occur, e.g., if any condition changes, i.e., a valve does not remain in its proper state, state 31 is entered. State 16 is entered only after a sterilization time STMR has elapsed, which typically might be several hours.

In state 16, valves V4, V4A and V6 are closed (if they do not close in the required timeout period, state 31 is entered), valve V3 is in a controlled state and valve V8 is still open. In state 17, light LT15 is turned off and light LT16 is turned on. Light LT15 is turned off when the sterilization timer has timed out and valves V4, V4A have closed. Light LT16 indicates that a purge is in progress. During state 17, the gases in the chamber are removed via valves V3 and V8 and detoxifier 22, labelled DUMP 22 in FIG. 2, which converts the chlorine dioxide into a harmless substance. The detoxification may be accomplished as explained in the above copending patent application Ser. No. 601,443, by passing the evacuated chlorine dioxide gas through a reducing agent, e.g., sodium thiosulfate. The detoxified gases are removed via valve V8 by vacuum pump P1. Should valves V3 and V8 fail to open within a timeout period, ABORT-3, state 31, is entered. During state 17, an evacuation timer is started which controls the amount of time during which chamber 10 is evacuated. State 18 is entered only if both valves V3 and V8 have opened in a predetermined time interval.

In state 18, once the evacuation timer has timed out past a time ETMR, state 19 is entered and valves V3 and V8 are closed. State 20 is entered when valves V3 and V8 close.

As shown in FIG. 6, should an alarm condition occur or should valves V3 or V8 fail to close within a specific time, state 31 is entered.

In state 20, valve V5 is in a controlled state. This allows nitrogen gas to enter the system as required and also prepares the system for the removal of any remaining sterilizing gases behind valve V2 via detoxifier 22 once valve V3 is reopened in state 22. In state 20, the pressure is checked. If it is greater than a maximum pressure PMAX, valve V5 is closed in state 21, turning off the nitrogen supply. If the pressure is less than PMAX, a new abort state, ABORT-4, state 32, is entered.

In state 21, valve V5 is checked to determine that it has closed within a prescribed timeout period. If it has not, state 32 is entered and the cycle is aborted. In state 22, the remaining sterilizing gases in the system are detoxified via detoxifier 22 and reopened valves V3 and V8 and the gases removed. Once valves V3 and V8 have opened for a sufficient period of time, state 23 is entered but only if valves V3 and V8 have opened. In state 23, another timer, denoted the DESORB timer, is activated. This allows sterilizing gases which have been absorbed into the materials in the chamber to be removed or desorbed over a time period DTMR.

Should valves V3 and V8 fail to open, ABORT-5, state 33, is entered. In this circumstance, the operator will be instructed to manually activate valves V9 and-/or V10 so that sterilizing gas can be removed from the system. The manually operable nature of valves V9 and V10 is indicated in FIG. 2 by a T above the valve symbols. If valves V9 and V10 are manually opened, state 33, ABORT-5 will automatically be entered.

If state 23 is successfully reached and the DESORB timer times out after a time DTMR, state 24 will be entered. At this point, valves V2, V3 and V8 are closed and a check is made to determine that these valves are closed. Then, state 25 is entered, during which a low-gas-hold test is performed. If the gas concentration is less than or equal to an acceptable value CMIN within a time period GHTM, state 26 is entered. An acceptable level of safety might be, for example, less than 0.5 ppm of chlorine dioxide. Otherwise, a dummy state 35 is entered, before a return is made to state 20 by operation of switch S2. This provides a delay time in which to open valves.

In state 25, the gain of amplifier 14g (See FIG. 3) is changed so that the amplifier is placed in a high gain mode during the measurement of chlorine dioxide gas concentration levels during evacuation. This is indicated by the "1" in state 25 opposite GC1 (gain change control). This provides more accurate measurement of concentration levels during evacuation, providing an extra degree of system safety, as discussed previously. Also, in state 25, a counter CNT (see RB3 of FIG. 12) is decremented. This counter forces the system to cycle through states 25, 20, 21, 22, 23 and 24 via state 35 for a specified number of times determined by the initial count in the counter CNT0. Accordingly, state 35 will be entered whenever the concentration level CMIN has not been reached within time GHTM or if the counter CNT has not reached 0. State 26 will be entered from state 25 when both the concentration is less than CMIN and CNT0 is 0. This is provided to insure system safety in the event the concentration sensor in the sterilizing chamber should fail. By going through a number of cycles via state 35, the gas concentration will be decreased, thus insuring that, even if the concentration sensor indicates the gas concentration levels are below CMIN, the system will automatically cycle through a number of times necessary to reduce the concentration to acceptable safety levels. This is important, because if the concentration sensor failed and this additional safety feature was not provided, the system might indicate that the gas concentration level was within acceptable levels of safety although it actually might not be.

In state 26, a counter is checked which is incremented each time the system cycles at least to step 26. If, e.g., the count is less than 3, a jump is made to state 28. If greater than or equal to 3, state 27 is entered. In state 28, valve V5 is controlled on, and the count is then incremented. This allows nitrogen gas to enter the chamber.

If the cycle counter is greater than or equal to 3, then state 27 is entered directly. In state 27, valves V2, V3, V4 and V8 are opened, and all remaining gas is dumped from the system and the $Cl_2$ gas in the cartridge is also dumped. Once sufficient time has elapsed, i.e., the Dump Hold time DHTM has elapsed, state 28 is entered. From state 28, the system enters state 37, during which the pressure in the chamber is monitored until it is within 5% of atmospheric pressure. At this point light LT17, REMOVE LOAD, is turned on. At this point, state 38 is entered, light LT11 is turned on and actuation of switch S2 enables a return to state 1. The operator will be notified to replace the gas cartridge if the system has gone through state 27.

As indicated in FIGS. 6 and 7, after ABORT states 29 and 30 are entered, a return is made to state 2 after switch S2 is depressed and state 2 conditions are set.

In ABORT state 31 a return is made to state 20 and state 20 conditions are set once switch S2 is depressed. In ABORT state 32, return is made to state 19, and state 19 conditions are set. In ABORT states 33, 34, and 36, return is made to states 23, 25 and 37, respectively. If state 38 is reached, the operator receives an indication that the cycle is complete and light LT17 is turned on. To allow the chamber door to be opened, switch S2 is actuated, and state 1 is entered. If any ABORT state is reached, the appropriate failure light is illuminated. When a return is made to states 20, 23, or 26 from an ABORT state, the system then proceeds to cycle through the states which normally follow in the sequence.

General Software Functions

The sequencing program has already been described. Generally, software for the sterilization system controller is interrupt driven. Until an interrupt occurs a background task is always running via the main dispatching program. Upon interrupt, from any of several possible event sources, software control is passed to the appropriate interrupt handling program. This is illustrated in FIG. 9.

Figure 9:
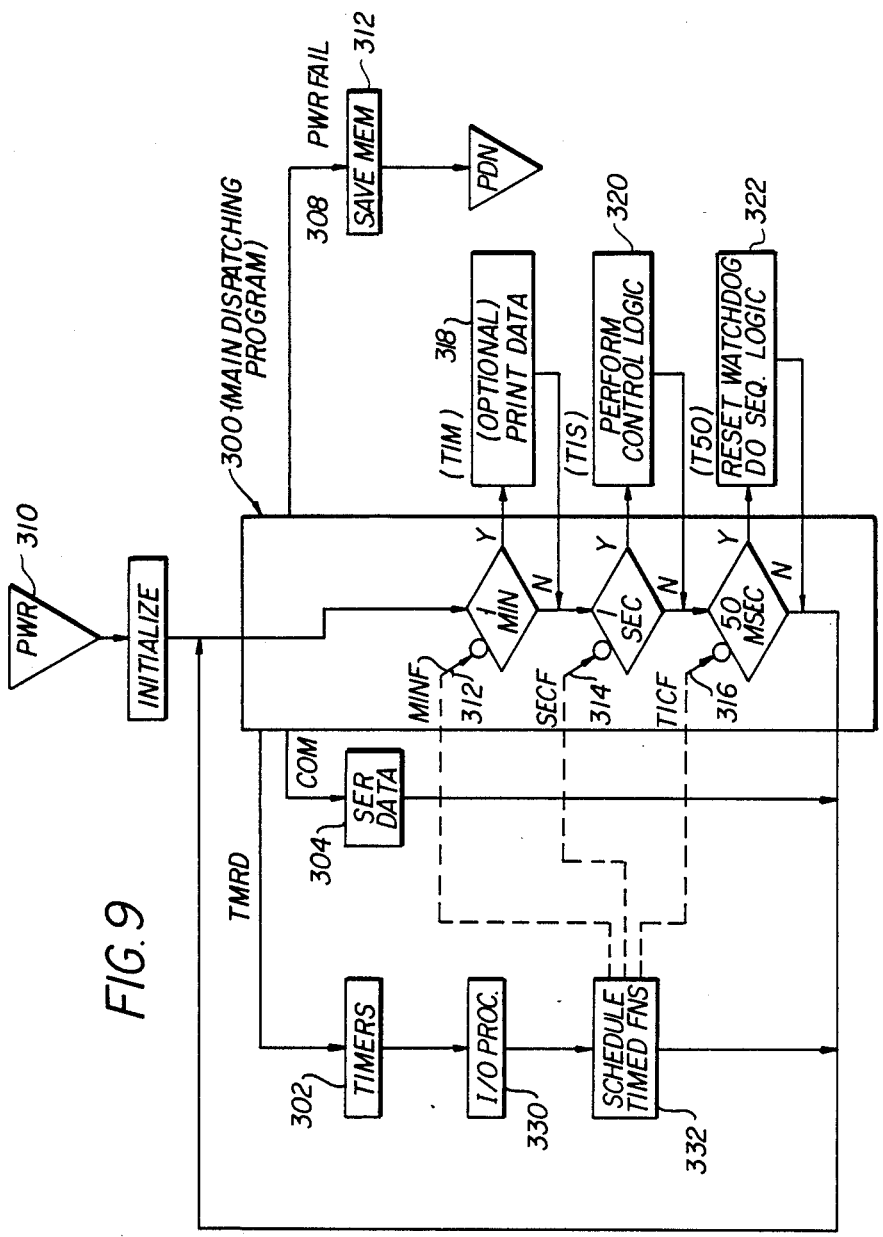
FIG. 9 is a functional flow diagram for the software resident in the memory of the electronic controller of the gas sterilant system according to the present invention.

In FIG. 9, the main dispatching program 300 is shown. This program can also be found under this heading in the program listing attached hereto. Essentially, this program monitors for the occurrence of a timer flag indicating 50 msec, 1 sec or 1 minute functions must be performed. These flags are stored in the status register (STAT) 204 of FIG. 12. When a flag occurs, the program 300 jumps to the appropriate timer program 318, 320 or 322. The timer programs are performed on a priority basis such that one minute functions are performed first and 50 msec (T50) functions last.

There are four sources of interrupting events: power-up, timer, communications, and power-down. Power-up, power-down and communications are external hardware interrupts, while the timer interrupt, TMR0, is an internal hardware interrupt under program control. Except for power-up, each interrupt handling program saves the running processor context in the CPU stack before starting its task function, and the context is restored before resumption of the interrupted program. The timer interrupt handler (TMR0) sequences all other non-interrupt programming functions. As discussed, it accomplishes this by passing one or more flags (MINF 312, SECF 314, TICF 316), signifying which of the timed tasks is to run, through the STATUS register 204 of FIG. 12. The main dispatching program 300 tests the flags and will cause the selected functions to be executed as shown by 318-322. This method permits further interrupt action while lower priority functions are being completed. Some of the functions performed at one minute, one second and 50 msec (TIC) intervals are as indicated in FIG. 9 at 318, 320 and 322, respectively. The descriptions to follow will explain the tasks to be performed under each category of interrupt event in greater detail.

Main Dispatching Program

Essentially, the main dispatching program looks for timer flags and when one is found, calls the appropriate subroutine. See FIG. 9. The main dispatching program may be found in the attached program listing.

Power Up

Upon power-up as shown at 310, the processor stack, register bank, and other functions must be initialized. This interrupt function does not require saving of the processor context. Instead, previous process information will be read from the electrically reprogrammable memory SRAM 106, the clock 119 is reset and the process will resume from whichever state has been prescribed. The watchdog timer will be reset, and control will then pass back to the main dispatching program 300.

The power-up routine is found in the program listing under the program title INIT.

Power Fail

A power fail program is preferably implemented. One embodiment for this program, as shown in FIG. 9, stores critical memory contents at 312 into the SRAM 106, where the data will be preserved until power is restored. The power-fail interrupt may be designed to occur whenever the 5 volt logic line drops below 4.55 volts, and recovery to 4.75 volts may be utilized for power-up. The power fail program can be found in the attached program listing.

Communications

A communications feature (COM) may optionally be provided in the system according to the invention. The communications program is activated every time a character is removed from a serial output buffer or enters a serial input buffer. The function of this program is to feed characters to the transmit buffer as they are sent and to remove characters from the receive buffer as they are received. Two FIFO queues may be provided to hold the input and output data streams. The communications program tests the input and output data streams for the presence of termination or control characters. Flags are set in the event of termination characters. Programs, well known in the art, may be provided for processing control characters for typical serial interface devices connected to the control circuitry. For example, it may be desirable to transmit information for recording purposes over telephone lines to a printer or display device. Other programs, known in the art, can be employed to handle the standard modem control functions, e.g., RS232C commands. Hardware I/O lines may be provided for the necessary modem control signals. The communications program saves and restores the processor context.

Timed Functions

Figure 24:
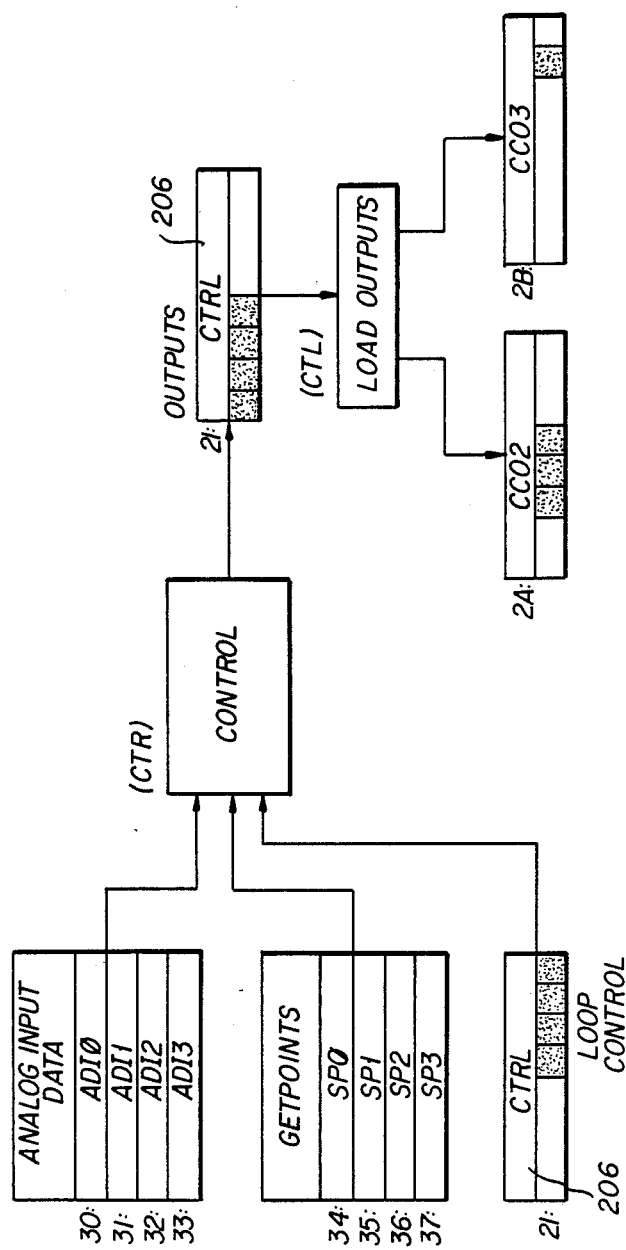
FIG. 24 is a flowchart for a program implemented in the control unit for controlling the system outputs.

Timed functions in the controller occur on four levels as follows: functions triggered by the TIMER0 timer (every 6250 microseconds), functions initiated every 50 milliseconds (TICS), functions started every second, and functions which run every minute. Data is exchanged between these levels through defined data areas in the microprocessor data-base, as indicated more clearly in FIG. 10. The TMR0 program also accesses the input and output devices connected to the controller. The control function (CTR), which is activated every second, transmits valve commands to the upper four bits of the CTRL register when enabled by the lower four bits of the CTRL register on a bit by bit basis, as shown in FIG. 24.

As shown in FIG. 4, timer interrupts (TMR0) occur at intervals of 6250 microseconds (6.25 milliseconds). At each interrupt, the TMR0 program is entered, and all timed functions are scheduled. As the basic cycle time of the processor is approximately two microseconds, 3120 instruction cycles will elapse before the next such interrupt. Some of this time is used at each timer interrupt to perform data gathering and interlock functions, e.g. the analog inputs and data inputs are read and stored in CPU internal RAM. This is indicated at 330 in FIG. 9. Immediately following a timer interrupt the processor context will be saved in the appropriate registers. The interrupting timer, TIMER0, will then be reset and restarted. Program functions which are to occur at intervals of 50 msec., 1 sec., and 1 min. will be scheduled as shown at 332, by passing flags, as discussed, whenever the respective time interval has elapsed. Data inputs, status checks, and outputs are performed next. Finally, the previous program context is restored, and an interrupt return is executed. If any timed events are to occur, they will be performed in sequence by the main dispatching program. Otherwise the main disptaching program will be resumed.

The basic timer program, which is executed for each timer, is shown in the flowchart of FIG. 22. As shown, the timer is first decremented and a check is made to determine if the timer has timed out, i.e., reached a count of 0. If so, the corresponding timer flag is set in TCFL register 208 shown in FIG. 12. If not, the corresponding flag is cleared. Then the program is executed for the next timer, and once all timers have been completed, a return is then made to the main dispatching program.

Figure 23:
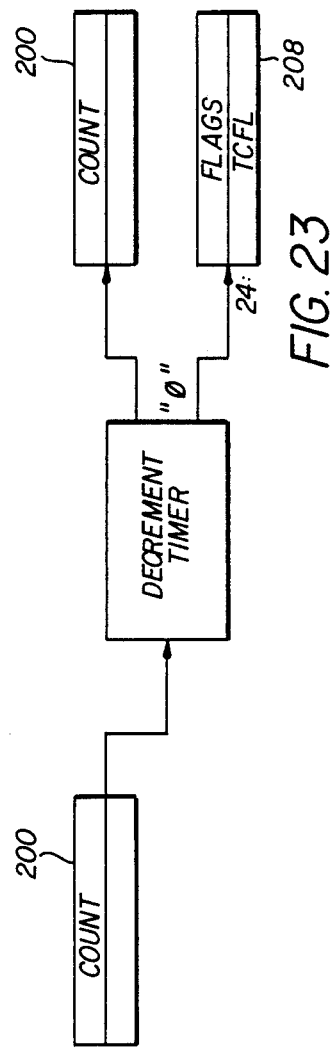
FIG. 23 is a flowchart for part of the program of FIG. 22.

The decrement timer function is shown in FIG. 23. As shown, when a timer is decremented, a flag is set in the TCFL register if the time has timed out, and the current count is then stored in the appropriate timer register 200.

1. TIMER0 Timer (TMR0)

Figure 10:
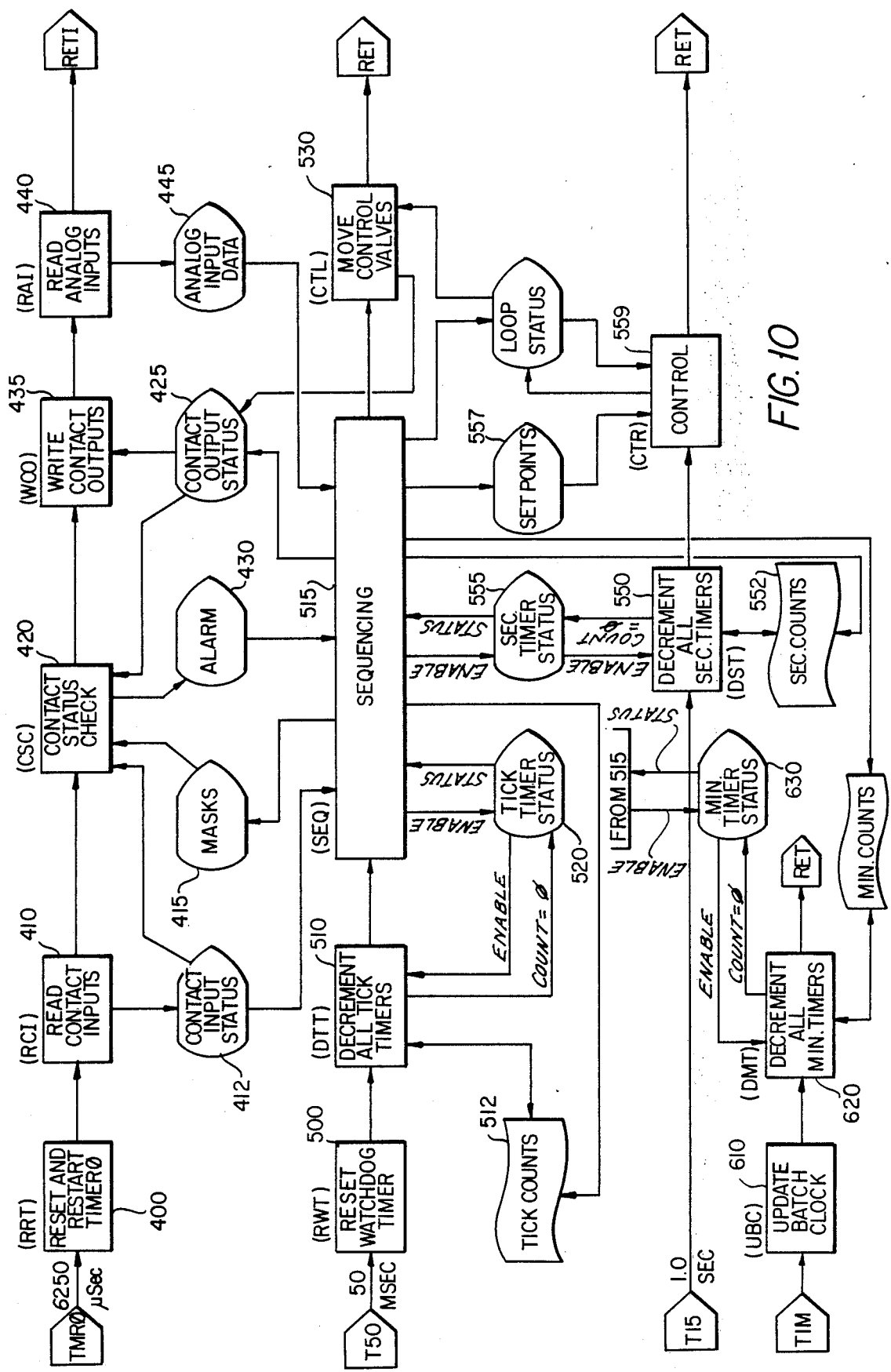
FIG. 10 is a flow diagram for timed functions of the software for the gas sterilant system.
Figure 17:
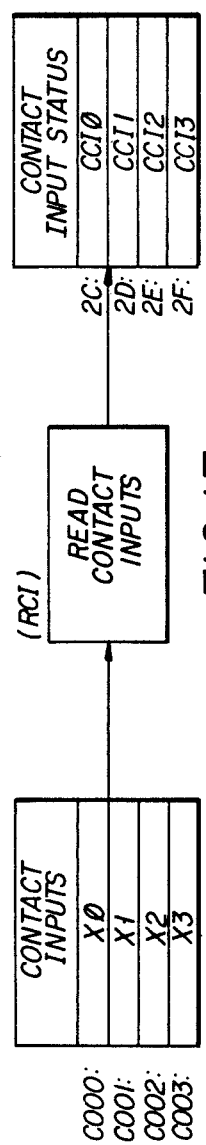
FIG. 17 is a flowchart for a program implemented in the control unit for reading in input data from the system according to the invention.

The lowest level timed function, occurring every 6250 microseconds, is initiated by the interrupt TIMER0. This is indicated in the uppermost portion of FIG. 10, which is a flowchart for the various timed functions. After saving the processor context, the first function of the TMR0 interrupt program is to reset and restart the timer as indicated at 400. This is performed by a subroutine RRT. In FIG. 10, the corresponding program for implementing the desired function is indicated above the flowchart symbol, and can be found in the listing in the appendix. The TMR0 program is a time-critical function. Once the timer has been restarted, all of the contact inputs to the controller are read into their corresponding memory images, CCI0-CCI3 as shown at 410 and 412. These images reside in a portion of the microcomputer memory which is bit addressable. This greatly facilitates logical processing. The subroutine for implementing this function is shown in FIG. 17 and is also shown in the attached program listing as subroutine RCI. The contact output information is also located in this memory, at CCO0-CCO3 and is indicated in FIG. 10 at 425. The interrupt program next performs a masked comparison of the contact input and output status bits, using bit masks 415 also stored in this memory area. This is shown at 420. If any bits do not match their corresponding desired outputs, when masked for "don't care" conditions, an alarm condition is set by setting a bit in the STATUS register 204 (FIG. 12), as shown at 430.

Timeout alarms are also implemented by the TMR0 program. A subroutine CSC2, as shown in FIG. 18 and the attached program listing, shows how timeouts are determined. When a timer times out, e.g., a timer for determining whether a valve has closed or opened in time, a flag will be set in the timer flag register TCFL. If the setting of the flag requires an abort upon failure, e.g., if the failure of a valve to close in time is to cause an abort condition, then a flag must be set in the timer enable register TCEN. This informs the timeout alarm program that an alarm condition should be set, which will cause the alarm condition to be loaded into the STATUS register. This will cause transfer to an ABORT state by the sequencing program.

Figure 11:
FIG. 11 is a flow diagram for one of the timed functions of the software for the gas sterilant system.

Next the current contact output status is loaded from its memory image into the output contact latch by program WCO, as shown at 435. Finally, as shown at 440 and 445, the current analog input data 445 is read (RAI), exponentially filtered (FILTER), and stored in the correct memory locations outside the bit addressable space. See FIG. 21. Eight timer interrupts take 50 milliseconds. Thus, a well-filtered analog input scan of all eight analog inputs (only four need be used for the four control loops corresponding to gas concentration, pressure, temperature and humidity) will be available each time the 50-millisecond program is entered. Therefore, every 50 msecs, the RAI program obtains 64 input samples, 8 for each channel, the eight samples for each channel then being averaged to obtain a single analog value for each channel. A return is then made to the main dispatching program. The TIMER0 program is summarized in the flowchart of FIG. 11.

2. TIC Timer (T50)

Figure 13:
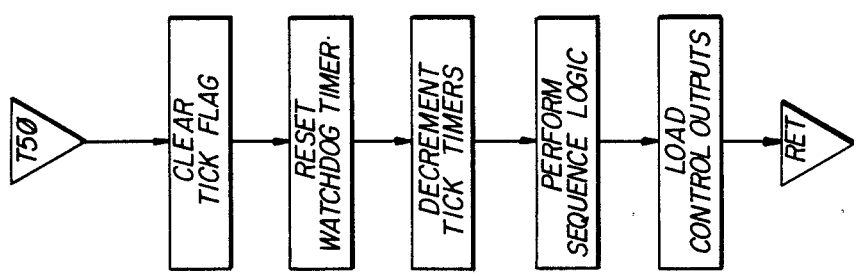
FIG. 13 is a flowchart for another of the timed functions of the software of the electronic control circuitry for the gas sterilant system according to the present invention.

The TIC functions are those which are performed every 50 milliseconds, and include the performance of the sequencing (SEQ) program. The first function performed is that of resetting the watchdog timer as shown at 500, because if this timer is not reset in time, all valve outputs will be disabled as described with reference to FIG. 8. Next, all tick timers (TTM) are decremented at 510, their counts stored at 512, and their corresponding status flags set or cleared at 520 in register TCFL 208 of FIG. 12. The setting of the timeout flags in the TCFL register 208 (See FIG. 12) also requires that the status of a corresponding bit be determined in the Timer Counter Enable Register (TCEN) 207 by the sequencing program, as shown. In this way, if the corresponding TCEN bit is not set, this informs the controller not to enter an ABORT state when the timer flag comes on. For example, when the sterilization timer times out (approximately after 4 hours), an ABORT state should not be entered. For valve time-outs however, it is desired to abort if the timer times out and the valve has not opened or closed in time, and accordingly, the corresponding TCEN bit will be set by the sequencing program, thus allowing an alarm to be generated. If the valve closes in time, its corresponding TCEN bit will be disabled, and no alarm will be generated. Once the TICK timers have been decremented, the main sequencing logic 515 (SEQ), which controls the progression from one state to the next described hereinabove, is performed until it cannot progress further, due to a hold for a specified status condition not yet present. Then, the outputs are loaded into the contact output image in memory (CCO) at 530, e.g., the output data for the appropriate valves or heater to be controlled are stored in memory. Then, the TMR0 program subroutine WCO will write the output images to the controlled devices on its next pass. The TIC function program is sumarized in the flowchart of FIG. 13.

3. Second Timer (T1S)

Every second all one-second timers are decremented at step 550, the count stored at 552, and their corresponding status bits set or cleared (555). This includes the setting of flag bits (TCFL) and appropriate Timer Counter Enable bits (TCEN) depending on whether an ABORT is to occur at the occurrence of the timer flag. Finally, the control program 559 (CTR), accepting setpoints (557) from the sequencing program 515, loads the new output status for the controlled devices into the CONTROL register for subsequent loading into the contact output registers of internal RAM. During the next pass through the TMR0 program, these outputs are fed to the controled devices. As shown in FIG. 8, the timed functions occur in the order MIN, SEC and TICK. A flowchart for the one second program, T1S, is shown in FIG. 14.

Figure 14:
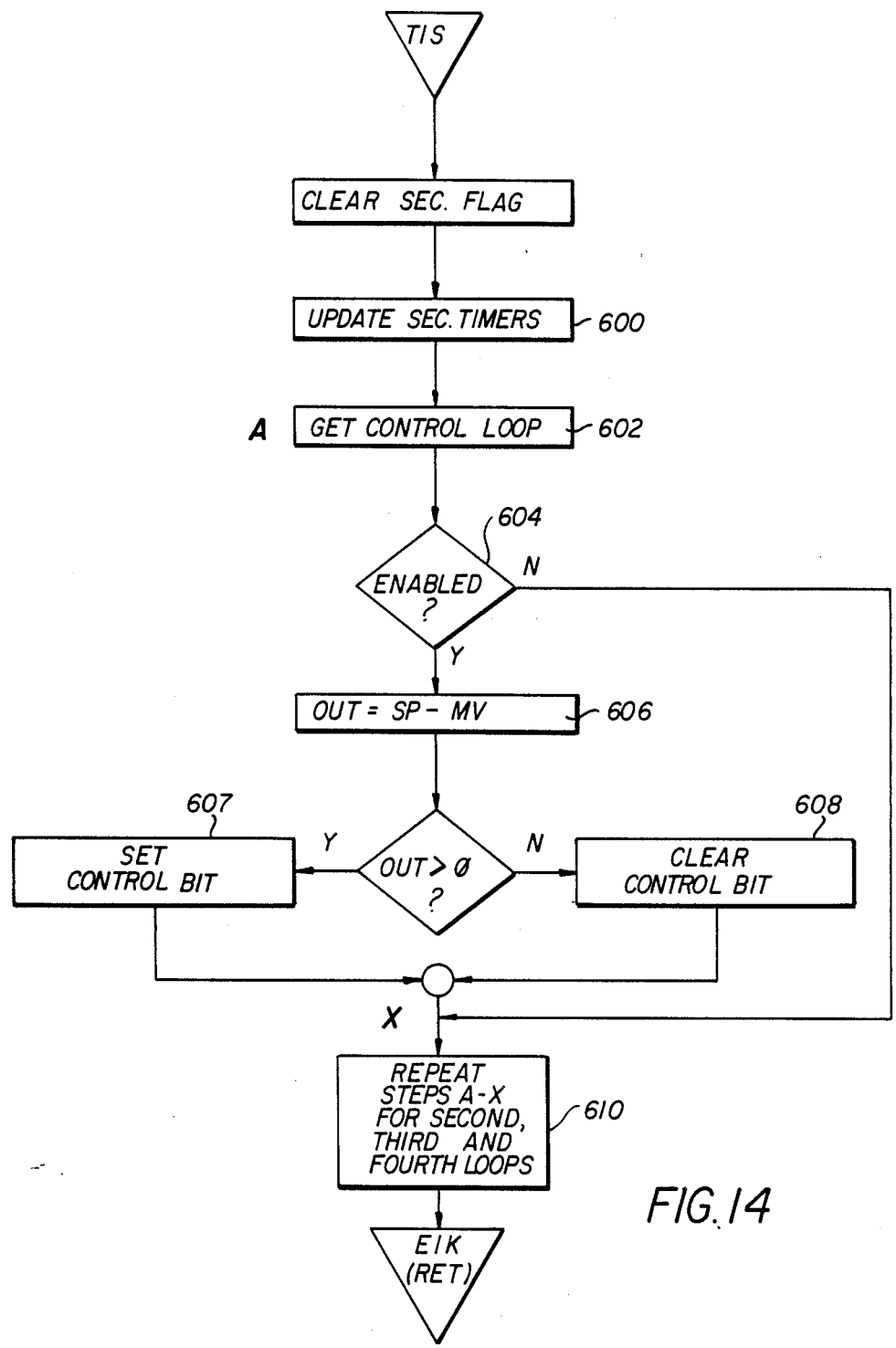
FIG. 14 is a flowchart of another of the timed functions of the software for the gas sterilant system according to the present invention.
Figure 16:
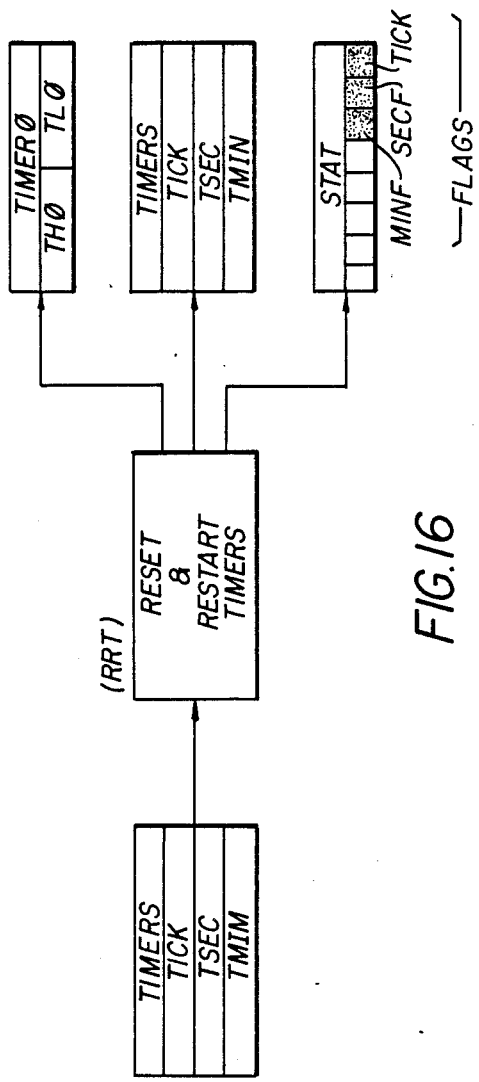
FIG. 16 is a flowchart for a program implemented in the control unit for resetting the control unit timed functions.

As shown in FIG. 14, the first function for the one second timer program includes the clearing of the one second flag (SECF) in the STATUS register (see FIG. 12). All one second timers are then decremented, as shown in FIG. 23 and at 600 in FIG. 14. Program T1S then obtains the loop status from the sequencing program at 602, and determines if the corresponding control bit in the CONTROL register 206 for the particular loop has been enabled at 604. Each loop corresponds to one of the four measured analog process variables, pressure, temperature, humidity and gas concentration. This is also shown in FIG. 24. As indicated, the lower four bits of the CONTROL register 206 correspond to the status of the four loops. If the loop is enabled, a value is determined by subtracting a measured input value, e.g., gas concentration or pressure, from a stored set point value from the sequencing program, as shown at 606. If this value is greater than 0, a corresponding one of the four upper bits in the CTRL register is set at 607. If the CTRL register bit is 0, then the corresponding CONTROL register bit is cleared, as shown at 608.

At 610, the program gets the next loop and repeats steps A-X for that loop. Then the next two loops are obtained and steps A-X repeated sequentially for those two loops. When all four loops have been performed, a return is made to the main dispatching program.

The interrelationship between the analog input data, set points, control register, control program (CTR), output loading program (CTL) and contact outputs CCO are shown in FIG. 24. As shown, program CTR retrieves analog input data ADI, setpoints SP and the control register (CTRL) status from memory. The new status for the control register is then determined in accordance with the flowchart of FIGS. 14 and the new status loaded into the CTRL register. Program CTL then loads the appropriate outputs for controlling the valves and heater into the appropriate contact output register in memory. During the TMRO program these outputs are then coupled to the controlled devices by the program WCO. See FIGS. 10 and 20.

4. Minute Timer (TIM)

Figure 15:
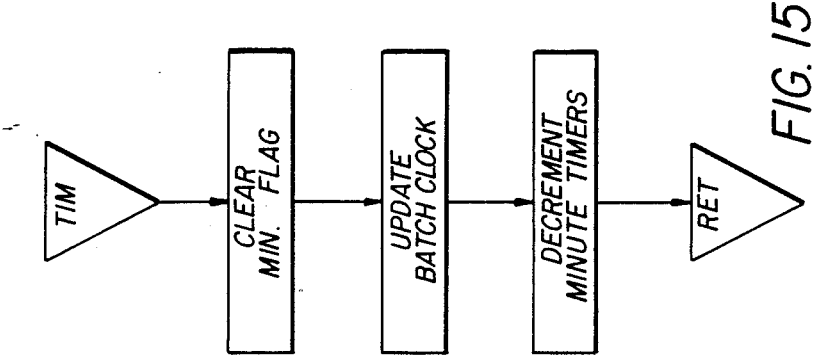
FIG. 15 is a flowchart for another of the timed functions of the software for the gas sterilant system according to the present invention.

At one-minute intervals, an optional batch time clock 119 may be updated as shown at 610. This clock may be used to initiate the display of process conditions by an appropriate printing or display device. All one-minute timers are decremented at 620, and their corresponding status bits are set or cleared at 630. The TIM program is summarized in the flowchart of FIG. 15.

A sample listing of the software for the gas sterilant system according to the invention is appended below.

```
$TITLE(PROGRAM FOR SC1 STERILIZATION CONTROLLER)
;
;
;**********************************************************
;*        CONSTANT DEFINITIONS
;*
;**********************************************************
MCHAN     EQU      07H            ;MAX A/D CHAN NUMBER
CHMSK     EQU      07H            ;A/D CHANNEL MASK
BNK0      EQU      00H            ;RB0
BNK1      EQU      08H            ;RB1
BNK2      EQU      10H            ;RB2
BNK3      EQU      18H            ;RB3
STATE     EQU      R6             ;CURRENT STATE
ABORT     EQU      R7             ;ABORT STATE
SSTA      EQU      0              ;SRAM OFFSET FOR STATE
SABO      EQU      2              ;SRAM OFFSET FOR ABORT
SCNT      EQU      4              ;SRAM OFFSET FOR COUNT
SMAX      EQU      38             ;MAX. VALID STATE
VDLY      EQU      8              ;VALVE DELAY (400 MSEC.)
HDLY      EQU      2              ;HEATER DELAY (2 MIN)
TVAC      EQU      30             ;EVAC TIME (30 MIN)
LKHT      EQU      5              ;LEAK HOLD TIME (5 MIN)
PVAC      EQU      242            ;EVAC PRESSURE (95% FS)
PRLK      EQU      223            ;PRESS. LEAK LIM. (80% FS)
HUMT      EQU      30             ;HUMIDIF. TIME (30 MIN.)
HNOM      EQU      207            ;NOM. HUM. LEVEL (81% FS)
HUMH      EQU      90             ;HUM. HOLD TIME (90 MIN.)
TLOW      EQU      0              ;MIN. STERIL. TEMP.(0% FS)
TMAX      EQU      255            ;MAX. STERIL. TEMP.(100%)
CNCT      EQU      15             ;CONC. TIME (15 MIN.)
CNOM      EQU      64             ;NOM. STERIL. CONC.
CONH      EQU      100            ;GAS HOLD TIME (100 MIN)
TSTR      EQU      200            ;STERIL. TIME (200 MIN)
TEVC      EQU      30             ;EVAC. TIME (30 MIN.)
PN2T      EQU      15             ;N2 PRESS. TIME (15 MIN)
DSRB      EQU      30             ;DESORB. TIME (30 MIN)
TLGH      EQU      15             ;LOW GAS HOLD TIME (15)
CNTM      EQU      5              ;MIN. NO. OF PURGE CYCLES
CMIN      EQU      25             ;MIN. CONCENTRATION (10%)
PATM      EQU      12             ;ATM PRESS. (5% FS)
PMAX      EQU      28             ;MAX OPER. PRESS. (11% FS)
```

```
TDMP     EQU       15                    ;DUMP HOLD TIME (15 MIN)
PSP1     EQU       60                    ;PRESSURE SETPOINT
TSP1     EQU       60                    ;TEMPERATURE SETPOINT
HSP1     EQU       60                    ;HUMIDITY SETPOINT
CSP1     EQU       60.                   ;CONCENTRATION SETPOINT
;
;
;***********************************************************
;*       EXTERNAL DEVICE ADDRESSES
;*
;***********************************************************
;*       EXTERNAL SHADOW RAM
SRAM     XDATA     2000H                 ;SHADOW RAM ADDRESS
;
;*       ANALOG INPUTS
IN0      XDATA     6000H                 ;CHAN-0 ADDRESS (PRESS.)
IN1      XDATA     6001H                 ;CHAN-1 ADDRESS (TEMP.)
IN2      XDATA     6002H                 ;CHAN-2 ADDRESS (HUM.)
IN3      XDATA     6003H                 ;CHAN-3 ADDRESS (CONC.)
IN4      XDATA     6004H                 ;CHAN-4 ADDRESS
IN5      XDATA     6005H                 ;CHAN-5 ADDRESS
IN6      XDATA     6006H                 ;CHAN-6 ADDRESS
IN7      XDATA     6007H                 ;CHAN-7 ADDRESS
;
;*       CLOCK PORT
CLK      XDATA     4000H                 ;CLOCK ADDRESS
;
;*       CONTACT INPUTS
X0       XDATA     0C000H                ;CCI-0   ADDRESS
X1       XDATA     0C001H                ;CCI-1   ADDRESS
X2       XDATA     0C002H                ;CCI-2   ADDRESS
X3       XDATA     0C003H                ;CCI-3   ADDRESS
;
;*       SWITCHES
SW1      XDATA     0C004H                ;SWITCH ADDRESS
;
;*       CONTACT OUTPUTS
Y0       XDATA     0E000H                ;CCO-0   ADDRESS
Y1       XDATA     0E001H                ;CCO-1   ADDRESS
Y2       XDATA     0E002H                ;CCO-2   ADDRESS
Y3       XDATA     0E003H                ;CCO-3   ADDRESS
;
;*       WATCHDOG TIMER
WDT      XDATA     0E004H                ;WATCHDOG RESET ADDRESS
;***********************************************************
;*       DATA-BASE ALLOCATIONS
;*
;***********************************************************
         DSEG
         ORG       05H                   ;TIME COUNTERS
TICK     DS        1                     ;TICK COUNT
TSEC     DS        1                     ;SEC. COUNT
TMIN     DS        1                     ;MIN. COUNT
         ORG       0CH                   ;SIO BUFFER POINTERS
RPUT     DS        1                     ;RCV PUT POINTER
RTAK     DS        1                     ;RCV TAKE POINTER
TPUT     DS        1                     ;XMT PUT POINTER
TTAK     DS        1                     ;XMT TAKE POINTER
         ORG       18H                   ;TIC TIMERS
TTM0     DS        1                     ;TTIMER-0
```

```
TTM1        DS          1               ;TTIMER-1
            ORG         1AH             ;SECOND TIMERS
STM0        DS          1               ;STIMER-0
STM1        DS          1               ;STIMER-1
            ORG         1CH             ;MINUTE TIMERS
MTM0        DS          1               ;MTIMER-0
MTM1        DS          1               ;MTIMER-1
            ORG         1EH             ;COUNTERS
CNT0        DS          1               ;COUNTR-0
CNT1        DS          1               ;COUNTR-1
            BSEG
            ORG         20H             ;INTERNAL BIT SPACE
STAT        DATA        20H             ;STATUS BYTE
CTRL        DATA        21H             ;CONTROL BYTE
TCEN        DATA        22H             ;TIMER/COUNTER ENABLES
TCFL        DATA        23H             ;TIMER/COUNTER FLAGS
MSK0        DATA        24H             ;OUTPUT MASK REGISTER
MSK1        DATA        25H             ;OUTPUT MASK REGISTER
MSK2        DATA        26H             ;OUTPUT MASK REGISTER
MSK3        DATA        27H             ;OUTPUT MASK REGISTER
            ORG         28H             ;IMAGED I/O BITS
CCO0        DATA        28H             ;OUTPUT PORT 1
CCO1        DATA        29H             ;OUTPUT PORT 1
CCO2        DATA        2AH             ;OUTPUT PORT 2
CCO3        DATA        2BH             ;OUTPUT PORT 3
CCI0        DATA        2CH             ;INPUT PORT 0
CCI1        DATA        2DH             ;INPUT PORT 1
CCI2        DATA        2EH             ;INPUT PORT 2
CCI3        DATA        2FH             ;INPUT PORT 3
            DSEG
            ORG         30H             ;ANALOG DATA IMAGE
ADI0        DS          1               ;PRESS. INPUT
ADI1        DS          1               ;TEMP. INPUT
ADI2        DS          1               ;HUM. INPUT
ADI3        DS          1               ;CONC. INPUT
ADI4        DS          1               ;CHANNEL 4 INPUT
ADI5        DS          1               ;CHANNEL 5 INPUT
ADI6        DS          1               ;CHANNEL 6 INPUT
ADI7        DS          1               ;CHANNEL 7 INPUT
            ORG         38H             ;INTERNAL DATA AREA
STP0        DS          1               ;PRESS. SETPOINT
STP1        DS          1               ;TEMP. SETPOINT
STP2        DS          1               ;HUM. SETPOINT
STP3        DS          1               ;CONC. SETPOINT
            ORG         3CH             ;BATCH TIME CLOCK
TIME        DS          1               ;BATCH TIME
;
;*************************************************************
;*      DATA DEFINITIONS
;*
;*      [STATUS & CONTROL]
;*
;*************************************************************
;           STATUS
TICF        BIT         STAT.0          ;TICK FLAG
SECF        BIT         STAT.1          ;SECOND FLAG
MINF        BIT         STAT.3          ;MINUTE FLAG
RCVF        BIT         STAT.4          ;RCV FLAG
XMTF        BIT         STAT.5          ;XMT FLAG
TMOF        BIT         STAT.6          ;TIMEOUT FLAG
```

```
ALMF       BIT       STAT.7       ;ALARM FLAG
;
;          CTRL
CEN0       BIT       CTRL.0       ;PRESS. LOOP ENABLE
CEN1       BIT       CTRL.1       ;TEMP. LOOP ENABLE
CEN2       BIT       CTRL.2       ;HUM. LOOP ENABLE
CEN3       BIT       CTRL.3       ;CONC. LOOP ENABLE
CTR0       BIT       CTRL.4       ;PRESS. LOOP OUTPUT
CTR1       BIT       CTRL.5       ;TEMP. LOOP OUTPUT
CTR2       BIT       CTRL.6       ;HUM. LOOP OUTPUT
CTR3       BIT       CTRL.7       ;CONC. LOOP OUTPUT
;          TCEN
TEN0       BIT       TCEN.0       ;TT0 ENABLE
TEN1       BIT       TCEN.1       ;TT1 ENABLE
TEN2       BIT       TCEN.2       ;ST0 ENABLE
TEN3       BIT       TCEN.3       ;ST1 ENABLE
TEN4       BIT       TCEN.4       ;MT0 ENABLE
TEN5       BIT       TCEN.5       ;MT1 ENABLE
TEN6       BIT       TCEN.6       ;MT2 ENABLE
TEN7       BIT       TCEN.7       ;MT3 ENABLE
;
;          TCFL
TFL0       BIT       TCFL.0       ;TT0 TIMEOUT
TFL1       BIT       TCFL.1       ;TT1 TIMEOUT
TFL2       BIT       TCFL.2       ;ST0 TIMEOUT
TFL3       BIT       TCFL.3       ;ST1 TIMEOUT
TFL4       BIT       TCFL.4       ;MT0 TIMEOUT
TFL5       BIT       TCFL.5       ;MT1 TIMEOUT
TFL6       BIT       TCFL.6       ;CT0 UNDERFLOW
TFL7       BIT       TCFL.7       ;CT1 UNDERFLOW
;
;*************************************************************
;*         DATA DEFINITIONS
;*
;*         [OUTPUT PORTS]
;*
;*************************************************************
;          OPORT_0
LT01       BIT       CC00.0       ;DOOR-OPEN
LT02       BIT       CC00.1       ;EVAC-FAIL
LT03       BIT       CC00.2       ;FILL-FAIL
LT04       BIT       CC00.3       ;STERIL-FAIL
LT05       BIT       CC00.4       ;PURGE-FAIL
LT06       BIT       CC00.5       ;LOAD-UNSTERILE
LT07       BIT       CC00.6       ;SPARE
LT08       BIT       CC00.7       ;TEST-FAIL
;
;          OPORT-1
LT11       BIT       CC01.0       ;READY-FOR-CYCLE
LT12       BIT       CC01.1       ;CYCLE-IN-PROGRESS
LT13       BIT       CC01.2       ;EVAC-IN-PROGRESS
LT14       BIT       CC01.3       ;FILL-IN-PROGRESS
LT15       BIT       CC01.4       ;STERIL-IN-PROGRESS
LT16       BIT       CC01.5       ;PURGE-IN-PROGRESS
LT17       BIT       CC01.6       ;REMOVE-LOAD
LT18       BIT       CC01.7       ;SPARE
;
;          OPORT_2
VV01       BIT       CC02.0       ;OPEN-MAIN-VAC-VALVE
VV02       BIT       CC02.1       ;OPEN-MAIN-GAS-VALVE
```

```
VV03        BIT         CCO2.2          ;OPEN-MAIN-DUMP-VALVE
VV04        BIT         CCO2.3          ;OPEN-GAS-CTRL-VALVE
VV05        BIT         CCO2.4          ;OPEN-N2-CTRL-VALVE
VV06        BIT         CCO2.5          ;OPEN-STEAM-CTRL-VALVE
VV07        BIT         CCO2.6          ;OPEN-BREAK-VALVE
VV08        BIT         CCO2.7          ;OPEN-DUMP-VAC-VALVE
;
;           OPORT_3
PP01        BIT         CCO3.0          ;TURN-P1-ON
HT01        BIT         CCO3.1          ;TURN-H1-ON
SPR1        BIT         CCO3.2          ;SPARE
SPR2        BIT         CCO3.3          ;SPARE
SPR3        BIT         CCO3.4          ;SPARE
SPR4        BIT         CCO3.5          ;SPARE
ADZC        BIT         CCO3.6          ;A/D ZERO CALIB.
LGG1        BIT         CCO3.7          ;CONC. HIGH GAIN SWITCH
;*****************************************************************
;*          DATA DEFINITIONS
;*
;*          [INPUT PORTS]
;*
;*****************************************************************
;           IPORT_0
LSC1        BIT         CCI0.0          ;V1-CLOSED
LSC2        BIT         CCI0.1          ;V2-CLOSED
LSC3        BIT         CCI0.2          ;V3-CLOSED
LSC4        BIT         CCI0.3          ;V4-CLOSED
LSC5        BIT         CCI0.4          ;V5-CLOSED
LSC6        BIT         CCI0.5          ;V6-CLOSED
LSC7        BIT         CCI0.6          ;V7-CLOSED
LSC8        BIT         CCI0.7          ;V8-CLOSED
;
;           IPORT_1
LSO1        BIT         CCI1.0          ;V1-OPEN
LSO2        BIT         CCI1.1          ;V2-OPEN
LSO3        BIT         CCI1.2          ;V3-OPEN
LSO4        BIT         CCI1.3          ;V4-OPEN
LSO5        BIT         CCI1.4          ;V5-OPEN
LSO6        BIT         CCI1.5          ;V6-OPEN
LSO7        BIT         CCI1.6          ;V7-OPEN
LSO8        BIT         CCI1.7          ;V8-OPEN
;
;           IPORT_2
DSC1        BIT         CCI2.0          ;DOOR-SW-CLOSED
TSC1        BIT         CCI2.1          ;TEMP-SW-CLOSED
SWC1        BIT         CCI2.2          ;MAN-SW1-CLOSED
SWC2        BIT         CCI2.3          ;MAN-SW2-CLOSED
SI01        BIT         CCI2.4          ;SPARE
SI02        BIT         CCI2.5          ;SPARE
SI03        BIT         CCI2.6          ;SPARE
SI04        BIT         CCI2.7          ;SPARE
;
;           IPORT_3
SI05        BIT         CCI3.0          ;SPARE
SI06        BIT         CCI3.1          ;SPARE
SI07        BIT         CCI3.2          ;SPARE
SI08        BIT         CCI3.3          ;SPARE
SI09        BIT         CCI3.4          ;SPARE
SI10        BIT         CCI3.5          ;SPARE
SI11        BIT         CCI3.6          ;SPARE
```

```
SI12      BIT       CCI3.7         ;SPARE
;
;****************************************************************
;*        MASK BIT DEFINITIONS
;*
;****************************************************************
;         MASK-REG-0
MVC1      BIT       MSK0.0         ;V1-CLOSED-MASK
MVC2      BIT       MSK0.1         ;V2-CLOSED-MASK
MVC3      BIT       MSK0.2         ;V3-CLOSED-MASK
MVC4      BIT       MSK0.3         ;V4-CLOSED-MASK
MVC5      BIT       MSK0.4         ;V5-CLOSED-MASK
MVC6      BIT       MSK0.5         ;V6-CLOSED-MASK
MVC7      BIT       MSK0.6         ;V7-CLOSED-MASK
MVC8      BIT       MSK0.7         ;V8-CLOSED-MASK
;
;         MASK-REG-1
MVO1      BIT       MSK1.0         ;V1-OPEN-MASK
MVO2      BIT       MSK1.1         ;V2-OPEN-MASK
MVO3      BIT       MSK1.2         ;V3-OPEN-MASK
MVO4      BIT       MSK1.3         ;V4-OPEN-MASK
MVO5      BIT       MSK1.4         ;V5-OPEN-MASK
MVO6      BIT       MSK1.5         ;V6-OPEN-MASK
MVO7      BIT       MSK1.6         ;V7-OPEN-MASK
MVO8      BIT       MSK1.7         ;V8-OPEN-MASK
;
;         MASK-REG-2
MDC1      BIT       MSK2.0         ;DS-CLOSED-MASK
MTC1      BIT       MSK2.1         ;TS-CLOSED-MASK
MSC1      BIT       MSK2.2         ;SW1-CLOSED-MASK
MSC2      BIT       MSK2.3         ;SW2-CLOSED-MASK
;
;****************************************************************
;*        INTERRUPT VECTORS
;*
;****************************************************************
          CSEG
          ORG       0000H
RSTV:     LJMP      INIT                    ;RESET VECTOR
;
          ORG       000BH
TINT:     LJMP      TMR0                    ;TIMER0 VECTOR
;
          ORG       0013H
PINT:     LJMP      PURF                    ;PWR FAIL VECTOR
;
          ORG       001BH
TM1V:     RETI                              ;TIMER1 VECTOR
;
          ORG       0023H
SIOV:     LJMP      SIOHND                  ;SERIAL DATA VECTOR
;
;****************************************************************
;         POWER FAIL HANDLER
;
;****************************************************************
PURF:     CLR       P1.6                    ;STORE SRAM DATA
          SETB      P1.6                    ;DISABLE STORE
          RETI                              ;INTERRUPT RETURN
;
```

```
;**************************************************************
;*      TIMER INTERRUPT HANDLER
;*
;**************************************************************
        ORG     0030H
TMR0:   PUSH    PSW                     ;SAVE PROC. STATUS
        PUSH    ACC                     ;SAVE ACCUMULATOR
        PUSH    DPL                     ;SAVE DP(L)
        PUSH    DPH                     ;SAVE DP(H)
        MOV     PSW,#BNK0               ;USE RB0
        CLR     EA                      ;DISABLE INTERRUPTS
        ACALL   RRT                     ;RESET AND RESTART TIMERS
        ACALL   RCI                     ;READ CONTACT INPUTS
        ACALL   CSC                     ;CONTACT STATUS CHECK
        ACALL   WCO                     ;WRITE CONTACT OUTPUTS
        ACALL   RAI                     ;READ ANALOG INPUTS
        SETB    EA                      ;RESTORE INTERRUPTS
TRTN:   POP     DPH                     ;RESTORE DP(H)
        POP     DPL                     ;RESTORE DP(L)
        POP     ACC                     ;RESTORE ACCUMULATOR
        POP     PSW                     ;RESTORE PROC. STATUS
        RETI                            ;RETURN FROM TIMER0 INT.
;
;**************************************************************
;*      TMR0 SUBROUTINES
;*
;**************************************************************
RRT:    CLR     TR0                     ;STOP TIMER0
        MOV     A,#LOW(-3120+7)         ;LOAD COUNT(L)
        ADD     A,TL0                   ;CORRECT FOR OVERRUN
        MOV     TL0,A                   ;RELOAD COUNTER(L)
        MOV     A,#HIGH(-3120+7)        ;REPEAT FOR COUNT(H)
        ADDC    A,TH0                   ;GET CORRECTED HIGH BYTE
        MOV     TH0,A                   ;LOAD COUNTER(H)
        SETB    TR0                     ;RESTART TIMER
CLOCK:  DJNZ    TICK,CLK3               ;IF 50-MSEC
        MOV     TICK,#8                 ;  RELOAD TICK COUNT
        SETB    TICF                    ;  SET 50-MSEC FLAG
        DJNZ    TSEC,CLK2               ;  IF 1-SEC
        MOV     TSEC,#20                ;    RELOAD TSEC COUNT
        SETB    SECF                    ;    SET 1-SEC FLAG
        DJNZ    TMIN,CLK1               ;    IF 1-MIN
        MOV     TMIN,#60                ;      RELOAD TMIN COUNT
        SETB    MINF                    ;      SET 1-MIN FLAG
        SJMP    CLK4                    ;      END
CLK1:   CLR     MINF                    ;    ELSE, CLR MIN. FLAG
        SJMP    CLK4                    ;    END
CLK2:   CLR     SECF                    ;  ELSE, CLR SEC. FLAG
        SJMP    CLK4                    ;  END
CLK3:   CLR     TICF                    ;ELSE, CLR TIC. FLAG
CLK4:   NOP                             ; END
        RET                             ;RETURN FROM TIMER PROG.
RCI:    MOV     DPTR,#X0                ;POINT CONTACT INPUTS
        MOV     R0,#CCI0                ;POINT DATA-BASE IMAGE
        MOV     R4,#4                   ;FOR R4:=4 DOWNTO 0 DO
CI1:    CLR     P1.4                    ;  ENABLE I/O
        MOVX    A,@DPTR                 ;  GET INPUT
        SETB    P1.4                    ;  DISABLE I/O
        MOV     @R0,A                   ;  STORE IT IN DATA-BASE
        INC     DPTR                    ;  POINT NEXT INPUT
```

```
          INC      R0              ; POINT NEXT STORAGE
          DJNZ     R4,CI1          ; END
          RET                      ;RETURN
;
CSC:      CLR      ALMF            ;CLEAR ALARM FLAG
          MOV      A,CCO2          ;GET VALVE OUTPUTS
          XRL      A,CCI1          ;COMPARE WITH LSO INPUTS
          ANL      A,MSK1          ;MASK OFF VO DON'T CARES
          MOV      R2,A            ;SAVE PARTIAL RESULT
          MOV      A,CCO2          ;GET VALVE OUTPUTS
          CPL      A               ;MAKE CLOSED NORMAL
          XRL      A,CCIO          ;COMPARE WITH LSC INPUTS
          ANL      A,MSK0          ;MASK OFF VC DON'T CARES
          ORL      A,R2            ;ADD PREV. RESULT
          JZ       CSC2            ;  IF MISMATCH
          SETB     ALMF            ;    SET ALARM FLAG
CSC2:     NOP                      ;  END
          MOV      A,TCFL          ;GET TIMEOUTS
          ANL      A,TCEN          ;TEST IF ENABLED
          JZ       CSC4            ;IF (TMO.AND.TEN)
          SETB     TMOF            ;  SET TIMEOUT FLAG
          SJMP     CSC5            ;  END
CSC4:     CLR      TMOF            ;ELSE, CLEAR TIMEOUT FLAG
CSC5:     NOP                      ;  END
          RET                      ;RETURN
;
WCO:      MOV      DPTR,#YO        ;POINT CONTACT OUTPUTS
          MOV      R0,#CCO0        ;POINT DATA-BASE IMAGE
          MOV      R4,#4           ;FOR R4:=4 DOWNTO 0 DO
CO1:      MOV      A,@R0           ;  GET OUTPUT DATA
          CPL      A               ;  INVERT IT FOR OUTPUT
          CLR      P1.4            ;  ENABLE I/O
          MOVX     @DPTR,A         ;  LOAD OUTPUT LATCH
          SETB     P1.4            ;  DISABLE I/O
          INC      DPTR            ;  POINT NEXT OUTPUT
          INC      R0              ;  POINT NEXT DATA
          DJNZ     R4,CO1          ;  END
          RET                      ;RETURN
RAI:      MOV      DPTR,#IN0       ;POINT FIRST ANALOG CHAN.
          MOV      R0,#ADI0        ;POINT FIRST ANALOG DATA
          MOV      R4,#8           ;FOR R4:=8 DOWNTO 0 DO
RA1:      CLR      P1.4            ;  ENABLE I/O
          MOVX     A,@DPTR         ;  GET ANALOG DATA
          SETB     P1.4            ;  DISABLE I/O
          ACALL    FILTER          ;  FILTER ANALOG DATA
          MOV      @R0,A           ;  LOAD IT INTO DATA BASE
          INC      DPTR            ;  POINT NEXT CHANNEL
          INC      R0              ;  POINT NEXT DATA
          DJNZ     R4,RA1          ;  END
          RET                      ;RETURN
;
FILTER:   MOV      B,#020H         ;LOAD FILT. CONST, CB
          MUL      AB              ;B,A:=0.125*R(I)
          PUSH     B               ;SAVE PROD(H)
          PUSH     ACC             ;SAVE PROD(L)
          MOV      B,#0E0H         ;LOAD (1-CB) CONST.
          MOV      A,@R0           ;GET X(I-1)
          MUL      AB              ;B,A:=0.875*X(I-1)
          MOV      R2,B            ;SAVE HIGH BYTE
          POP      B               ;LOAD PROD(L)
```

```
                ADD         A,B                     ;ADD LOW BYTES
                XCH         A,R2                    ;GET HIGH BYTE
                POP         B                       ;LOAD PROD(H)
                ADDC        A,B                     ;A,R2 IS FILTERED DATA
                RET                                 ;RETURN
;
;***********************************************************************
;               SCHEDULED TIME FUNCTIONS
;
;***********************************************************************
T50:            CLR         TICF                    ;CLEAR TICK FLAG
                MOV         PSW,#BNK2               ;USE RB2
                ACALL       RWT                     ;RESET WATCHDOG TIMER
                ACALL       DTT                     ;DECREMENT TICK TIMERS
                ACALL       SEQ                     ;PERFORM SEQUENCE LOGIC
                ACALL       CTL                     ;LOAD CONTROL OUTPUTS
                RET                                 ;RETURN TO DISPATCHING
;
T1K:            CLR         SECF                    ;CLEAR 1-SEC FLAG
                MOV         PSW,#BNK2               ;USE RB2
                ACALL       DST                     ;DECREMENT SECOND TIMERS
                ACALL       CTR                     ;PERFORM CONTROL ACTIONS
                RET
;
T1M:            CLR         MINF                    ;CLEAR 1-MIN FLAG
                MOV         PSW,#BNK2               ;USE RB2
                ACALL       UBC                     ;UPDATE BATCH CLOCK
                ACALL       DMT                     ;DECREMENT MINUTE TIMERS
                RET
;
RWT:            MOV         DPTR,#WDT               ;POINT WATCHDOG TIMER
                CLR         A                       ;CLEAR ACCUMULATOR
                CLR         P1.4                    ;ENABLE I/O
                MOVX        @DPTR,A                 ;RESET WATCHDOG TIMER
                SETB        P1.4                    ;DISABLE I/O
                RET
;
UBC:            MOV         R0,#TIME                ;POINT TIME(L)
                CLR         C                       ;CLEAR CARRY
                XCH         A,@R0                   ;GET TIME(L)
                INC         A                       ;INCREMENT IT
                XCH         A,@R0                   ;UPDATE TIME(L)
                INC         R0                      ;POINT TIME(H)
                XCH         A,@R0                   ;GET TIME(H)
                ADDC        A,#0                    ;PROPAGATE CARRY
                XCH         A,@R0                   ;UPDATE TIME(H)
                RET
;
;***********************************************************************
;*              CONTROL CALCULATIONS
;*
;***********************************************************************
CTR:            MOV         R0,#STPO                ;POINT SETPOINT
                MOV         R1,#ADIO                ;POINT DATA
                CLR         C                       ;CLEAR CARRY
                MOV         A,@R0                   ;GET PRESS. SETPOINT
                SUBB        A,@R1                   ;SUBTRACT MEAS. PRESS.
                JNC         CT2                     ;IF MV>SP
                SETB        CTRO                    ;  INCREASE OUTPUT
                SJMP        CT3                     ;  END
```

```
CT2:    CLR     CTR0            ;ELSE, DECR. OUTPUT
CT3:    NOP                     ;   END
        INC     R0              ;POINT NEXT SETPOINT
        INC     R1              ;POINT NEXT MEASUREMENT
        CLR     C               ;CLEAR CARRY
        MOV     A,@R0           ;GET TEMP. SETPOINT
        SUBB    A,@R1           ;SUBTRACT MEAS. TEMP.
        JNC     CT4             ;IF MV>SP
        CLR     CTR1            ;   DECREASE OUTPUT
        SJMP    CT5             ;   END
CT4:    SETB    CTR1            ;ELSE, INCR. OUTPUT
CT5:    NOP                     ;   END
        INC     R0              ;POINT NEXT SETPOINT
        INC     R1              ;POINT NEXT MEASUREMENT
        CLR     C               ;CLEAR CARRY
        MOV     A,@R0           ;GET HUM. SETPOINT
        SUBB    A,@R1           ;SUBTRACT HUM. MEAS.
        JNC     CT6             ;IF MV>SP
        CLR     CTR2            ;   DECREASE OUTPUT
        SJMP    CT7             ;   END
CT6:    SETB    CTR2            ;ELSE, INCREASE OUTPUT
CT7:    NOP                     ;   END
        INC     R0              ;POINT NEXT SETPOINT
        INC     R1              ;POINT NEXT MEASUREMENT
        CLR     C               ;CLEAR CARRY
        MOV     A,@R0           ;GET CONC. SETPOINT
        SUBB    A,@R1           ;SUBTRACT CONC. MEAS.
        JNC     CT8             ;IF MV>SP
        CLR     CTR3            ;   DECREASE OUTPUT
        SJMP    CT9             ;   END
CT8:    SETB    CTR3            ;ELSE, INCR. OUTPUT
CT9:    NOP                     ;   END
        RET                     ;RETURN
;
;***************************************************************
;*      SOFTWARE TICK TIMERS (50 MSEC)
;*
;***************************************************************
DTT:    MOV     R0,#TTM0        ;POINT FIRST TICK TIMER
        MOV     A,@R0           ;GET LAST COUNT
        JZ      TT1             ;IF COUNT<>0
        DEC     A               ;   DECREMENT ACC.
        MOV     @R0,A           ;   UPDATE COUNT
        JZ      TT1             ;   IF NOT TIMEOUT
        CLR     TFL0            ;      CLEAR FLAG
        SJMP    TT2             ;      END
TT1:    SETB    TFL0            ;   ELSE, SET FLAG
TT2:    NOP                     ;   END
;
        MOV     R0,#TTM1        ;POINT SECOND TICK TIMER
        MOV     A,@R0           ;GET LAST COUNT
        JZ      TT4             ;IF COUNT<>0
        DEC     A               ;   DECREMENT ACC.
        MOV     @R0,A           ;   UPDATE COUNT
        JZ      TT4             ;   IF NOT TIMEOUT
        CLR     TFL1            ;      CLEAR FLAG
        SJMP    TT5             ;      END
TT4:    SETB    TFL1            ;   ELSE, SET FLAG
TT5:    NOP                     ;   END
        RET                     ;RETURN
;
```

```
;****************************************************************
;*      SOFTWARE SECOND TIMERS
;*
;****************************************************************
DST:    MOV     R0,#STM0                ;POINT FIRST SEC. TIMER
        MOV     A,@R0                   ;GET LAST COUNT
        JZ      ST1                     ;IF COUNT<>0
        DEC     A                       ;   DECREMENT ACC.
        MOV     @R0,A                   ;   UPDATE COUNT
        JZ      ST1                     ;   IF NOT TIMEOUT
        CLR     TFL2                    ;      CLEAR FLAG
        SJMP    ST2                     ;      END
ST1:    SETB    TFL2                    ; ELSE, SET FLAG
ST2:    NOP                             ; END
;
        MOV     R0,#STM1                ;POINT NEXT SECOND TIMER
        MOV     A,@R0                   ;GET LAST COUNT
        JZ      ST4                     ;IF COUNT<>0
        DEC     A                       ;   DECREMENT ACC.
        MOV     @R0,A                   ;   UPDATE COUNT
        JZ      ST4                     ;   IF NOT TIMEOUT
        CLR     TFL3                    ;      CLEAR FLAG
        SJMP    ST5                     ;      END
ST4:    SETB    TFL3                    ; ELSE, SET FLAG
ST5:    NOP                             ; END
        RET                             ;RETURN
;
;****************************************************************
;*      SOFTWARE MINUTE TIMERS
;*
;****************************************************************
DMT:    MOV     R0,#MTM0                ;POINT FIRST MIN. TIMER
        MOV     A,@R0                   ;GET LAST COUNT
        JZ      MT1                     ;IF COUNT<>0
        DEC     A                       ;   DECREMENT ACC.
        MOV     @R0,A                   ;   UPDATE COUNT
        JZ      MT1                     ;   IF NOT TIMEOUT
        CLR     TFL4                    ;      CLEAR FLAG
        SJMP    MT2                     ;      END
MT1:    SETB    TFL4                    ; ELSE, SET FLAG
MT2:    NOP                             ; END
;
        MOV     R0,#MTM1                ;POINT SECOND MIN. TIMER
        MOV     A,@R0                   ;GET LAST COUNT
        JZ      MT4                     ;IF COUNT<>0
        DEC     A                       ;   DECREMENT ACC.
        MOV     @R0,A                   ;   UPDATE COUNT
        JZ      MT4                     ;   IF NOT TIMEOUT
        CLR     TFL5                    ;      CLEAR FLAG
        SJMP    MT5                     ;      END
MT4:    SETB    TFL5                    ; ELSE, SET FLAG
MT5:    NOP                             ; END
        RET                             ;RETURN
;****************************************************************
;*      SOFTWARE COUNTERS
;*
;****************************************************************
DCT0:   MOV     R0,#CNT0                ;POINT FIRST COUNTER
        MOV     A,@R0                   ;GET LAST COUNT
        JZ      DC1                     ;IF COUNT<>0
```

```
          DEC     A                   ; DECREMENT ACC.
          MOV     @R0,A               ; UPDATE COUNT
          JZ      DC1                 ; IF NOT ZERO
          CLR     TFL6                ;    CLEAR FLAG
          SJMP    DC2                 ;    END
DC1:      SETB    TFL6                ; ELSE, SET FLAG
DC2:      NOP                         ; END
          RET                         ;RETURN
;
DCT1:     MOV     R0,#CNT1            ;POINT SECOND COUNTER
          MOV     A,@R0               ;GET LAST COUNT
          JZ      DC3                 ;IF COUNT<>0
          DEC     A                   ;  DECREMENT ACC.
          MOV     @R0,A               ;  UPDATE COUNT
          JZ      DC3                 ;  IF NOT ZERO
          CLR     TFL7                ;    CLEAR FLAG
          SJMP    DC4                 ;    END
DC3:      SETB    TFL7                ; ELSE, SET FLAG
DC4:      NOP                         ; END
          RET                         ;RETURN
;
;************************************************************
;*        CONTROL OUTPUTS
;*
;************************************************************
CTL:      MOV     C,CTR0              ;GET OUTPUT-0
          ANL     C,CEN0              ;ALLOW IF ENABLED
          MOV     VV05,C              ;OUTPUT TO V5
;
          MOV     C,CTR1              ;GET OUTPUT-1
          ANL     C,CEN1              ;ALLOW IF ENABLED
          MOV     HT01,C              ;OUTPUT TO H1
;
          MOV     C,CTR2              ;GET OUTPUT-2
          ANL     C,CEN2              ;ALLOW IF ENABLED
          MOV     VV06,C              ;OUTPUT TO V6
;
          MOV     C,CTR3              ;GET OUTPUT-3
          ANL     C,CEN3              ;ALLOW IF ENABLED
          MOV     VV04,C              ;OUTPUT TO V4
;
          RET
;
;************************************************************
;*        POWER-ON INITIALIZATION
;*
;************************************************************
INIT:     MOV     SP,#060H            ;INITIALIZE STACK POINTER
          MOV     PSW,#BNK0           ;USE RB0
          CLR     A                   ;CLEAR ACCUMULATOR
          MOV     R0,#2               ;POINT LOWEST RAM LOC.
          MOV     R1,#126             ;FOR R1:=126 DOWNTO 0 DO
ILP:      MOV     @R0,A               ;  CLEAR MEMORY LOC.
          INC     R0                  ;  POINT NEXT LOCATION
          DJNZ    R1,ILP              ;  END
          MOV     TICK,#8             ;INITIALIZE TICK COUNT
          MOV     TSEC,#20            ;INITIALIZE SEC. COUNT
          MOV     TMIN,#60            ;INITIALIZE MIN. COUNT
          MOV     PSW,#BNK1           ;USE RB1
          MOV     RPUT,#40H           ;INITIALIZE RPUT POINTER
```

```
          MOV     RTAK,#40H          ;INITIALIZE RTAK POINTER
          MOV     TPUT,#50H          ;INITIALIZE TPUT POINTER
          MOV     TTAK,#50H          ;INITIALIZE TTAK POINTER
          MOV     PSW,#BNK2          ;USE RB2
          MOV     STATE,#0           ;STATE:=0
          MOV     ABORT,#0           ;ABORT:=0
          MOV     SCON,#052H         ;SET SERIAL PORT BITS
          MOV     TMOD,#061H         ;SET TIMER MODES
          MOV     87H,#00H           ;SET SMOD:=0 IN PCON
          MOV     IP,#002H           ;SET INTERRUPT PRIORITIES
          MOV     IE,#096H           ;ENABLE INTERRUPTS
          MOV     TL0,#LOW(-3120)    ;LOAD COUNT(L)
          MOV     TH0,#HIGH(-3120)   ;LOAD COUNT(H)
          MOV     TH1,#-13           ;SET BAUD RATE (1200)
          MOV     A,#0FFH            ;SET ACCUM. ALL 1'S
          CLR     P1.4               ;ENABLE I/O
          MOV     DPTR,#Y0           ;POINT Y0 OUTPUTS
          MOVX    @DPTR,A            ;CLEAR Y0
          MOV     DPTR,#Y1           ;POINT Y1 OUTPUTS
          MOVX    @DPTR,A            ;CLEAR Y1
          MOV     DPTR,#Y2           ;POINT Y2 OUTPUTS
          MOVX    @DPTR,A            ;CLEAR Y2
          MOV     DPTR,#Y3           ;POINT Y3 OUTPUTS
          MOVX    @DPTR,A            ;CLEAR Y3
          SETB    P1.4               ;DISABLE I/O
          ACALL   RWT                ;RESET WATCHDOG TIMER
          MOV     TIME,#0            ;CLEAR TIME(L)
          MOV     TIME+1,#0          ;CLEAR TIME(H)
          SETB    TR1                ;START BAUD CLOCK
          SETB    TR0                ;START TIMER
          SJMP    MAIN               ;START MAIN PROGRAM
;
TEST:     RET                        ;TEST COMPUTER FUNCTIONS
;************************************************************
;*        SEQUENCING PROGRAM
;*
;************************************************************
SEQ:      NOP                        ;REPEAT
          MOV     PSW,#BNK2          ;   USE RB2
          MOV     A,STATE            ;   GET CURRENT STATE
          ADD     A,#NOT(SMAX)       ;   COMPARE MAX. STATE
          JNC     SQ1                ;   IF INVALID STATE
          MOV     A,#31              ;     TAKE STATE #31
          MOV     STATE,A            ;     SET STATE TO #31
          SJMP    SQ2                ;   END
SQ1:      MOV     A,STATE            ;   ELSE, USE CURRENT STATE
SQ2:      NOP                        ;   END
          RL      A                  ;   MAKE IT 4-BYTE-
          RL      A                  ;   ADDRESS OFFSET
          MOV     DPTR,#JMPTBL       ;   OFFSET IN JUMP TABLE
          JMP     @A+DPTR            ;   PERFORM STATE
SEQR:     MOV     C,ALMF             ;   GET ALARM FLAG
          ORL     C,TMOF             ;   OR WITH TIMEOUT FLAG
          JNC     SQ3                ;   IF (ALM.OR.TMO)
          MOV     A,ABORT            ;     GET ABORT STATE
          MOV     STATE,A            ;     SET STATE TO ABORT
          CLR     F0                 ;     CLEAR HOLD FLAG
SQ3:      NOP                        ;   END
          JNB     F0,SEQ             ;UNTIL HOLD
          RET                        ;RETURN
```

```
;****************************************************************
;*      MAIN DISPATCHING PROGRAM
;*
;****************************************************************
MAIN:   NOP                             ;DO FOREVER
        JNB     MINF,MN1                ;  IF 1-MIN TIME
        LCALL   T1M                     ;    DO 1-MIN FUNCTIONS
MN1:    JNB     SECF,MN2                ;  IF 1-SEC TIME
        LCALL   T1K                     ;    DO 1-SEC FUNCTIONS
MN2:    JNB     TICF,MN3                ;  IF TICK TIME
        LCALL   T50                     ;    DO TICK FUNCTIONS
MN3:    JNB     RCVF,MN4                ;  IF RCV TIME
        LCALL   RCV                     ;    DO RCV FUNCTIONS
MN4:    JNB     XMTF,MN5                ;  IF XMT TIME
        LCALL   XMT                     ;    DO XMT FUNCTIONS
MN5:    LCALL   TEST                    ;  ELSE, PERFORM TESTS
        SJMP    MAIN                    ;END
;
GTCT:   MOV     A,#1                    ;READ SRAM
        RET
RCV:    CLR     RCVF                    ;RESET RCV FLAG
        RET
XMT:    CLR     XMTF                    ;RESET XMT FLAG
        RET
SIOHND: RET                             ;SERIAL I/O HANDLER $INCLUDE(STATES.SRC)
;
        END
;****************************************************************
;*      STATE JUMP TABLE
;*
;****************************************************************
JMPTBL: LJMP    STATE0          LJMP    STATE13
        DB      0               DB      0
        LJMP    STATE1          LJMP    STATE14
        DB      0               DB      0
        LJMP    STATE2          LJMP    STATE15
        DB      0               DB      0
        LJMP    STATE3          LJMP    STATE16
        DB      0               DB      0
        LJMP    STATE4          LJMP    STATE17
        DB      0               DB      0
        LJMP    STATE5          LJMP    STATE18
        DB      0               DB      0
        LJMP    STATE6          LJMP    STATE19
        DB      0               DB      0
        LJMP    STATE7          LJMP    STATE20
        DB      0               DB      0
        LJMP    STATE8          LJMP    STATE21
        DB      0               DB      0
        LJMP    STATE9          LJMP    STATE22
        DB      0               DB      0
        LJMP    STATE10         LJMP    STATE23
        DB      0               DB      0
        LJMP    STATE11         LJMP    STATE24
        DB      0               DB      0
        LJMP    STATE12         LJMP    STATE25
        DB      0               DB      0
```

```
            LJMP    STATE26                     DB      0
            DB      0                           LJMP    STATE33
            LJMP    STATE27                     DB      0
            DB      0                           LJMP    STATE34
            LJMP    STATE28                     DB      0
            DB      0                           LJMP    STATE35
            LJMP    STATE29                     DB      0
            DB      0                           LJMP    STATE36
            LJMP    STATE30                     DB      0
            DB      0                           LJMP    STATE37
            LJMP    STATE31                     DB      0
            DB      0                           LJMP    STATE38
            LJMP    STATE32                     DB      0
;                                            ;
STATE0:     MOV     STATE,#1                    ;STATE:=1
            MOV     ABORT,#1                    ;ABORT:=1
            MOV     STAT,#00H                   ;RESET STATUS
            MOV     CTRL,#00H                   ;RESET CONTROLS
            MOV     TCEN,#00H                   ;RESET ALARMS
            MOV     TCFL,#00H                   ;RESET TIMEOUT FLAGS
            MOV     MSK0,#00H                   ;RESET CLOSED MASKS
            MOV     MSK1,#00H                   ;RESET OPEN MASKS
            MOV     MSK2,#00H                   ;RESET MISC. MASKS
            MOV     MSK3,#00H                   ;RESET MISC. MASKS
            MOV     CCO0,#00H                   ;RESET ALARM LIGHTS
            MOV     CCO1,#00H                   ;RESET RUN LIGHTS
            MOV     CCO2,#40H                   ;RESET ALL VALVES
            MOV     CCO3,#00H                   ;RESET MISC. OUTPUTS
            CLR     F0                          ;CLEAR HOLD FLAG
            LJMP    SEQR                        ;RETURN
;
STATE1:     JNB     DSC1,S11                    ;IF DOOR CLOSED
            MOV     STATE,#2                    ;   STATE:=2
            MOV     ABORT,#29                   ;   ABORT:=29
            CLR     LT01                        ;   DOOR-OPEN(OFF)
            SETB    LT11                        ;   READY-FOR-CYCLE(ON)
            CLR     F0                          ;   CLEAR HOLD FLAG
            SJMP    S12                         ;   END
S11:        SETB    LT01                        ;ELSE, DOOR-OPEN(ON)
            CLR     LT11                        ;   READY-FOR-CYCLE(OFF)
            SETB    F0                          ;   SET HOLD FLAG
S12:        NOP                                 ;   END
            LJMP    SEQR                        ;RETURN
;
STATE2:     JNB     SWC1,S21                    ;IF START-CYCLE(PUSHED)
            MOV     STATE,#3                    ;   STATE:=3
            MOV     ABORT,#29                   ;   ABORT:=29
            CLR     LT11                        ;   READY-FOR-CYCLE(OFF)
            SETB    LT12                        ;   CYCLE-IN-PROGRESS(ON)
            MOV     CNT0,#CNTM                  ;   LOAD MIN. COUNT
            CLR     TFL6                        ;   CLEAR COUNT FLAG
            CLR     MVC7                        ;   CLEAR VC7 MASK
            CLR     MVO7                        ;   CLEAR VO7 MASK
            CLR     VV07                        ;   CLOSE-BREAK-VALVE
            MOV     TTM0,#VDLY                  ;   LOAD TIMEOUT DELAY
            CLR     TFL0                        ;   RESET TIMEOUT FLAG
            SETB    TEN0                        ;   ENABLE TIMEOUT ALARM
            CLR     F0                          ;   CLEAR HOLD FLAG
            SJMP    S23                         ;   END
S21:        JB      DSC1,S22                    ;ELSE, IF DOOR-OPEN
```

```
              MOV      STATE,#1              ;    STATE:=1
              MOV      ABORT,#29             ;    ABORT:=29
              CLR      F0                    ;    CLEAR HOLD FLAG
              SJMP     S23                   ;    END
    S22:      SETB     F0                    ;  ELSE, SET HOLD FLAG
    S23:      NOP                            ;  END
              LJMP     SEQR                  ;RETURN
    ;
    STATE3:   JNB      LSC7,S31              ;IF V7 CLOSED
              MOV      STATE,#4              ;    STATE:=4
              MOV      ABORT,#29             ;    ABORT:=29
              CLR      TEN0                  ;    CLEAR TIMEOUT ENABLE
              SETB     MVC7                  ;    SET VC7 MASK
              SETB     MVO7                  ;    SET VO7 MASK
              SETB     HTO1                  ;    TURN HEATER ON
              MOV      MTM0,#HDLY            ;    LOAD HEATER TIMEOUT
              CLR      TFL4                  ;    RESET TIMEOUT FLAG
              SETB     TEN4                  ;    ENABLE TIMEOUT ALARM
              CLR      F0                    ;    CLEAR HOLD FLAG
              SJMP     S33                   ;    END
    S31:      JB       DSC1,S32              ;ELSE, IF DOOR OPEN
              MOV      A,ABORT               ;     GET ABORT STATE
              MOV      STATE,A               ;     STATE:=ABORT-1
              SETB     LTO1                  ;     DOOR-OPEN(ON)
              CLR      F0                    ;     CLEAR HOLD FLAG
              SJMP     S33                   ;     END
    S32:      SETB     F0                    ;  ELSE, SET HOLD FLAG
    S33:      NOP                            ;  END
              LJMP     SEQR                  ;RETURN
    ;
    STATE4:   JNB      TSC1,S41              ;IF HEATER ON
              MOV      STATE,#5              ;    STATE:=5
              MOV      ABORT,#29             ;    ABORT:=29
              CLR      TEN4                  ;    CLEAR TIMEOUT ENABLE
              SETB     MTC1                  ;    SET TEMP SW MASK
              MOV      STP1,#TSP1            ;    LOAD TEMP. SETPOINT
              SETB     CEN1                  ;    ENABLE TEMP. CONTROL
              CLR      MVC1                  ;    CLEAR VC1 MASK
              CLR      MVO1                  ;    CLEAR VO1 MASK
              SETB     VVO1                  ;    OPEN V1
              MOV      TTM0,#VDLY            ;    LOAD TIMEOUT DELAY
              CLR      TFL0                  ;    RESET TIMEOUT FLAG
              SETB     TEN0                  ;    ENABLE TIMEOUT ALARM
              CLR      F0                    ;    CLEAR HOLD FLAG
              SJMP     S43                   ;    END
    S41:      JB       DSC1,S42              ;ELSE, IF DOOR OPEN
              MOV      A,ABORT               ;     GET ABORT STATE
              MOV      STATE,A               ;     STATE:=ABORT-1
              SETB     LTO1                  ;     DOOR-OPEN(ON)
              CLR      F0                    ;     CLEAR HOLD FLAG
              SJMP     S43                   ;     END
    S42:      SETB     F0                    ;  ELSE, SET HOLD FLAG
    S43:      NOP                            ;  END
              LJMP     SEQR                  ;RETURN
    ;
    STATE5:   JNB      LSO1,S51              ;IF VAC VALVE OPEN
              MOV      STATE,#6              ;    STATE:=6
              MOV      ABORT,#29             ;    ABORT:=29
              CLR      TEN0                  ;    CLEAR TIMEOUT ENABLE
              SETB     MVC1                  ;    SET VC1 MASK
```

```
          SETB    MVO1            ; SET VO1 MASK
          SETB    PPO1            ; TURN P1 ON
          SETB    LT13            ; EVAC-IN-PROGRESS(ON)
          MOV     MTM0,#TVAC      ; LOAD EVAC TIME
          CLR     TFL4            ; RESET TIMEOUT FLAG
          CLR     F0              ; CLEAR HOLD FLAG
          SJMP    S53             ; END
S51:      JB      DSC1,S52        ;ELSE, IF DOOR OPEN
          MOV     A,ABORT         ;    GET ABORT STATE
          MOV     STATE,A         ;    STATE:=ABORT-1
          SETB    LT01            ;    DOOR-OPEN(ON)
          CLR     F0              ;    CLEAR HOLD FLAG
          SJMP    S53             ;    END
S52:      SETB    F0              ; ELSE, SET HOLD FLAG
          NOP                     ;    END
S53:      LJMP    SEQR            ;RETURN
;
STATE6:   JNB     TFL4,S62        ;IF EVAC TIME
          CLR     C               ;  CLEAR CARRY
          MOV     A,ADIO          ;  GET PRESSURE
          SUBB    A,#PVAC         ;  SUBTRACT PRESS. LIMIT
          JC      S61             ;  IF P.LE.PVAC
          MOV     STATE,#7        ;    STATE:=7
          MOV     ABORT,#29       ;    ABORT:=29
          CLR     MVC1            ;    CLEAR VC1 MASK
          CLR     MVO1            ;    CLEAR VO1 MASK
          CLR     VVO1            ;    CLOSE V1
          MOV     TTM0,#VDLY      ;    LOAD TIMEOUT
          CLR     TFL0            ;    RESET TIMEOUT FLAG
          SETB    TEN0            ;    ENABLE TIMEOUT ALARM
          CLR     F0              ;    CLEAR HOLD FLAG
          SJMP    S63             ;    END
S61:      SETB    LT02            ;  ELSE, EVAC-FAIL(ON)
          MOV     A,ABORT         ;    GET ABORT STATE
          MOV     STATE,A         ;    STATE:=ABORT-1
          CLR     F0              ;    CLEAR HOLD FLAG
          SJMP    S63             ;    END
S62:      SETB    F0              ;ELSE, SET HOLD FLAG
S63:      NOP                     ;  END
          LJMP    SEQR            ;RETURN
;
STATE7:   JNB     LSC1,S71        ;IF V1 CLOSED
          MOV     STATE,#8        ;  STATE:=8
          MOV     ABORT,#29       ;  ABORT:=29
          CLR     TEN0            ;  DISABLE TIMEOUT
          SETB    MVC1            ;  SET VC1 MASK
          SETB    MVO1            ;  SET VO1 MASK
          MOV     MTM0,#LKHT      ;  LOAD LEAK HOLD TIME
          CLR     TFL4            ;  RESET TIMEOUT FLAG
          CLR     F0              ;  CLEAR HOLD FLAG
          SJMP    S72             ;  END
S71:      SETB    F0              ;ELSE, SET HOLD FLAG
          NOP                     ;  END
S72:      LJMP    SEQR            ;RETURN
;
STATE8:   JNB     TFL4,S82        ;IF LEAK HOLD TIME
          CLR     C               ;  CLEAR CARRY
          MOV     A,ADIO          ;  GET PRESSURE
          SUBB    A,#PRLK         ;  SUBTRACT LEAK LIMIT
          JC      S81             ;  IF P.LE.PRLK
```

```
            MOV     STATE,#9            ;   STATE:=9
            MOV     ABORT,#30           ;   ABORT:=30
            MOV     STP2,#HSP1          ;   GET HUM. SETPOINT
            CLR     MVO6                ;   CLEAR VO6 MASK
            CLR     MVC6                ;   CLEAR VC6 MASK
            SETB    CEN2                ;   ENABLE HUM. LOOP (V6)
            MOV     MTM0,#HUMT          ;   LOAD HUM. TIMER
            CLR     TFL4                ;   RESET TIMEOUT FLAG
            CLR     LT13                ;   EVAC-IN-PROGRESS(OFF)
            SETB    LT14                ;   FILL-IN-PROGRESS(ON)
            CLR     F0                  ;   CLEAR HOLD FLAG
            SJMP    S83                 ;   END
    S81:    SETB    LT02                ; ELSE, EVAC-FAIL(ON)
            MOV     A,ABORT             ;   GET ABORT STATE
            MOV     STATE,A             ;   STATE:=ABORT-1
            CLR     F0                  ;   CLEAR HOLD FLAG
            SJMP    S83                 ;   END
    S82:    SETB    F0                  ;ELSE, SET HOLD FLAG
    S83:    NOP                         ;   END
            LJMP    SEQR                ;RETURN
;
    STATE9: JNB     TFL4,S92            ;IF HUM. TIME
            CLR     C                   ;   CLEAR CARRY
            MOV     A,ADI3              ;   GET HUMIDITY
            SUBB    A,#HNOM             ;   SUBTRACT HUM. LEVEL
            JC      S91                 ;   IF HUM.GE.HNOM
            MOV     STATE,#10           ;     STATE:=10
            MOV     ABORT,#30           ;     ABORT:=30
            MOV     MTM0,#HUMH          ;     LOAD HUM. HOLD TIMER
            CLR     TFL4                ;     RESET TIMEOUT FLAG
            CLR     F0                  ;     CLEAR HOLD FLAG
            SJMP    S83                 ;     END
    S91:    SETB    LT03                ;   ELSE, FILL-FAIL(ON)
            MOV     A,ABORT             ;     GET ABORT STATE
            MOV     STATE,A             ;     STATE:=ABORT-2
            SJMP    S93                 ;     END
    S92:    SETB    F0                  ;ELSE, SET HOLD FLAG
    S93:    NOP                         ;   END
            LJMP    SEQR                ;RETURN
;
    STATE10: JNB    TFL4,S101           ;IF HUM. HOLD TIME
            MOV     STATE,#11           ;   STATE:=11
            MOV     ABORT,#30           ;   ABORT:=30
            CLR     MVC2                ;   CLEAR VC2 MASK
            CLR     MVO2                ;   CLEAR VO2 MASK
            SETB    VVO2                ;   OPEN V2
            CLR     MVC8                ;   CLEAR VC8 MASK
            CLR     MVO8                ;   CLEAR VO8 MASK
            SETB    VVO8                ;   OPEN V8
            MOV     TTM0,#VDLY          ;   LOAD VALVE TIMEOUT
            CLR     TFL0                ;   RESET TIMEOUT FLAG
            SETB    TEN0                ;   ENABLE TIMEOUT ALARM
            MOV     STP0,#PSP1          ;   GET PRESS. SETPOINT
            CLR     MVO5                ;   CLEAR VO5 MASK
            CLR     MVC5                ;   CLEAR VC5 MASK
            SETB    CEN0                ;   ENABLE PRESS. LOOP (V5)
            CLR     F0                  ;   CLEAR HOLD FLAG
            SJMP    S102                ;   END
    S101:   SETB    F0                  ;ELSE, SET HOLD FLAG
    S102:   NOP                         ;   END
            LJMP    SEQR                ;RETURN
;
```

```
STATE11:  MOV    C,LSO2              ;TEST V2 OPEN-
          ANL    C,LS08              ;AND V8 OPEN
          JNC    S111                ;IF (V2.AND.V8) OPEN
          MOV    STATE,#12           ;   STATE:=12
          MOV    ABORT,#31           ;   ABORT:=31
          CLR    TEN0                ;   DISABLE TIMEOUT FLAG
          SETB   MVC2                ;   SET VC2 MASK
          SETB   MVO2                ;   SET VO2 MASK
          SETB   MVC8                ;   SET VC8 MASK
          SETB   MVO8                ;   SET VO8 MASK
          MOV    STP3,#CSP1          ;   GET CONC. SETPOINT
          CLR    MVO4                ;   CLEAR VO4 MASK
          CLR    MVC4                ;   CLEAR VC4 MASK
          SETB   CEN3                ;   ENABLE CONC. LOOP (V4)
          MOV    MTM0,#CNCT          ;   LOAD CONC. TIMER
          CLR    TFL4                ;   RESET TIMEOUT FLAG
          CLR    LT14                ;   FILL-IN-PROGRESS(OFF)
          SETB   LT15                ;   STERIL-IN-PROGRESS(ON)
          CLR    F0                  ;   CLEAR HOLD FLAG
          SJMP   S112                ;   END
S111:     SETB   F0                  ;  ELSE, SET HOLD FLAG
S112:     NOP                        ;     END
          LJMP   SEQR                ;RETURN
;
STATE12:  JNB    TFL4,S122           ;IF CONC. TIME
          CLR    C                   ;  CLEAR CARRY
          MOV    A,ADI3              ;  GET CONC.
          SUBB   A,#CNOM             ;  SUBTRACT CONC. LEVEL
          JC     S121                ;  IF CONC.GE.CNOM
          MOV    STATE,#13           ;    STATE:=13
          MOV    ABORT,#31           ;    ABORT:=31
          MOV    MTM0,#CONH          ;    LOAD CONC. HOLD TIMER
          CLR    TFL4                ;    RESET TIMEOUT FLAG
          CLR    F0                  ;    CLEAR HOLD FLAG
          SJMP   S123                ;    END
S121:     SETB   LT04                ;  ELSE, STERIL-FAIL(ON)
          MOV    A,ABORT             ;    GET ABORT STATE
          MOV    STATE,A             ;    STATE:=ABORT-3
          CLR    F0                  ;    CLEAR HOLD FLAG
          SJMP   S123                ;    END
S122:     SETB   F0                  ;ELSE, SET HOLD FLAG
S123:     NOP                        ;  END
          LJMP   SEQR                ;RETURN
;
STATE13:  JNB    TFL4,S132           ;IF GAS HOLD TIME
          CLR    C                   ;  CLEAR CARRY
          MOV    A,ADI3              ;  GET CONC.
          SUBB   A,#CNOM             ;  SUBTRACT CONC. LEVEL
          JC     S131                ;  IF CONC.GE.CNOM
          MOV    STATE,#14           ;    STATE:=14
          MOV    ABORT,#31           ;    ABORT:=31
          CLR    F0                  ;    CLEAR HOLD FLAG
          SJMP   S133                ;    END
S131:     SETB   LT04                ;  ELSE, STERIL-FAIL(ON)
          MOV    A,ABORT             ;    GET ABORT STATE

MOV    STATE,A             ;    STATE:=ABORT-3
          CLR    F0                  ;    CLEAR HOLD FLAG
          SJMP   S133                ;    END
```

```
S132:       SETB    F0                      ;ELSE, SET HOLD FLAG
S133:       NOP                             ;   END
            LJMP    SEQR                    ;RETURN
;
STATE14:    CLR     C                       ;CLEAR CARRY
            MOV     A,ADI1                  ;GET TEMP.
            SUBB    A,#TLOW                 ;SUBTRACT MIN. TEMP.
            JC      S141                    ;IF TEMP.GE.TMIN
            CLR     C                       ;   CLEAR CARRY
            MOV     A,#TMAX                 ;   GET MAX. TEMP LEVEL
            SUBB    A,ADI1                  ;   SUBTRACT TEMP.
            JC      S141                    ;   IF TEMP.LE.TMAX
            MOV     STATE,#15               ;      STATE:=15
            MOV     ABORT,#31               ;      ABORT:=31
            MOV     MTMO,#TSTR              ;      LOAD STERIL. TIMER
            CLR     TFL4                    ;      RESET TIMEOUT FLAG
            CLR     F0                      ;      CLEAR HOLD FLAG
            SJMP    S142                    ;      END
S141:       SETB    LTO4                    ;ELSE, STERIL-FAIL(ON)
            MOV     A,ABORT                 ;   GET ABORT STATE
            MOV     STATE,A                 ;   STATE:=ABORT-3
            CLR     F0                      ;   CLEAR HOLD FLAG
S142:       NOP                             ;   END
            LJMP    SEQR                    ;RETURN
;
STATE15:    JNB     TFL4,S151               ;IF STERIL. TIME
            MOV     STATE,#16               ;   STATE:=16
            MOV     ABORT,#31               ;   ABORT:=31
            CLR     CEN0                    ;   PRESS. LOOP (OFF)
            CLR     CEN2                    ;   HUM. LOOP (OFF)
            CLR     CEN3                    ;   GAS LOOP (OFF)
            CLR     CTR0                    ;   PRESS. OUTPUT (OFF)
            CLR     CTR2                    ;   HUM. OUTPUT (OFF)
            CLR     CTR3                    ;   GAS OUTPUT (OFF)
            CLR     VVO6                    ;   CLOSE V6
            CLR     VVO5                    ;   CLOSE V5
            CLR     VVO4                    ;   CLOSE V4
            MOV     TTMO,#VDLY              ;   LOAD TIMEOUT DELAY
            CLR     TFLO                    ;   RESET TIMEOUT FLAG
            SETB    TEN0                    ;   ENABLE TIMEOUT ALARM
            CLR     F0                      ;   CLEAR HOLD FLAG
            SJMP    S152                    ;   END
S151:       SETB    F0                      ;ELSE, SET HOLD FLAG
S152:       NOP                             ;   END
            LJMP    SEQR                    ;RETURN
;
STATE16:    MOV     C,LSC4                  ;TEST V4 CLOSED
            ANL     C,LSC5                  ;AND V5 CLOSED
            ANL     C,LSC6                  ;AND V6 CLOSED
            JNC     S161                    ;IF (V4,V5,& V6) CLOSED
            MOV     STATE,#17               ;   STATE:=17
            MOV     ABORT,#31               ;   ABORT:=31
            CLR     TEN0                    ;   DISABLE TIMEOUT ALARM
            SETB    MVC4                    ;   SET VC4 MASK
            SETB    MVO4                    ;   SET VO4 MASK
            SETB    MVC5                    ;   SET VC5 MASK
            SETB    MVO5                    ;   SET VO5 MASK
            SETB    MVC6                    ;   SET VC6 MASK
            SETB    MVO6                    ;   SET VO6 MASK
```

```
                CLR     MVC3            ; CLEAR VC3 MASK
                CLR     MVO3            ; CLEAR VO3 MASK
                SETB    VVO3            ; OPEN V3
                CLR     LT15            ; STERIL-IN-PROGRESS(OFF)
                SETB    LT16            ; PURGE-IN-PROGRESS(ON)
                MOV     TTM0,#VDLY      ; LOAD TIMEOUT DELAY
                CLR     TFL0            ; RESET TIMEOUT FLAG
                SETB    TEN0            ; ENABLE TIMEOUT ALARM
                CLR     F0              ; CLEAR HOLD FLAG
                SJMP    S162            ; END
S161:           SETB    F0              ;ELSE, SET HOLD FLAG
S162:           NOP                     ; END
                LJMP    SEQR            ;RETURN
;
STATE17:        MOV     C,LSO3          ;TEST V3 OPEN-
                ANL     C,LSO8          ;AND V8 OPEN
                JNC     S171            ;IF (V3.AND.V8) OPEN
                MOV     STATE,#18       ;   STATE:=18
                MOV     ABORT,#31       ;   ABORT:=31
                CLR     TEN0            ;   DISABLE TIMEOUT ALARM
                SETB    MVC3            ;   SET VC3 MASK
                SETB    MVO3            ;   SET VO3 MASK
                SETB    MVC8            ;   SET VC8 MASK
                SETB    MVO8            ;   SET VO8 MASK
                MOV     MTM0,#TEVC      ;   LOAD EVAC. TIMER
                CLR     TFL4            ;   RESET TIMEOUT FLAG
                CLR     F0              ;   CLEAR HOLD FLAG
                SJMP    S172            ;   END
S171:           SETB    F0              ;ELSE, SET HOLD FLAG
S172:           NOP                     ;   END
                LJMP    SEQR            ;RETURN
;
STATE18:        JNB     TFL4,S181       ;IF EVAC. TIME
                MOV     STATE,#19       ;   STATE:=19
                MOV     ABORT,#31       ;   ABORT:=31
                CLR     MVC3            ;   CLEAR VC3 MASK
                CLR     MVO3            ;   CLEAR VO3 MASK
                CLR     VVO3            ;   CLOSE V3
                CLR     MVC8            ;   CLEAR VC8 MASK
                CLR     MVO8            ;   CLEAR VO8 MASK
                CLR     VVO8            ;   CLOSE V8
                MOV     TTM0,#VDLY      ;   LOAD VALVE TIMER
                CLR     TFL0            ;   RESET TIMEOUT FLAG
                SETB    TEN0            ;   ENABLE TIMEOUT ALARM
                CLR     F0              ;   CLEAR HOLD FLAG
                SJMP    S182            ;   END
S181:           SETB    F0              ;ELSE, SET HOLD FLAG
S182:           NOP                     ;   END
                LJMP    SEQR            ;RETURN
;
STATE19:        MOV     C,LSC3          ;TEST V3 CLOSED-
                ANL     C,LSC8          ;AND V8 CLOSED
                JNC     S191            ;IF (V3.AND.V8) CLOSED
                MOV     STATE,#20       ;   STATE:=20
                MOV     ABORT,#32       ;   ABORT:=32
                CLR     TEN0            ;   DISABLE TIMEOUT ALARM
                SETB    MVC8            ;   SET VC8 MASK
                SETB    MVO8            ;   SET VO8 MASK
                MOV     STP0,#PSP1      ;   GET PRESS. SETPOINT
                CLR     MVO5            ;   CLEAR VO5 MASK
```

```
                CLR     MVC5            ;   CLEAR VC5 MASK
                SETB    CEN0            ;   ENABLE PRESS. CONTROL(V5)
                MOV     MTM0,#PN2T      ;   LOAD N2 PRESS. TIMER
                CLR     TFL4            ;   RESET TIMEOUT FLAG
                CLR     F0              ;   CLEAR HOLD FLAG
                SJMP    S192            ;   END
S191:           SETB    F0              ;ELSE, SET HOLD FLAG
S192:           NOP                     ;   END
                LJMP    SEQR            ;RETURN
;
STATE20:        JNB     TFL4,S202       ;IF REPRESS. TIME
                CLR     C               ;   CLEAR CARRY
                MOV     A,#PMAX         ;   GET MIN.PRESS. LEVEL
                SUBB    A,ADI0          ;   SUBTRACT PRESSURE
                JC      S201            ;   IF PRESS.GE.PMAX
                MOV     STATE,#21       ;     STATE:=21
                MOV     ABORT,#32       ;     ABORT:=32
                CLR     CEN0            ;     N2 LOOP (OFF)
                CLR     CTR0            ;     N2 OUTPUT (OFF)
                CLR     VV05            ;     CLOSE N2 VALVE
                MOV     TTM0,#VDLY      ;     LOAD VALVE TIMEOUT
                CLR     TFL0            ;     RESET TIMEOUT FLAG
                SETB    TEN0            ;     ENABLE TIMEOUT ALARM
                CLR     F0              ;     CLEAR HOLD FLAG
                SJMP    S202            ;     END
S201:           SETB    LT05            ;   ELSE, PURGE-FAIL(ON)
                MOV     A,ABORT         ;     GET ABORT STATE

MOV     STATE,A         ;     STATE:=ABORT-4
                CLR     F0              ;     CLEAR HOLD TIMER
                SJMP    S203            ;     END
S202:           SETB    F0              ;ELSE, SET HOLD TIMER
S203:           NOP                     ;   END
                LJMP    SEQR            ;RETURN
;
STATE21:        JNB     LSC5,S211       ;IF V5 CLOSED
                MOV     STATE,#22       ;   STATE:=22
                MOV     ABORT,#33       ;   ABORT:=33
                CLR     TEN0            ;   DISABLE TIMEOUT ALARM
                SETB    MVC5            ;   SET VC5 MASK
                SETB    MV05            ;   SET V05 MASK
                CLR     MVC3            ;   CLEAR VC3 MASK
                CLR     MV03            ;   CLEAR V03 MASK
                SETB    VV03            ;   OPEN V3
                CLR     MVC8            ;   CLEAR VC8 MASK
                CLR     MV08            ;   CLEAR V08 MASK
                SETB    VV08            ;   OPEN V8
                MOV     TTM0,#VDLY      ;   LOAD TIMEOUT DELAY
                CLR     TFL0            ;   RESET TIMEOUT FLAG
                SETB    TEN0            ;   ENABLE TIMEOUT ALARM
                CLR     F0              ;   CLEAR HOLD FLAG
                SJMP    S212            ;   END
S211:           SETB    F0              ;ELSE, SET HOLD FLAG
S212:           NOP                     ;   END
                LJMP    SEQR            ;RETURN
;
STATE22:        MOV     C,LS03          ;TEST V3 OPEN-
                ANL     C,LS08          ;AND V8 OPEN
                JNC     S221            ;IF (V3.AND.V8) OPEN
```

```
           MOV      STATE,#23        ;   STATE:=23
           MOV      ABORT,#33        ;   ABORT:=33
           CLR      TEN0             ;   DISABLE TIMEOUT ALARM
           SETB     MVC3             ;   SET VC3 MASK
           SETB     MVO3             ;   SET VO3 MASK
           SETB     MVC8             ;   SET VC8 MASK
           SETB     MVO8             ;   SET VO8 MASK
           MOV      MTM0,#DSRB       ;   LOAD DESORB TIMER
           CLR      TFL4             ;   RESET TIMEOUT FLAG
           CLR      F0               ;   CLEAR HOLD FLAG
           SJMP     S222             ;   END
S221:      SETB     F0               ;   ELSE, SET HOLD FLAG
S222:      NOP                       ;      END
           LJMP     SEQR             ;RETURN
;
STATE23:   JNB      TFL4,S231        ;IF DESORB TIME
           MOV      STATE,#24        ;   STATE:=24
           MOV      ABORT,#34        ;   ABORT:=34
           CLR      MVC3             ;   CLEAR VC3 MASK
           CLR      MVO3             ;   CLEAR VO3 MASK
           CLR      VVO3             ;   CLOSE V3
           CLR      MVC8             ;   CLEAR VC8 MASK
           CLR      MVO8             ;   CLEAR VO8 MASK
           CLR      VVO8             ;   CLOSE V8
           CLR      MVC2             ;   CLEAR VC2 MASK
           CLR      MVO2             ;   CLEAR VO2 MASK
           CLR      VVO2             ;   CLOSE V2
           MOV      TTM0,#VDLY       ;   LOAD TIMEOUT DELAY
           CLR      TFL0             ;   RESET TIMEOUT FLAG
           SETB     TEN0             ;   ENABLE TIMEOUT ALARM
           CLR      F0               ;   CLEAR HOLD FLAG
           SJMP     S232             ;   END
S231:      SETB     F0               ;ELSE, SET HOLD FLAG
S232:      NOP                       ;   END
           LJMP     SEQR             ;RETURN
;
STATE24:   MOV      C,LSC3           ;TEST V3 CLOSED-
           ANL      C,LSC8           ;AND V8 CLOSED-
           ANL      C,LSC2           ;AND V2 CLOSED
           JNC      S241             ;IF (V2,V3,V8 CLOSED)
           MOV      STATE,#25        ;   STATE:=25
           MOV      ABORT,#35        ;   ABORT:=35
           CLR      TEN0             ;   DISABLE TIMEOUT MASK
           SETB     MVC3             ;   SET VC3 MASK
           SETB     MVO3             ;   SET VO3 MASK
           SETB     MVC8             ;   SET VC8 MASK
           SETB     MVO8             ;   SET VO8 MASK
           SETB     MVC2             ;   SET VC2 MASK
           SETB     MVO2             ;   SET VO2 MASK
           SETB     LGG1             ;   SWITCH TO HIGH GAIN
           MOV      MTM0,#TLGH       ;   START LOW GAS HOLD
           LCALL    DCT0             ;   DECREMENT PURGE COUNT
           CLR      TFL4             ;   RESET TIMEOUT FLAG
           CLR      F0               ;   CLEAR HOLD FLAG
           SJMP     S242             ;   END
S241:      SETB     F0               ;ELSE, SET HOLD FLAG
S242:      NOP                       ;   END
           LJMP     SEQR             ;RETURN
;
STATE25:   JNB      TFL4,S252        ;IF LOW-HOLD TIME
```

```
            CLR     C                   ; CLEAR CARRY
            MOV     A,#CMIN             ; GET MAX. LEVEL
            SUBB    A,ADI3              ; SUBTRACT CONC.
            ORL     C,/TFL6             ; OR CARRY WITH COUNT FLAG
            JC      S251                ; IF (CONC.LE.CMIN).AND.TFL6=1
            MOV     STATE,#26           ;   STATE:=26
            MOV     ABORT,#36           ;   ABORT:=36
            CLR     CEN1                ;   DISABLE TEMP. CTRL
            CLR     PP01                ;   TURN PUMP OFF
            CLR     HT01                ;   TURN HEATER OFF
            CLR     LGG1                ;   SET LOW GAIN
            CLR     F0                  ;   CLEAR HOLD FLAG
            SJMP    S253                ;   END
S251:       MOV     A,ABORT             ; ELSE, GET ABORT STATE
            MOV     STATE,A             ;   STATE:=35
            CLR     F0                  ;   CLEAR HOLD FLAG
            SJMP    S253                ;   END
S252:       SETB    F0                  ;ELSE, SET HOLD FLAG
S253:       NOP                         ; END
            LJMP    SEQR                ;RETURN

STATE26:    LCALL   GTCT                ;DECREMENT & GET CYCLE CNT
            JNZ     S261                ;IF LAST RUN
            MOV     STATE,#27           ;   STATE:=27
            MOV     ABORT,#36           ;   ABORT:=36
            CLR     MVC2                ;   CLEAR VC2 MASK
            CLR     MVO2                ;   CLEAR VO2 MASK
            SETB    VV02                ;   OPEN V2
            CLR     MVC3                ;   CLEAR VC3 MASK
            CLR     MVO3                ;   CLEAR VO3 MASK
            SETB    VV03                ;   OPEN V3
            CLR     MVC4                ;   CLEAR VC4 MASK
            CLR     MVO4                ;   CLEAR VO4 MASK
            SETB    VV04                ;   OPEN V4
            CLR     MVC8                ;   CLEAR VC8 MASK
            CLR     MVO8                ;   CLEAR VO8 MASK
            SETB    VV08                ;   OPEN V8
            MOV     MTM0,#TDMP          ;   LOAD DUMP TIMER
            CLR     TFL4                ;   RESET TIMEOUT FLAG
            CLR     F0                  ;   CLEAR HOLD FLAG
            SJMP    S262                ;   END
S261:       MOV     STATE,#28           ;ELSE, STATE:=28
            MOV     ABORT,#36           ;   ABORT:=36
            CLR     F0                  ;   CLEAR HOLD FLAG
S262:       NOP                         ; END
            LJMP    SEQR                ;RETURN
;
STATE27:    JNB     TFL4,S271           ;IF DUMP-TIME
            MOV     STATE,#28           ;   STATE:=28
            MOV     ABORT,#36           ;   ABORT:=36
            CLR     VV02                ;   CLOSE V2
            CLR     VV03                ;   CLOSE V3
            CLR     VV04                ;   CLOSE V4
            CLR     VV08                ;   CLOSE V8
            CLR     F0                  ;   CLEAR HOLD FLAG
            SJMP    S272                ;   END
S271:       SETB    F0                  ;ELSE, SET HOLD FLAG
S272:       NOP                         ; END
            LJMP    SEQR                ;RETURN
;
```

```
STATE28: MOV     STATE,#37           ;STATE:=37
         MOV     ABORT,#36           ;ABORT:=36
         CLR     MVO5                ;CLR VO5 MASK
         CLR     MVC5                ;CLR VC5 MASK
         SETB    CEN0                ;PRESS. CONTROL(ON)
         MOV     STP0,#PATM          ;SET ATM. SETPOINT
         CLR     F0                  ;CLEAR HOLD FLAG
         LJMP    SEQR                ;RETURN
;
STATE29: MOV     C,LSC1              ;TEST V1 CLOSED-
         ANL     C,LSC2              ;AND V2 CLOSED-
         ANL     C,LSC3              ;AND V3 CLOSED-
         ANL     C,LSC4              ;AND V4 CLOSED-
         ANL     C,LSC5              ;AND V5 CLOSED-
         ANL     C,LSC6              ;AND V6 CLOSED-
         ANL     C,LSO7              ;AND V7 OPEN-
         ANL     C,LSC8              ;AND V8 CLOSED-
         ANL     C,SWC2              ;AND SW2 PUSHED
         JNC     S291                ;IF RESET
         MOV     STATE,#2            ;  STATE:=2
         MOV     ABORT,#0            ;  ABORT:=0
         MOV     STAT,#00H           ;  RESET STATUS
         MOV     CC00,#00H           ;  RESET ALARM LIGHTS
         MOV     CC01,#01H           ;  RESET RUN LIGHTS
         CLR     F0                  ;  CLEAR HOLD FLAG
         SJMP    S292                ;  END
S291:    MOV     CTRL,#00H           ;ELSE, RESET CONTROLS
         MOV     TCEN,#00H           ;  RESET ALARMS
         MOV     MSK0,#00H           ;  RESET CLOSED MASKS
         MOV     MSK1,#00H           ;  RESET OPEN MASKS
         MOV     MSK2,#00H           ;  RESET MISC. MASKS
         MOV     CC02,#40H           ;  RESET VALVES
         MOV     CC03,#00H           ;  RESET MISC. OUTPUTS
         MOV     CC01,#00H           ;  TURN CYCLE LIGHTS OFF
         SETB    LTO2                ;  EVAC-FAIL(ON)
         SETB    F0                  ;  SET HOLD FLAG
S292:    NOP                         ;  END
         LJMP    SEQR                ;RETURN
;
STATE30: MOV     C,LSC1              ;TEST V1 CLOSED-
         ANL     C,LSC2              ;AND V2 CLOSED-
         ANL     C,LSC3              ;AND V3 CLOSED-
         ANL     C,LSC4              ;AND V4 CLOSED-
         ANL     C,LSC5              ;AND V5 CLOSED-
         ANL     C,LSC6              ;AND V6 CLOSED-
         ANL     C,LSO7              ;AND V7 OPEN-
         ANL     C,LSC8              ;AND V8 CLOSED-
         ANL     C,SWC2              ;AND SW2 PUSHED
         JNC     S301                ;IF RESET
         MOV     STATE,#2            ;  STATE:=2
         MOV     ABORT,#0            ;  ABORT:=0
         MOV     STAT,#00H           ;  RESET STATUS
         MOV     CC00,#00H           ;  RESET ALARM LIGHTS
         MOV     CC01,#01H           ;  RESET RUN LIGHTS
         CLR     F0                  ;  CLEAR HOLD FLAG
         SJMP    S302                ;  END
S301:    MOV     CTRL,#00H           ;ELSE, RESET CONTROLS
         MOV     TCEN,#00H           ;  RESET ALARMS
         MOV     MSK0,#00H           ;  RESET CLOSED MASKS
         MOV     MSK1,#00H           ;  RESET OPEN MASKS
```

```
          MOV    MSK2,#00H       ; RESET MISC. MASKS
          MOV    CCO2,#40H       ; RESET VALVES
          MOV    CCO3,#00H       ; RESET MISC. OUTPUTS
          MOV    CCO1,#00H       ; TURN CYCLE LIGHTS OFF
          SETB   LT03            ; FILL-FAIL(ON)
          SETB   F0              ; SET HOLD FLAG
S302:     NOP                    ; END
          LJMP   SEQR            ;RETURN
STATE31:  MOV    C,LSC1          ;TEST V1 CLOSED-
          ANL    C,LSO2          ;AND V2 OPEN-
          ANL    C,LSC3          ;AND V3 CLOSED
          ANL    C,LSC4          ;AND V4 CLOSED-
          ANL    C,LSC6          ;AND V6 CLOSED-
          ANL    C,LSC7          ;AND V7 CLOSED-
          ANL    C,LSC8          ;AND V8 CLOSED-
          ANL    C,SWC2          ;AND SW2 PUSHED
          JNC    S311            ;IF RESET
          MOV    STATE,#20       ;  STATE:=20
          MOV    ABORT,#31       ;  ABORT:=32
          MOV    STAT,#00H       ;  RESET STATUS
          MOV    MSK0,#0EFH      ;  SET ALL CLOSED MASKS
          MOV    MSK1,#0EFH      ;  SET ALL OPEN MASKS
          MOV    MSK2,#001H      ;  SET MISC. MASKS
          MOV    CCO0,#00H       ;  RESET ALARM LIGHTS
          MOV    CCO1,#22H       ;  RESET RUN LIGHTS
          CLR    F0              ;  CLEAR HOLD FLAG
          SJMP   S312            ;  END
S311:     MOV    CTRL,#03H       ;ELSE, RESET CONTROLS
          MOV    TCEN,#00H       ;  RESET ALARMS
          MOV    MSK0,#00H       ;  RESET CLOSED MASKS
          MOV    MSK1,#00H       ;  RESET OPEN MASKS
          MOV    MSK2,#00H       ;  RESET MISC. MASKS
          MOV    CCO2,#02H       ;  RESET ALL VALVES
          MOV    CCO3,#01H       ;  RESET MISC. OUTPUTS
          SETB   LT04            ;  STERIL-FAIL(ON)
          SETB   F0              ;  SET HOLD FLAG
S312:     NOP                    ;  END
          LJMP   SEQR            ;RETURN
;
STATE32:  MOV    C,LSC5          ;TEST V5 CLOSED
          ANL    C,SWC2          ;AND SW2
          JNC    S321            ;IF (V5 CLOSED & SW2 PUSHED)
          MOV    STATE,#19       ;  STATE:=19
          MOV    ABORT,#32       ;  ABORT:=32
          CLR    F0              ;  CLEAR HOLD FLAG
          SJMP   S322            ;  END
S321:     MOV    CCO2,#02H       ;ELSE, RESET ALL VALVES
          SETB   F0              ;  SET HOLD FLAG
S322:     NOP                    ;  END
          LJMP   SEQR            ;RETURN
;
STATE33:  MOV    C,SWC2          ;TEST SW2
          JNC    S331            ;IF PUSHED
          MOV    STATE,#23       ;  STATE:=23
          MOV    ABORT,#33       ;  ABORT:=34
          CLR    F0              ;  CLEAR HOLD FLAG
          SJMP   S332            ;  END
S331:     SETB   F0              ;ELSE, SET HOLD FLAG
S332:     NOP                    ;  END
          LJMP   SEQR            ;RETURN
;
```

```
STATE34: MOV     C,SWC2              ;TEST SW2
         JNC     S341                ;IF PUSHED

MOV     STATE,#25           ;   STATE:=25
         MOV     ABORT,#35           ;   ABORT:=35
         LCALL   DCT0                ;   DECREMENT PURGE COUNT
         CLR     F0                  ;   CLEAR HOLD FLAG
         SJMP    S342                ;   END
S341:    SETB    F0                  ;ELSE, SET HOLD FLAG
S342:    NOP                         ;   END
         LJMP    SEQR                ;RETURN
;
STATE35: MOV     C,LSC1              ;TEST V1 CLOSED-
         ANL     C,LSO2              ;AND V2 OPEN-
         ANL     C,LSC3              ;AND V3 CLOSED-
         ANL     C,LSC4              ;AND V4 CLOSED-
         ANL     C,LSC5              ;AND V5 CLOSED-
         ANL     C,LSC6              ;AND V6 CLOSED-
         ANL     C,LSC7              ;AND V7 CLOSED-
         ANL     C,LSC8              ;AND V8 CLOSED-
         JNC     S351                ;IF RESET
         MOV     STATE,#20           ;   STATE:=20
         MOV     ABORT,#32           ;   ABORT:=32
         MOV     STAT,#00H           ;   RESET STATUS
         MOV     MSK0,#0EFH          ;   SET ALL CLOSED MASKS
         MOV     MSK1,#0EFH          ;   SET ALL OPEN MASKS
         MOV     MSK2,#001H          ;   SET MISC. MASKS
         MOV     CC00,#00H           ;   RESET ALARM LIGHTS
         MOV     CC01,#22H           ;   RESET RUN LIGHTS
         MOV     STP0,#PSP1          ;   LOAD PRESS. SETPOINT
         SETB    CEN0                ;   ENABLE PRESSURE CONTROL
         MOV     MTM0,#PN2T          ;   SET PRESSURE TIMER
         CLR     TFL4                ;   CLEAR TIMER FLAG
         CLR     F0                  ;   CLEAR HOLD FLAG
         SJMP    S352                ;   END
S351:    MOV     CTRL,#03H           ;ELSE, RESET CONTROLS
         MOV     TCEN,#00H           ;   RESET ALARMS
         MOV     MSK0,#00H           ;   RESET CLOSED MASKS
         MOV     MSK1,#00H           ;   RESET OPEN MASKS
         MOV     MSK2,#00H           ;   RESET MISC. MASKS
         MOV     CC02,#02H           ;   RESET ALL VALVES
         MOV     CC03,#01H           ;   RESET MISC. OUTPUTS
         SETB    F0                  ;   SET HOLD FLAG
S352:    NOP                         ;   END
         LJMP    SEQR                ;RETURN
;

STATE36: MOV     C,SWC2              ;TEST SW2
         JNC     S361                ;IF PUSHED
         MOV     STATE,#26           ;   STATE:=26
         MOV     ABORT,#37           ;   ABORT:=37
         CLR     F0                  ;   CLEAR HOLD FLAG
         SJMP    S362                ;   END
S361:    SETB    F0                  ;ELSE, SET HOLD FLAG
S362:    NOP                         ;   END
         LJMP    SEQR                ;RETURN
;
```

```
STATE37: CLR     C              ;CLEAR CARRY
         MOV     A,#PATM        ;GET ATM SETPOINT
         SUBB    A,ADIO         ;SUBTRACT PRESSURE
         JC      S371           ;IF PRESS.GT.ATM
         MOV     STATE,#38      ;   STATE:=38
         MOV     ABORT,#0       ;   ABORT:=0
         CLR     MVC7           ;   CLEAR VC7 MASK
         CLR     MVO7           ;   CLEAR VO7 MASK
         CLR     CENO           ;   N2 LOOP(OFF)
         CLR     CTRO           ;   N2 OUTP(OFF)
         CLR     VV05           ;   CLOSE N2 VALVE
         SETB    VV07           ;   OPEN V7
         CLR     LT16           ;   PURGE-IN-PROGRESS(OFF)
         SETB    LT17           ;   REMOVE-LOAD(ON)
         CLR     F0             ;   CLEAR HOLD FLAG
         SJMP    S372           ;   END
S371:    SETB    F0             ;ELSE, SET HOLD FLAG
S372:    NOP                    ;   END
         LJMP    SEQR           ;RETURN
;
STATE38: JNB     SWC2,S381      ;IF SW2 PUSHED
         MOV     STATE,#0       ;   STATE:=0 (RESET)
         MOV     ABORT,#0       ;   ABORT:=0
         CLR     F0             ;   CLEAR HOLD FLAG
         SJMP    S382           ;   END
S381:    SETB    F0             ;ELSE, SET HOLD FLAG
S382:    NOP                    ;   END
         LJMP    SEQR           ;RETURN
;
```

In the foregoing specification, the invention has been described with reference to a specific exemplary embodiment thereof. It will, however, be evident that various modifications and changes may be made thereunto without parting from the broader spirit and scope of the invention as set forth in the appended claims. For example, as will be appreciated by those of ordinary skill in the art familiar with this specification, the apparatus disclosed herein may be suitable for use in connection with various types of gaseous treatment systems, such as those which employ toxic gases, e.g., without limitation, bleaching gases, fumigants, sterilants, etc. The specification and drawings are, accordingly, to be regarded in an illustrative rather than a restrictive sense.

What is claimed is:

1. Apparatus for treating articles with a gas, comprising:
   chamber means for receiving an article to be treated; means for supplying a gas to the chamber means comprising first valve means coupled to the chamber means for supplying the gas to the chamber means, means for removing the gas from the chamber means after a predetermined time interval, means for measuring a plurality of measured parameters in said chamber means and for generating a plurality of electrical signals associated with ones of the measured parameters, electronic control means receiving said plurality of electrical signals associated with ones of the measured parameters from said chamber means for controlling said valve means and said means for removing, said electronic control means comprising computer means for cycling said apparatus through a plurality of states in accordance with a predetermined sequence of instructions, said computer means including means for aborting the operation of said apparatus to one of a plurality of defined failure states having predefined conditions in response to a failure of said apparatus, said selected failure state dependent on the state in said cycle in which the failure occurred, and further comprising means for cycling said apparatus in accordance with said predetermined sequence to a further defined state once one of said defined failure states is reached, said further defined state comprising one of the states in accordance with said predetermined sequence of instructions, said further defined state being dependent on the defined failure state reached and being a state which maintains said apparatus within acceptable standards of safety.

2. The apparatus recited in claim 1 wherein said means for supplying the gas to the chamber means comprises means for supplying a sterilizing gas having bacteriocidal, sporicidal, fungicidal or virocidal properties, whereby said article is sterilized by said gas.

3. The apparatus recited in claim 2 wherein said means for supplying a gas to the chamber means comprises means for supplying a sterilizing gas comprising chlorine dioxide.

4. The apparatus recited in claim 2 wherein said means for removing comprises vacuum pump means and additional valve means.

5. The apparatus recited in claim 2, further comprising means for monitoring for proper operation of said computer means, said monitoring means issuing a disabling signal to prevent actuation of said valve means in the event of a failure of said computer means.

6. The apparatus recited in claim 2, wherein said valve means moves between a first state and a second state in response to instructions from said computer means, and further comprising timer means for generating an alarm signal if said valve means does not move from said first to second state in a predetermined time interval.

7. The apparatus recited in claim 2, wherein said first valve means comprises first and second limit switch means, said first limit switch means indicating when said first valve means is open and said second limit switch means indicating when said first valve means is closed, said first and second limit switch means being in opposite states such that when said first limit switch means is closed, said second limit switch means is open.

8. The apparatus recited in claim 7, further comprising means for monitoring the state of said first and second switch means, and further comprising means for generating an alarm signal if said first and second switch means are not in the proper states.

9. The apparatus recited in claim 7, wherein said electronic control means comprises memory means, and further comprising means for receiving input signals from said limit switches of said valve means indicative of the closed or open condition of said valve means and means for transmitting output signals to said valve means to selectively open or close said valve means, image signals of said input and output signals being stored in said memory means.

10. The apparatus recited in claim 9, further comprising means for disabling said output signals from being transmitted to said valve means except when an enabling signal is issued by said computer means to said disabling means.

11. The apparatus recited in claim 9, further comprising mask means stored in said memory means, said computer means comparing respective one of said image signals of said input and output signals with each of the and generating an alarm signal if said input and output image signals do not agree in response to the setting of a bit in said mask means.

12. The apparatus recited in claim 2, wherein said sterilizing gas is generated from at least two component parts, and further including first means for receiving a first component part of the gas, second means for receiving a second component part of the gas, means for contacting said first and second component parts so as to cause said first and second component parts to react with each other to generate said sterilizing gas, said means for contacting being controlled by said computer means in response to the measurement of selected ones of said plurality of measured parameters.

13. The apparatus recited in claim 12, further comprising second valve means for supplying a relatively stable gas to said chamber means.

14. The apparatus recited in claim 12, further comprising valve means for supplying filtered air to said chamber means.

15. The apparatus recited in claim 12, further comprising valve means for supplying water vapor to said chamber means to affect the humidity level in said chamber.

16. The apparatus recited in claim 12 wherein said measuring means comprises means for measuring temperature, means for measuring pressure and means for measuring humidity in said chamber means and further including means for measuring the concentration of said sterilizing gas in said chamber means.

17. The apparatus recited in claim 12 wherein said means for supplying a sterilizing gas comprises means for supplying chlorine dioxide and said first means for receiving a first component part comprises means for receiving chlorine gas and said second means for receiving a second component part comprises means for receiving soduim chlorite.

18. Apparatus for treating articles with a gas comprising:
 first means for receiving a first component;
 second means for receiving a second component, said first and second components, when reacted together, forming a gas;
 means for reacting said two components together for forming said gas;
 chamber means for receiving an article to be treated with the gas;
 first valve means for supplying said gas to said chamber means to treat said article in said chamber means;
 means for measuring a plurality of measured parameters in said chamber means;
 means for removing said gas from said chamber means;
 electronic controller means for controlling said means for reacting, first valve means for supplying and means for removing comprising computer means executing a predetermined sequence of steps so as to cycle said apparatus through a series of successive states defining a cycle in which said article is treated by said gas and wherein said gas is thereafter removed from said chamber means so as to render said chamber means within acceptable standards of safety, said electronic controller means including means for aborting the operation of said apparatus to one of a plurality of defined failure states having predefined conditions in response to a failure of said apparatus, said selected failure state dependent on the state in said cycle in which the failure occurred, and further comprising means for cycling said apparatus in accordance with said predetermined sequence to a further defined state once one of said defined failure states is reached, said further defined state comprising one of the states in said cycle, said further defined state dependent on the defined failure state reached and being a state which maintains said apparatus within acceptable standards of safety.

19. The apparatus recited in claim 18 wherein said first valve means for supplying the gas to the chamber means comprises means for supplying a sterilizing gas, whereby said article is sterilized by said gas.

20. The apparatus recited in claim 19 wherein said means for removing comprises vacuum pump means and additional valve means.

21. The apparatus recited in claim 19, further comprising means for monitoring for proper operation of said computer means, said monitoring means issuing a disabling signal to prevent actuation of said valve means in the event of a failure of said computer means.

22. The apparatus recited in claim 19, wherein said valve means moves between a first state and a second state in response to instructions from said computer means, and further comprising timer means for generating an alarm signal if said valve means does not move from said first to second state in a predetermined time interval.

23. The apparatus recited in claim 19 wherein said first valve means for supplying a sterilizing gas comprises means for supplying chlorine dioxide.

24. The apparatus recited in claim 23 wherein said first valve means means for supplying sterilizing gas comprises means for supplying chlorine dioxide and said means for receiving said first component comprises means for receiving chlorine gas and said means for receiving said second component comprises means for receiving sodium chlorite.

25. The apparatus recited in claim 19, wherein said valve means comprises first and second switch means, said first switch means indicating when said valve means is open and said second switch means indicating when said valve means is closed, said first and second switch means being in opposite states such that when said first switch means is closed, said second switch means is open.

26. The apparatus recited in claim 25, further comprising means for monitoring the state of said first and second switch means, and further comprising means for generating an alarm signal if said first and second switch means are not in the proper states.

27. The apparatus recited in claim 19, wherein said electronic control means comprises memory means, and further comprising means for receiving input signals from said valve means indicative of the closed or open condition of said valve means and means for transmitting output signals to said valve means to selectively open or close said valve means, images of said input and output signals being stored in said memory means.

28. The apparatus recited in claim 27, further comprising means for disabling said output signals from being transmitted to said valve means except when an enabling signal is issued by said computer means.

29. The apparatus recited in claim 27, further comprising mask means stored in said memory means, said computer means comparing respective ones of said images of said input and output signals with each other and generating an alarm signal if said input and output images do not agree in response to the setting of a bit in said mask means.

30. The apparatus recited in claim 19 wherein said computer means comprises means for receiving a plurality of electrical signals associated with ones of measured parameters from said chamber means for controlling the operation of said means for reacting, means for supplying and means for removing.

31. The apparatus recited in claim 30, wherein said means for reacting comprises second valve means for allowing said first and second components to contact so as to react with each other to generate said sterilizing gas, said second valve means being controlled by said computer means in response to the measurement of selected ones of said plurality of measured parameters.

32. The apparatus recited in claim 31, further comprising valve means for supplying a relatively stable gas to said chamber means.

33. The apparatus recited in claim 31, further comprising valve means for supplying filtered air to said chamber means.

34. The apparatus recited in claim 31, further comprising valve means for supplying water vapor to said chamber means to affect the humidity level in said chamber.

35. The apparatus recited in claim 31 wherein said measuring means comprise means for measuring a plurality of measured parameters including means for measuring temperature, means for measuring pressure and means for measuring humidity in said chamber means and further comprising means for measuring the concentration of said sterilizing gas in said chamber means.

36. Apparatus for treating articles with a gas comprising:
chamber means for receiving an article to be treated;
means for supplying a gas to the chamber means comprising valve means coupled to the chamber means for supplying the gas to the chamber means, means for removing the gas from the chamber means after a predetermined time interval, means for measuring a plurality of measured parameters in the chamber means, electronic control means receiving a plurality of electrical signals associated with ones of the measured parameters from said chamber means for controlling said valve means and said means for removing, said electronic control means comprising computer means for cycling said apparatus through a plurality of states in accordance with a predetermined sequence of instructions,
said computer means including memory means, and further comprising means for receiving input signals from said valve means indicative of the closed or open condition of said valve means and means for transmitting output signals to said valve means to open or close selectively said valve means, image signals of said input and output signals being stored in said memory means,
mask means being stored in said memory means, said computer means comparing respective ones of said image signals of said input and output signals with each other and generating an alarm signal if said input and output image signals do not agree in response to the setting of a bit in said mask means,
said computer means including means for aborting the operation of said apparatus to one of a plurality of defined failure states having predefined conditions in response to a failure of said apparatus, said selected failure state dependent on the state in said cycle in which the failure occurred, and further comprising means for cycling said apparatus in accordance with said predetermined sequence to a further defined state once one of said defined failure states is reached, said further defined state comprising one of the states in accordance with said predetermined sequence of instructions, said further defined state dependent upon the defined failure state reached and being a state which maintains said apparatus within acceptable standards of safety.

37. The apparatus recited in claim 36, wherein said means for supplying a gas comprises means for supplying a sterilizing gas, whereby said article is sterilized by said gas.

38. The apparatus recited in claim 37 wherein said means for supplying a sterilizing gas comprises means for supplying chlorine dioxide.

39. The apparatus recited in claim 37 wherein said means for removing comprises vacuum pump means and additional valve means.

40. The apparatus recited in claim 37, further comprising means for disabling said output signals from being transmitted to said valve means except when an enabling signal is issued by said computer means.

41. The apparatus recited in claim 37, further comprising means for monitoring for proper operation of said computer means, said monitoring means issuing a disabling signal to prevent actuation of said valve means in the event of a failure of said computer means.

42. The apparatus recited in claim 37, wherein said valve means moves between a first state and a second state in response to instructions from said computer means, and further comprising timer means for generating an alarm signal if said valve means does not move from said first to second state in a predetermined time interval.

43. The apparatus recited in claim 37, wherein said valve means comprises first and second switch means, said first switch means indicating when said valve means is open and said second switch means indicating when said valve means is closed, said first and second switch means being in opposite states such that when said first switch means is closed, said second switch means is open.

44. The apparatus recited in claim 43, further comprising means for monitoring the state of said first and second switch means, and further comprising means for generating an alarm signal if said first and second switch means are not in the proper states.

45. The apparatus recited in claim 37, wherein said sterilizing gas is generated from at least two component parts, and further including first means for receiving a first component part of the gas, second means for receiving a second component part of the gas, means for allowing said first and second component parts to react with each other to generate said sterilizing gas, said means for allowing being controlled by said computer means in response to the measurement of selected ones of said plurality of measured parameters.

46. The apparatus recited in claim 45, further comprising valve means for supplying a relatively stable gas to said chamber means.

47. The apparatus recited in claim 45, further comprising valve means for supplying filtered air to said chamber means.

48. The apparatus recited in claim 45, further comprising valve means for supplying water vapor to said chamber means to affect the humidity level in said chamber.

49. The apparatus recited in claim 45, wherein said means for measuring a plurality of measured parameters include means for measuring temperature, means for measuring pressure, and means for measuring humidity in said chamber means and further comprising means for measuring the concentration of said sterilizing gas in said chamber means.

50. The apparatus recited in claim 45 wherein said means for supplying a sterilizing gas comprises means for supplying chlorine dioxide and said first means for receiving said first component part comprises means for receiving chlorine gas and said second means for receiving said second component part comprises means for receiving sodium chlorite.

* * * * *